US006207399B1

(12) United States Patent
Hemker et al.

(10) Patent No.: US 6,207,399 B1
(45) Date of Patent: Mar. 27, 2001

(54) METHODS OF DETERMINING ENDOGENOUS THROMBIN POTENTIAL (ETP) AND THROMBIN SUBSTRATES FOR USE IN SAID METHODS

(75) Inventors: Hendrik Coenraad Hemker, Tongerstraat 41, NL-6211 LM Maastricht; Dirk Thomas Sigurd Rijkers, Eindhoven; Godefridus Ignatius Tesser, Nijmegen, all of (NL)

(73) Assignee: Hendrik Coenraad Hemker, Maastricht (NL)

( * ) Notice: Subject to any disclaimer, the term of this patent is extended or adjusted under 35 U.S.C. 154(b) by 0 days.

(21) Appl. No.: 08/860,808

(22) PCT Filed: Jan. 10, 1996

(86) PCT No.: PCT/NL96/00018

§ 371 Date: Sep. 5, 1997

§ 102(e) Date: Sep. 5, 1997

(87) PCT Pub. No.: WO96/21740

PCT Pub. Date: Jul. 18, 1996

(30) Foreign Application Priority Data

Jan. 10, 1995 (EP) .................................................. 9500043

(51) Int. Cl.[7] ........................... C12Q 1/56; G01N 33/86; C07K 5/00; C07K 7/06

(52) U.S. Cl. ............................. 435/13; 436/69; 530/300; 530/330

(58) Field of Search ................................ 435/13; 436/69; 530/300, 330

(56) References Cited

U.S. PATENT DOCUMENTS 4,214,049 7/1980 Ekenstam et al. .
4,247,454 1/1981 Ekenstam et al. .
5,192,689 * 3/1993 Hemker ................................ 436/69

FOREIGN PATENT DOCUMENTS 280 610 8/1988 (EP) .
420 332 4/1991 (EP) .
86/01209 2/1986 (WO) .

OTHER PUBLICATIONS

Weber et al: "Kinetic and Crystallographic Studies of Thombin with Ac–(D)Phe–Pro–boroArg–OH and its Lysine, Amidine, Homolysine, and Omithine Analogs", Biochemistry 1995,vol. 34,No. 11, pp. 3750–3757.

Hilpert et al: "Design and Synthesis of Potent and Highly Selective Thrombin Inhibitors", Journal of Medicinal Chemistry, 1994, vol. 37, No. 23, pp. 3889–3901.

St.Laurent et al: "Active Site–directed Thrombin Inhibitors–II. Studies Related to Arginine/Guanidine Bioisosteres", Bioorganic & Medicinal Chemistry, vol. 3, No. 8, pp. 1145–1156, 1995.

Levy et al: "Potent and Selective Thrombin Inhibitors Incorporating the Constrained Arginine Mimic $_L$–3–Piperidyl(N–guanidino)alanine at $P_1$"; Journal of Medicinal Chemistry, vol. 39, No. 23, Nov.8,1996, pp 4527–4530.

Semple et al: "Design, Synthesis, and Evolution of a Novel, Selective, and Orally Bioavailable Class of Thrombin Inhibitors: P1–Argininal Derivatives Incorporating P3–P4 Lactam Sulfonamide Moieties[1]", J. Med. Chem, 1996, vol. 39, No. 23, pp 4531–4536.

Chang: "Thrombin specificity—Requirement for apolar amino acids adjacent to the thrombin cleavage site of polypeptide substrate", J. Biochem. 151, (1985) 217–224.

Hemker et al: "Continuous registration of thrombin generation in plasma, its use for the determination of the thrombin potential", Thrombosis and Haemostasis, vol. 70, No. 4, 1993, pp 617–614, XP000567560, see the whole document.

Rijkers et al: "Design and synthesis of thrombin substrates with modified kinetic parameters", Thrombosis Research, vol. 79, No. 5–6, Sep. 15, 1995, pp 491–499, XP002000556, see the whole document.

Hemker et al: "Thrombin generation in plasma: its assessment via the endogenous thrombin potential", Thrombosis and Haemostasis, vol. 74, No. 1, Jul. 1995, pp 134–138, XP000195941, see the whole document.

Bode et al: "The refined 1.0 A crystal structure of human α–thrombin: interaction with D–Phe–Pro–Arg chloromethylketone and significance of the Tyr–Pro–Pro–Trp insertion segment", The EMBO Journal, vol. 8, No. 11, pp 3467–3475, 1989.

* cited by examiner

*Primary Examiner*—David Saunders
*Assistant Examiner*—Mary Beth Tung
(74) *Attorney, Agent, or Firm*—Pillsbury Winthrop LLP

(57) ABSTRACT

A method for determining the endogenous thrombin potential of a sample having a total anticoagulant activity of or equivalent to at least 0.07 U ISH/ml, includes using a thrombin substrate or a salt thereof that is soluble in the sample to determine the ETP of the sample. Suitable thrombin substrate include those of the formula P-Val-Xaa-S, in which P is an amino protective group, that is non-aromatic and polar, Val is a valine residue attached via a peptide bond to Xaa, Xaa is an amino acid residue comprising a terminal guanidino group or ureido group separated by at least 2 carbon atoms from the peptide backbond the amino acid residue is attached to S and S is a signal group such as a chromophore that can be enzymatically hydrolyzed. Other substrates include substrates comprising the structure Zaa-Pipecolyl-Yaa-S or Zaa-Pro-Yaa-S, wherein Zaa represents D-Phenylalanine, D-Tryptophan or D-Tyrosine, Pro represents proline, Yaa is an amino acid residue other than arginine and S is a signal marker can also be used. The substrates Boc-Gly-Val-Arg-pNA and H-Glu-Gly-Gly-Val-Arg-pNA are also applicable. Furthermore ETP determination methods can be improved by addition of hydroxylamine to the sample to circumvent defibrination of the sample.

36 Claims, 10 Drawing Sheets

```
                          SEQUENCE LISTING

<160> NUMBER OF SEQ ID NOS:  25

<210> SEQ ID NO 1
<211> LENGTH: 14
<212> TYPE: PRT
<213> ORGANISM: Artificial Sequence
<220> FEATURE:
<221> NAME/KEY: UNSURE
<222> LOCATION: (14)
<223> OTHER INFORMATION: Xaa is Arg-NHCH3
<223> OTHER INFORMATION: Description of Artificial Sequence:peptide

<400> SEQUENCE: 1

Ala Glu Gly Gly Gly Val Arg Gly Pro Arg Val Val Glu Xaa
  1               5                   10


<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:peptide
<221> NAME/KEY: UNSURE
```

-continued

```
<222> LOCATION: (1)
<223> OTHER INFORMATION: Xaa is CH3-O-CO-CH2-CO-L-Pro
<221> NAME/KEY: UNSURE
<222> LOCATION: (2)
<223> OTHER INFORMATION: Xaa is Arg-p-nitroanilide-CO
<221> NAME/KEY: UNSURE
<222> LOCATION: (4)
<223> OTHER INFORMATION: Xaa is Arg-p-nitroanilide

<400> SEQUENCE: 2

Xaa Xaa Pro Xaa
  1


<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (5)
<223> OTHER INFORMATION: Xaa is Arg-p-nitroanilide

<400> SEQUENCE: 3

Glu Gly Gly Val Xaa
  1               5


<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (2)..(4)
<223> OTHER INFORMATION: 1 to 3 residues may be missing
<221> NAME/KEY: UNSURE
<222> LOCATION: (6)
<223> OTHER INFORMATION: Xaa is Arg-p-nitroanilide

<400> SEQUENCE: 4

Glu Gly Gly Gly Val Xaa
  1               5


<210> SEQ ID NO 5
<211> LENGTH: 4
<212> TYPE: PRT
<213> ORGANISM: Artificial Sequence
<220> FEATURE:
<221> NAME/KEY: UNSURE
<222> LOCATION: (1)
<223> OTHER INFORMATION: Xaa is Boc-Glu(O-t-Bu)
<221> NAME/KEY: UNSURE
<222> LOCATION: (4)
<223> OTHER INFORMATION: Xaa is Arg-p-nitroanilide
<223> OTHER INFORMATION: Description of Artificial Sequence:peptide

<400> SEQUENCE: 5

Xaa Gly Val Xaa
  1


<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (4)
<223> OTHER INFORMATION: Xaa is Arg--p-nitroanilide
```

-continued

<400> SEQUENCE: 6

```
Glu Gly Val Xaa
  1
```

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (1)
<223> OTHER INFORMATION: Xaa is Boc-Glu(O-t-Bu)
<221> NAME/KEY: UNSURE
<222> LOCATION: (5)
<223> OTHER INFORMATION: Xaa is Arg-p-nitroanilide

<400> SEQUENCE: 7

```
Xaa Gly Gly Val Xaa
  1               5
```

<210> SEQ ID NO 8
<211> LENGTH: 6
<212> TYPE: PRT
<213> ORGANISM: Artificial Sequence
<220> FEATURE:
<221> NAME/KEY: UNSURE
<222> LOCATION: (1)
<223> OTHER INFORMATION: Xaa is Boc-Glu(O-t-Bu)
<221> NAME/KEY: UNSURE
<222> LOCATION: (6)
<223> OTHER INFORMATION: Xaa is Arg-p-nitroanilide
<223> OTHER INFORMATION: Description of Artificial Sequence:peptide

<400> SEQUENCE: 8

```
Xaa Gly Gly Gly Val Xaa
  1               5
```

<210> SEQ ID NO 9
<211> LENGTH: 6
<212> TYPE: PRT
<213> ORGANISM: Artificial Sequence
<220> FEATURE:
<221> NAME/KEY: UNSURE
<222> LOCATION: (6)
<223> OTHER INFORMATION: Xaa is Arg-p-nitroanilide
<223> OTHER INFORMATION: Description of Artificial Sequence:peptide

<400> SEQUENCE: 9

```
Glu Gly Gly Gly Val Xaa
  1               5
```

<210> SEQ ID NO 10
<211> LENGTH: 6
<212> TYPE: PRT
<213> ORGANISM: Artificial Sequence
<220> FEATURE:
<221> NAME/KEY: UNSURE
<222> LOCATION: (1)
<223> OTHER INFORMATION: Xaa is Boc-Glu(O-t-Bu)
<221> NAME/KEY: UNSURE
<222> LOCATION: (6)
<223> OTHER INFORMATION: Xaa is Arg-p-nitroanilide
<223> OTHER INFORMATION: Description of Artificial Sequence:peptide

<400> SEQUENCE: 10

```
Xaa Gly Pro Gly Val Xaa
  1               5
```

-continued

```
<210> SEQ ID NO 11
<211> LENGTH: 6
<212> TYPE: PRT
<213> ORGANISM: Artificial Sequence
<220> FEATURE:
<221> NAME/KEY: UNSURE
<222> LOCATION: (6)
<223> OTHER INFORMATION: Xaa is Arg-p-nitroanilide
<223> OTHER INFORMATION: Description of Artificial Sequence:peptide

<400> SEQUENCE: 11

Glu Gly Pro Gly Val Xaa
  1               5


<210> SEQ ID NO 12
<211> LENGTH: 6
<212> TYPE: PRT
<213> ORGANISM: Artificial Sequence
<220> FEATURE:
<221> NAME/KEY: UNSURE
<222> LOCATION: (1)
<223> OTHER INFORMATION: Xaa is Boc-Glu(O-t-Bu)
<221> NAME/KEY: UNSURE
<222> LOCATION: (6)
<223> OTHER INFORMATION: Xaa is Arg-p-nitroanilide
<223> OTHER INFORMATION: Description of Artificial Sequence:peptide

<400> SEQUENCE: 12

Xaa Pro Gly Gly Val Xaa
  1               5


<210> SEQ ID NO 13
<211> LENGTH: 6
<212> TYPE: PRT
<213> ORGANISM: Artificial Sequence
<220> FEATURE:
<221> NAME/KEY: UNSURE
<222> LOCATION: (6)
<223> OTHER INFORMATION: Xaa is Arg-p-nitroanilide
<223> OTHER INFORMATION: Description of Artificial Sequence:peptide

<400> SEQUENCE: 13

Glu Pro Gly Gly Val Xaa
  1               5


<210> SEQ ID NO 14
<211> LENGTH: 5
<212> TYPE: PRT
<213> ORGANISM: Artificial Sequence
<220> FEATURE:
<221> NAME/KEY: UNSURE
<222> LOCATION: (5)
<223> OTHER INFORMATION: Xaa is Arg-p-nitroanilide
<223> OTHER INFORMATION: Description of Artificial Sequence:peptide

<400> SEQUENCE: 14

Gly Gly Gly Val Xaa
  1               5


<210> SEQ ID NO 15
<211> LENGTH: 5
<212> TYPE: PRT
<213> ORGANISM: Artificial Sequence
<220> FEATURE:
<221> NAME/KEY: UNSURE
<222> LOCATION: (5)
<223> OTHER INFORMATION: Xaa is Arg-p-nitroanilide
<223> OTHER INFORMATION: Description of Artificial Sequence:peptide

<400> SEQUENCE: 15
```

```
Gly Pro Gly Val Xaa
  1             5


<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (5)
<223> OTHER INFORMATION: Xaa is Arg-p-nitroanilide

<400> SEQUENCE: 16

Pro Gly Gly Val Xaa
  1             5


<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (1)
<223> OTHER INFORMATION: Xaa is Boc-Glu(O-t-Bu)
<221> NAME/KEY: UNSURE
<222> LOCATION: (2)..(3)
<223> OTHER INFORMATION: 1 or 2 residues may be missing
<221> NAME/KEY: UNSURE
<222> LOCATION: (5)
<223> OTHER INFORMATION: Xaa is Arg-p-nitroanilide

<400> SEQUENCE: 17

Xaa Gly Gly Val Xaa
  1             5


<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (1)
<223> OTHER INFORMATION: Xaa is Boc-Gly
<221> NAME/KEY: UNSURE
<222> LOCATION: (1)..(3)
<223> OTHER INFORMATION: 1 or more residues may be missing
<221> NAME/KEY: UNSURE
<222> LOCATION: (4)
<223> OTHER INFORMATION: residue may be missing
<221> NAME/KEY: UNSURE
<222> LOCATION: (8)
<223> OTHER INFORMATION: Xaa is Arg-p-nitroanilide
<221> NAME/KEY: UNSURE
<222> LOCATION: (5)..(6)
<223> OTHER INFORMATION: 1 or more residues may be missing

<400> SEQUENCE: 18

Xaa Gly Gly Pro Gly Gly Val Xaa
  1             5


<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (1)..(3)
<223> OTHER INFORMATION: 1 or more residues may be missing
```

-continued

```
<221> NAME/KEY: UNSURE
<222> LOCATION: (4)
<223> OTHER INFORMATION: residue may be missing
<221> NAME/KEY: UNSURE
<222> LOCATION: (5)..(6)
<223> OTHER INFORMATION: 1 or more residues may be missing
<221> NAME/KEY: UNSURE
<222> LOCATION: (8)
<223> OTHER INFORMATION: Xaa is Arg-p-nitroanilide

<400> SEQUENCE: 19

Gly Gly Gly Pro Gly Gly Val Xaa
  1               5


<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (1)
<223> OTHER INFORMATION: Xaa is Boc-Gly
<221> NAME/KEY: UNSURE
<222> LOCATION: (5)
<223> OTHER INFORMATION: Xaa is Arg-p-nitroanilide

<400> SEQUENCE: 20

Xaa Gly Gly Val Xaa
  1               5


<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (1)
<223> OTHER INFORMATION: Xaa is Boc-Gly
<221> NAME/KEY: UNSURE
<222> LOCATION: (5)
<223> OTHER INFORMATION: Xaa is Arg-p-nitroanilide

<400> SEQUENCE: 21

Xaa Pro Gly Val Xaa
  1               5


<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (1)
<223> OTHER INFORMATION: Xaa is Boc-Pro
<221> NAME/KEY: UNSURE
<222> LOCATION: (5)
<223> OTHER INFORMATION: Xaa is Arg-p-nitroanilide

<400> SEQUENCE: 22

Xaa Gly Gly Val Xaa
  1               5


<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence:peptide
```

-continued

```
<221> NAME/KEY: UNSURE
<222> LOCATION: (1)
<223> OTHER INFORMATION: Xaa is Boc-Glu(O-t-Bu)
<221> NAME/KEY: UNSURE
<222> LOCATION: (2)..(4)
<223> OTHER INFORMATION: 1 or more residues may be missing
<221> NAME/KEY: UNSURE
<222> LOCATION: (5)
<223> OTHER INFORMATION: residue may be missing
<221> NAME/KEY: UNSURE
<222> LOCATION: (6)..(7)
<223> OTHER INFORMATION: 1 or more residues may be missing
<221> NAME/KEY: UNSURE
<222> LOCATION: (9)
<223> OTHER INFORMATION: Xaa is Arg-p-nitroanilide

<400> SEQUENCE: 23

Xaa Gly Gly Gly Pro Gly Gly Val Xaa
  1               5


<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence:peptide
<221> NAME/KEY: UNSURE
<222> LOCATION: (5)
<223> OTHER INFORMATION: Xaa is Arg-p-nitroanilide

<400> SEQUENCE: 24

Gly Gly Gly Val Xaa
  1               5


<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence:peptide

<400> SEQUENCE: 25

Ala Asp Ser Gly Glu Gly Asp Phe Leu Ala Glu Gly Gly Gly Val Arg
  1               5                  10                  15

Gly Pro Arg Val Val Glu Arg
             20
```

METHODS OF DETERMINING ENDOGENOUS THROMBIN POTENTIAL (ETP) AND THROMBIN SUBSTRATES FOR USE IN SAID METHODS

This application is the national phase of international application PCT/NL96/00018, filed Jan. 10, 1996.

BACKGROUND OF THE INVENTION

The subject invention lies in the field of thrombosis and haemostasis. In particular the invention is directed at improved chromogenic substrates for thrombin. The substrates according to the invention can be used to great advantage in determination of endogenous thrombin potential. The determination of endogenous thrombin potential and advantages and applications thereof are described in EP appl.nr. 902025097, published on Apr. 3, 1991, publication number 420332 of Hemker et al. The content of said patent is hereby incorporated by reference. The subject invention is also directed at improved methods of ETP determination in a continuous assay.

INTRODUCTION

Thrombin Generation: Its Assessment Via the Endogenous Thrombin Potential

Thrombin is a pivotal element in the complex interplay of vessel wall, blood cells and plasma proteins that ensures haemostasis but also may lead to thrombosis. The mechanisms of prothrombin activation and thrombin inactivation are closely intertwined with functions of the formed elements of blood and blood vessels. The convenient oversimplification of older text books no longer hold: Primary haemostasis and arterial thrombosis are no longer thought to be uniquely platelet functions; secondary haemostasis and venous thrombosis are not the in vivo equivalents of blood coagulation in a tube. Thrombin is the most powerful platelet activator and platelet activation is a prerequisite for normal thrombin formation. The vessel wall carries important parts of the thrombin generation mechanism and periluminal cells carry the tissue factor, the initiator of thrombin generation. The importance of thrombin generation is well illustrated by the fact that all pharmaceutical interventions that decrease thrombin generation (O.A.C., pentasaccharide) or that increase thrombin breakdown (classical heparin, dermatan sulphate) have an antithrombotic action and upon overdosage, cause bleeding. On the other hand all congenital conditions that increase thrombin generation (deficiencies of proteins C and S. APC resistance) or that decrease thrombin breakdown (deficiency of AT III) will cause a thrombotic tendency.

In view of the central role of thrombin it is important to be able to assess the thrombin generating capacity of a plasma sample in a single, global function test; i.e. express the resultant of the thrombin-forming and thrombin-breakdown mechanisms in one parameter. This figure would show a decrease upon hypocoagulation of any kind and an increase in hypercoagulability. For more than a century clotting times have been used for this purpose, but they are not sensitive to hypercoagulation, not very sensitive to moderate coagulation defects and sometimes insensitive to anticoagulant measures (PT to heparin: PT and APTT to low molecular weight heparins). This is mainly because clotting is an early event during the process of thrombin generation. At the moment a plasma sample clots, the large majority (>95%) of thrombin still has to be generated and variations in this process are not reflected in the clotting time. In the APTT the lag time of thrombin formation is mainly dependent upon the feedback activation of factor VIII, which in itself is a function of thrombin generation, which is why this test is the best one available at this moment to measure e.g. the heparin effect.

As a parameter that reflects the whole of the thrombin generation process the Endogenous Thrombin Potential (ETP) i.e. the area under the thrombin generation curve has been proposed. ETP is indeed an indicator of the potency of the clotting mechanism.

The potency of thrombin generation should not be confounded with the extent of ongoing thrombin generation in the body. Fragments 1, 2 of prothrombin and TAT-complexes reflect how much thrombin is generated in the body and subsequently inactivated. They are like smoke detectors reporting an ongoing fire. A test for hypo- of hypercoagulability however should indicate the potential capacities of the non-triggered system. In D.I.C. with consumption coagulopathy the indicators of ongoing coagulation are high but the capacity of the plasma to generate thrombin is low. In congenital AT III deficiency the reverse is the case.

The Mechanism of Thrombin Generation

The mechanism of thrombin generation is governed by three different kind of processes, the three "axes" of thrombin formation:

a) Thrombin production and inactivation in the strict sense of the word, b) Modulations of the thrombin generation velocity and c) Localisation at the site of vascular damage.

These three axes are best illustrated in the prothrombinase complex. The production of thrombin from prothrombin is caused by factor Xa, the availability of factor Va determines the velocity of thrombin generation and the process is localised at the surface of a procoagulant membrane.

The core of the thrombin generation mechanism is the production-inactivation axis: Tissue factor activates factor X, which activates prothrombin. The resulting thrombin is inactivated by antithrombin and minor inhibitors. The production along the axis is limited in time by the TFPI mechanism. When a sufficient amount of factor Xa is formed, the Xa generation is shut down because of formation of Xa-TFPI complexes that efficiently inhibits the factor VIIa-tissue factor complexes. To prevent precocious arrest of thrombin formation via the TFPI mechanism, the Josso Loop constitutes an escape mechanism: Factor IX is activated by the factor VIIa-TF complex like factor X is. Together with factor VIIIa it forms an alternative factor X activator that is not inhibited by TFPI but the activity of which is modulated by factor VIII activation and inactivation, a process entirely comparable to the modulation of prothrombinase activity by factor V(a). The second axis is modulation of thrombin generation via factor V activator and inactivation. Factor Va enhances the turnover of prothrombin by factor Xa some thousand fold. The appearance and disappearance of factor Xa is governed by thrombin. Factor Xa has been shown to activate factor V in purified systems but not in plasma. The natural activator of factor V in a tissue factor activated system is probably meizothrombin. This can i.a. be deduced from the fact that the thromboplastin time is relatively insensitive to heparin, meizothrombin being insensitive to AT III—heparin action. The inactivation of factor V is indirectly thrombin dependent because the scavenger of factor Va, activated protein C, is generated by the thrombomodulin-thrombin complex.

Factor VIII governs factor IXa dependent generation of factor Xa in the same way factor V governs prothrombinase activity. A difference is that factor V is probably activated by meizothrombin at a phospholipid surface whereas factor VIII is kept in solution by von Willebrand factor and is activated by thrombin.

The third axis of thrombin generation is localisation. Upon loss of endothelial integrity, platelets adhere to the subendothelial material. Cell damage exposes first traces of procoagulant (PS containing) membranes and Tissue Factor starts the coagulation cascade. As soon as traces of thrombin are formed, the simultaneous action of thrombin and collagen induces transbilayer movement of PS in the platelet membrane and the platelet surface becomes procoagulant. The procoagulant action of PS containing membranes is due to the fact that clotting factors adsorb to these surfaces. This increases the effective concentration of the reactants. It has been shown e.g. that prothrombin adsorbs at such surfaces and then, by diffusion in the plane of the surface, reaches the prothrombinase complex. Because the chance for prothrombinase and prothrombin to meet is much bigger in two dimensions than in three, this mechanism "guides" prothrombin to prothrombinase. The extent of the procoagulant surface around a prothrombinase molecule has indeed been shown to determine the apparent Km of prothrombin conversion, i.e. the concentration of prothrombin in solution necessary to half-saturate prothrombinase.

The whole of thrombin generation is so replete with positive and negative feedback mechanisms that its kinetics will show a strongly non-linear behaviour. Small changes in one or more of the constituent activities may therefore have unexpected effects on the output. This precludes that any of the isolated functions within the mechanism will be an adequate reflection of the whole. In order to measure the thrombin generation mechanism one has to measure thrombin.

The Thrombin Potential

We can imagine that in a thrombosis-prone area the number of substrate molecules (fibrinogen molecules, membrane receptors etc.) that is cleaved by thrombin determines the extent of the thrombotic response. This number will be dependent upon the concentration of thrombin that can be produced by the plasma in situ and by the time that they remain active. If the substrate is not exhausted (which fibrinogen e.g. easily is) then the number of molecules converted is proportional to both thrombin concentration and the time thrombin acts. If the thrombin-time curve is rising and falling, as in plasma, then the amount of non-exhaustible substrate converted is proportional to the surface under the thrombin-time curve.

In vivo physical transport processes like flow and diffusion also determine local thrombin concentrations. This implies that the thrombin generating capacity of plasma is not the only important variable. On the other hand, if by biochemical mechanisms high thrombin concentrations arise at one point the high thrombin concentrations will also be observed around that site, as thrombin is transported by diffusion etc. So the thrombin generation capacity remains an important parameter for the functioning of the system.

We conclude that the surface under the thrombin-time curve is the parameter that best renders the thrombin generating capacity of a plasma sample. This value we called endogenous thrombin potential (ETP). As such it is not a new parameter, it has been described by Biggs and Macfarlane and was used by them to determine prothrombin levels, for which it is perfectly suited as long as activation and inactivation mechanisms in a plasma do not vary (see below). The use we want to make of it here is different. We do not attempt to keep activation and inactivation mechanisms constant but rather want to register the influences on thrombin activity.

In summary: We define the ETP as the surface under the thrombin generation curve (thrombin-time curve triggered plasma); the reason to think that it is an important parameter is that it represents the amount of any substrate that can be converted by the thrombin generated in the plasma sample tested.

How to Measure the Endogenous Thrombin Potential

In principle it is easy to measure the ETP. It suffices to add to clotting plasma an artificial thrombin substrate and determine the amount of produce formed after the coagulation process is over.

There are some practical problems though. The first choice is a chromogenic substrate, so that the amount of product can be determined spectrophotometrically. The fibrin forming in clotting plasma interferes with direct spectroscopic observation however. This imposes previous defibrination of the sample.

The properties that the substrate should have are uncommon. It should be specific for thrombin. If it were to be cleaved significantly by other clotting enzymes the signal would rise somewhat but, in view of the low concentrations of these other clotting factors this may remain a minor problem. Such a substrate would however act as a competitor to the natural substrates and hence inhibit prothrombin conversion. This substrate should also not be exhausted during the coagulation process and preferably not be converted to an extent of >10%, otherwise substrate exhaustion would significantly interfere and the amount of product formed would no longer be linearly proportional to the surface under the T.G.C. (thrombin generation curve). It is seen that, after the thrombin generation process is over, there is continuous product generation. This is due to thrombin that is bound to a2 macroglobulin (a2 M). Such thrombin has a persistent amidolytic activity, even though it is not active on any natural thrombin substrate.

Via a simple mathematical procedure the experimental curves can be dissected.

Properties of the Normal E.T.P.

The ETP in normal individuals has a value of 543±21 nM min. (as the ETP represents a surface on the concentration-time plane its dimensions are concentration multiplied by time, both nM min or $\mu$M sec. are convenient). The ETP is hardly dependent upon the concentrations of thromboplastin used. We prefer to measure the ETP after triggering with dilute recombinant human tissue factor because we think this to be nearest to the physiological situation. It is interesting to note that a moderate decrease of the extrinsically triggered ETP is observed in haemophiliacs A. Triggering the ETP via the contact activation mechanism is equally possible.

The ETP in Hypocoagulant Therapy

In heparin therapy the ETP decreases proportionally with the decay constant of thrombin, whereas the effect of inhibition of factor Xa is also reflected. It is observed that the ETP is much more sensitive to low concentration of heparin than the APTT. Indeed the ETP is the only laboratory parameter with which an effect of blood coagulation can be observed after injection of LMW Heparin.

In oral anticoagulation the ETP is linearly dependent upon the concentration of prothrombin, which reflects an observation of Biggs and Macfarlane and explains its use, of old, as a prothrombin assay. The ETP is dependent upon the concentration of the other vitamin K dependent factors in a hyperbolic manner. Half-normal ETP values are observed at the following clotting factor concentrations: FVIII: 2%; FIX: 5%; FX: 10%.

It is interesting to note that, when switching from heparin therapy to oral anticoagulatin, the ETP, unlike PT, APTT and aXa, seems to render the level of the mixed treatment.

The ETP in Hypercoagulant States

The limited data that are available up to this moment show that ETP is increased both in congenital and in acquired hypercoagulant states. In patients that are hospitalised with an active venous thrombosis, the ETP is prolonged when compared to comparable patients that are seen for elective vascular surgery. At the moment it is unknown whether this is due to the active process or to a pre-existing thrombotic tendency. In a limited number of young stroke patients the ETP in PPP (platelet poor plasma) was not significantly increased, but the ETP in PRP (platelet rich plasma) was. Further studies are needed to sort these situations out. There is no doubt that in the presence of thrombomodulin the ETP of normal subjects decreases more than that of patients with a protein S or more protein C deficiency. It also has been observed that APC resistance is readily detected by comparing the ETP of patients in the presence and absence of added APC. A simple trick has been reported that can be used to indicate the influence of a vitro addition on the thrombin potential: Because $\alpha_2$ macroglobulin (2–3 $\mu$M) is present in excess over thrombin during the whole of thrombin (<300 nM) generation process, the amount of $\alpha_2$-thrombin complex formed is in itself an indication of the ETP. It cannot however be used to compare the ETP between patients because the $\alpha_2$-M level may vary from person to person. It can however be easily used to compare the ETP in the same plasma with and without addition of modifying substances such as thrombomodulin (to search for protein C and S deficiency) or APC (to search for APC resistance). This technique can also be employed to investigate the influence of in vitro additions of anticoagulant on the ETP.

In Conclusion We May Say That a) The function of thrombin in haemostasis and thrombosis is important enough to justify the desire to know the thrombin forming capacity of a plasma sample.

b) The non-linear character of the thrombin generation mechanism precludes the possibility that the thrombin forming capacity of plasma can be judged from the activity of one of its single components.

c) Clotting times are imperfect indicators of the thrombin forming capacity of a plasma sample. They do not reflect the whole of thrombin generation process and they are insensitive to hypercoagulative changes.

d) The endogenous thrombin potential (ETP), i.e. the area under the thrombin generation curve can be considered to be the parameter that best reflects the thrombin forming capacity of a plasma sample.

e) Preliminary results indicate that the ETP is diminished under all forms of anticoagulant therapy.

f) The ETP is increased in all hypercoagulable states that we have tested thus far, notably congenital states (AT III, protein C, protein S deficiency) and acquired states (e.g. oral anticonceptives).

g) A method has been found to determine the ETP in the routine laboratory.

SUMMARY OF THE INVENTION

When the endogenous thrombin potential is measured in a manner known per se as described in the abovementioned European patent of Hemker et al. in a continuous procedure using paranitroaniline (=pNA) as an indicator there is a lower limit beneath which the current substrates cannot reliably provide measurements. This lower limit is determined by the amount of pNA that can be reliably measured against the yellow background colour always present in plasma. The lower limit varies somewhat in exact value due to variation in the optical density of plasma itself. As a rule however the lower limit is not lower than 5 mOD.

The substrate currently used and favoured in the continuous assay of ETP is SQ68. SQ68 is $CH_3O$—CO—$CH_2$—CO-Aib-Arg-pNA.HCl and is described in EP-B-0 280 610 of Serbio published on Aug. 31, 1988 and granted Oct. 21, 1992. Use of SQ68 in the continuous assay of ETP in particular without requiring addition of either ATIII or HCII is described in by Hemker H.C et al. (1993) in Thromb. Haemostas. 70, p. 617–624.

The jump in optical density of plasma comprising SQ68 at the end of the ETP assay that is obtained when ETP is measured under optimal conditions using SQ68 as a substrate is in the order of 100 mOD. This means that values of ETP that are about 5% of the normal value of ETP cannot reliably be measured when carrying out a continuous assay of ETP in the manner described.

The lower acceptable limit of anticoagulation has been determined as being around an ETP of approximately 5%. This value is valid whether anticoagulation is arrived at orally or with heparin. This means that use of SQ68 or substrates with equivalent characteristics leads to a lower detection limit which more or less coincides with the lower limit of acceptable anticoagulation. As a result the continuous determination of ETP using SQ68 may sometimes be insufficiently sensitive to accurately indicate over-anticoagulation with all potentially detrimental consequences for the donor of the sample being tested.

In particular SQ68 or substrates with equivalent characteristics are not suitable for use in a continuous assay of ETP of a sample when said sample comprises too high a concentration of oral anticoagulant or in particular heparin. SQ68 can only be used in a continuous assay for ETP determination when the sample comprises less anticoagulant activity than that due to 0.7 International Standard Units of heparin. This is due to the fact that oral anticoagulants and in particular heparin reduce the amount of thrombin in the sample. In order for detection to occur the substrate must provide a detectable signal when a sample comprises such lower amounts of thrombin.

The invention lies in the designing of chromogenic substrates for thrombin that can be used for ETP measurements of samples comprising oral anticoagulant and in particular heparin in a continuous assay thereby solving the above outlined problem presented by the state of the art substrates. More in particular the invention is directed at methods for determining ETP that are improved.

A substrate according to the invention is subject to a number of restrictions in order to be effective. Apart from the aforementioned necessary characteristics a number of other preconditions must be fulfilled.

For use in a continuous assay of endogenous thrombin potential by measuring a continuous optical density curve there is a need for substrates with modified kinetic parameters. The chromogenic substrate present in the plasma sample interferes competitively with the physiological substrates of thrombin and thus affects the physiological steady state. To minimize competitive inhibition processes the Km value of the synthetic substrate for thrombin should be high. To prevent this substrate from being exhausted long before thrombin generation is complete however a slow reacting substrate has to be used. This means that the turnover lcat of this synthetic substrate has to be low. The substrate should not interfere but merely monitor the course of the steady state concentration and time.

The requirements for a synthetic substrate to be useful in the continuous ETP method are:

1) the substrate must be selective for thrombin with a high Km and low lcat value, 2) as the process of thrombin generation takes place in a plasma sample the chromogenic substrate must preferably be free of any inhibitory activity on the coagulation factors which affect the formation of thrombin, 3) to minimize additional amidolytic activity by Factor Xa the substrate must have a low affinity for Factor Xa and thus have low lcat and high Km values towards Factor Xa, 4) as the complex of α2-macroglobulin-thrombin has no clotting properties but does have amidolytic activity the chromogenic substrate should have low affinity for this complex.

Research into substrates for thrombin has been extensive and to date tailoring substrates to specifically desired characteristics has remained very elusive. Often amendment improving one characteristic will lead to undesirable alteration of other characteristics.

In the subject case for example providing sufficient solubility in an aqueous solution has been difficult as this often leads to substrates having a concomitant decrease in selectivity towards thrombin. The sufficient selectivity is essential in the subject application for which the substrates are preferably to be used in order to achieve accuracy of determination.

The substrates according to the invention need to exhibit exceedingly high solubility in plasma and blood i.e. in aqueous solutions in order for sufficient substrate to be added for the continuous ETP assay to be carried out without running out of substrate prior to the exhaustion of thrombin in the sample to be determined i.e. prior to reaching the end of the ETP curve. In particular the substrate needs to be soluble preferably in amounts such that 500–1000 μM substrate remains at the end of the determination of the ETP curve. In practice this means solubility sufficient for the initial concentration of substrate in an aqueous solution such as plasma for example to be higher than 10 mM.

Another problem has been the fact that amendments to ensure lower hydrolytic activity towards thrombin have often negatively influenced the desired characteristics towards Factor Xa and other components in the coagulation cascade. In particular often hydrolysis by Factor Xa has increased intolerably.

When designing a substrate for use in a continuous ETP assay the specificity for thrombin is of utmost importance. A person skilled in the art would therefore try to mimic a natural substrate that has specificity for thrombin. In particular the binding site specific for thrombin of such a substrate could be expected to provide relevant information.

A lot of research has gone on for quite some time regarding this issue. Articles from 1967 already deal with the determination of the binding site for thrombin on fibrinogen and development of specific substrates therefor.

Fibrinogen is the natural substrate of thrombin. It is a covalently linked dimer of three peptide chains: Aα Bβ and γ. The general structure can be given by (AαBβγ)2. (Henschen et al. (1980) Ann. N.Y. Acad. Sci. 408, 28–43). Thrombin catalyzes hydrolysis of peptide bonds involving the carboxyl group of arginine; in fibrinogen Arg 16 (Aα-chain) and Arg 14 (Bβ-chain) are attacked releasing the fibrinopeptides A and B respectively and leaving the fibrin monomer $(\alpha\beta\gamma)_2$. This monomer polymerizes which results in the formation of the bloodclot.

The cleavage of fibrinogen by thrombin is highly specific since only four Arg-Xaa or Lys-Xaa bonds of the 376 present will be hydrolyzed (Blombäck et al., (1967) Nature 215, 1445–1448). This remarkable specificity is confined to the N-terminal henpentacontapeptide fragment of the Aα-chain ((a) Hageman et al. (1974) Arch. Biochem. Biophys. 164, 707–715; (b) Hogg et al. (1974) Thromb. Res. 5, 685–693). In this region fragment 1–23 (sequence id no. 1) which also contains these combinations interacts with the active site and is most important for the observed specificity. (Hogg et al. (1978) Thromb. Res. 12, 953–964). It was found that the amino acyl residues located at the C terminal of Pro 18 do not contribute substantially in the binding to thrombin (Meinwald et al. (1980) Biochemistry 19, 3820–3825).

Angliker H. et al (Biochem J. (1993), 292: pp 261–266) describe synthesis of oligopeptide chloromethanes to investigate extended binding regions of proteinases and in particular the application thereof to the interaction of fibrinogen with thrombin. As peptidyl chloromethanes are inactivators of serine and cysteine proteinases and the peptide portion of these reagents direct them to the active site of their target proteinase variation of their amino acid residues has enabled mapping of a number of binding sites.

They indicate that past studies have been restricted to use of di- and tripeptidyl chloromethanes due to the length of peptide moiety that can be conveniently synthesized by solution phase chemistry but indicate this is often not sufficient as some proteinases appear to interact with regions of their substrates that extend more than three residues away from the scissile bond. According to Angliker et al thrombin is such a proteinase.

They concluded from their experiments with extended chloromethanes that residues Asp 7-Phe 8-Leu 9 of fibrinopeptide A are important for the specific interaction with thrombin. The hydrophobic interactions with the D-phenylalanine in the P3 position are probably responsible for the increased rate of reaction. Intermolecular contacts apparently stabilizing chain reversal at Ala 10 and the positioning of the side chain of Glu 11 are undoubtedly important. In addition Phe 8 and Leu 9 bind to the hydrophobic aryl binding site. This site was discussed as the binding site for the D-Phenylalanine of D-Phe-Pro-Arg-$CH_2Cl$, however Phe 8 and Leu 9 enter the pocket from a different angle due to the chain reversal and occupy the site more fully.

They specifically state Ac-Gly-Val-Arg-$CH_2Cl$ was a relatively poor inactivator of thrombin; the $k_i$ value for this compound was $3\times10^4$ times lower than that for the best known chloromethane tripeptide inhibitor of thrombin which was D-Phe-Pro-Arg-$CH_2Cl$.

It can be concluded from this that dipeptide and tripeptide substrates specific for thrombin are going to be difficult if not impossible to design. Certainly as in addition other characteristics are also required for substrates suitable for use in a continuous ETP assay the design of substrates for thrombin suitable for such use is to be considered an arduous and perhaps even impossible task.

Van Nispen demonstrated earlier that the presence of residues Phe 8 and Leu 9 greatly enhances the rate of catalytic hydrolysis of the Arg 16-Gly 17 bond by thrombin. ((a) van Nispen et al. (1977) Arch Biochem. Biophys. 182, 227–243; (b) Marsh et al. (1982) Biochemistry 21, 6167–6171). They illustrated that the addition of the non-polar residues phenylalanine and leucine to Ala-Glu-Gly-Gly-Gly-Val-Arg-Gly-Pro-Arg-Val-Val-Glu-Arg-NHCH3 (SEQ ID NO:1) causes a dramatic increase in the rate of hydrolysis of this substrate and referred to the findings of Blomback B. et al (1967) in Blood Clotting Enzymology (Seegers, W. H. ed.) pp 143–215 Academic Press New York. In this reference the importance for phenylalanine was already suggested on the basis of the extreme degree of conservation of Phe 9 in 49 species of fibrinogen that were examined.

Van Nispen et al also refer to Svendsen et al (Thromb. res. 1, 267–278) who demonstrated the importance of hydrophobic interactions between thrombin and synthetic substrates therefore. Benzoyl-Phe-Val-Arg-p-nitroanilide has a value $90\times10^{-7}$ [(NIH units/liter)s]$^{-1}$ for $k_{cat}/K_m$. The substrates H-Phe-Val-Arg-p-nitroanilide, benzoyl-Val-Arg-p-nitroanilide and H-Val-Arg-p-nitroanilide were poorer substrates for thrombin by at least a factor of 100. The hydrophobic combination of benzoyl-Phe was required for a high rate of hydrolysis in these substrates.

DETAILED DESCRIPTION OF THE INVENTION

Quite unexpectedly we have designed a number of substrates that are extremely well suited for use as substrate specific for thrombin in continuous assays for ETP determination. In particular the substrates are suited for carrying out the assays described in EP appl.no. 902025097 and for carrying out an assay as described in Hemker et al. (1993) in Thromb. Haemostas. 70 p 617–624. The substrates according to the invention provide the exciting possibility of determining ETP of samples with values of heparin activity and/or other anticoagulant activity previously not possible.

The first type of substrate found to exhibit the required characteristics was a dipeptide substrate comprising the formula P-Val-Xaa-S, wherein

- P is an amino protective group, said group being non aromatic and polar,
- Val is a valine residue attached via a peptide bond to Xaa,
- Xaa is an amino acid residue comprising a terminal guanidino group or ureido group separated by at least 2 carbon atoms from the peptide backbone, said amino acid residue being attached to S,
- S is a signal group such as a chromophore that can be enzymatically hydrolysed with the proviso the substrate is not $CH_3O$—CO—$CH_2$—CO-L-Val-Arg-pNA.

P is preferably an organic moiety. More preferably an organic moiety exhibiting interaction with the aryl binding pocket of thrombin. The P group preferably fits in the aryl binding pocket of thrombin. Msc, $CH_3$—$SO_2$—$CH_2$—$CH_2$—O—CO— (methylsulphonylethyloxycarbonyl) has been found to be an extremely effective protective group. Msc is a preferred protective group which does not detract from the specificity of the substrate for thrombin and concomitantly renders the substrate sufficiently soluble for application in a continuous assay for determination of ETP of a sample comprising heparin or other anticoagulant activity at a level higher than the equivalent of 0.07 U ISH/ml. The presence of Msc as protective group of Valine does not affect the coagulation cascade as determined from analysis of the prothrombinase activity.

We have also found that H as such is also sufficient as P to provide the desired characteristics for a substrate to be used in a continuous assay of ETP to suitable degree. However such substrates e.g. H-Val-Arg-pNA exhibit an undesired inhibitory effect making them less suitable than substrates with organic protective groups such as Msc which do not exhibit an inhibitory effect. The decay constants of thrombin in plasma in the presence of the substrate H-Val-Arg-pNA show a slighter drop than in the case of the state of the art substrate SQ68. The substrate according to the invention competes to a lesser degree with ATIII for the active site of thrombin than SQ68 does.

When the influence of H-Val-Arg-pNA on the prothrombinase complex is calculated the substrate clearly decreases its concentration (FIG. 1). This was also seen for SQ68. Presumably the feed back loop activation of Factor V and factor VIII by thrombin is inhibited in the presence of H-Val-Arg-pNA. The $K_m$ value and the high substrate concentration result in a substantial decrease of thrombin which is available for the activation of Factor V and factor VIII with a lag phase in prothrombinase concentration as a result. H-Val-Arg-pNA can be used for ETP determination with a heparin activity of 0.10–0.15 U ISH/ml.

As disclosed in the introductory portion of the description, SQ68 has been used in ETP determinations in continuous assays. SQ68 is $CH_3O$—CO—$CH_2$—CO-Aib-Arg-pNA.HCl and is described in EP-B-0 280 610 of Serbio published on Aug. 31, 1988 and granted Oct. 21, 1992. Aib represents α-aminoisobutyric acid (=α-methylalanine). The cited patent is not directed at solving the subject problem. At the time of filing the Serbio application the method of ETP determination had not in fact even been invented.

In the cited patent SQ68 was illustrated merely as one of a large number of substrates that can be used for determining the amount of a protease from class E.C. 3.4.21.5, the class of serine proteases covering a number of proteases such as thrombin, plasmin, factor Xa and protein C. The cited patent describes in general terms a group of dipeptide substrates having increased water solubility due to the presence of a particular type of protective group Q.

The Serbio patent claims dipeptides of the formula Q—A1—A2—R1, wherein Q is an oxymalonyl group RO—CO—$CH_2$—CO, R represents a hydrogen atom. a $C_1$–$C_4$ alkyl group, a phenyl group optionally substituted by one or more $CH_3$ and $OCH_3$ groups, a 3.4 methylenedioxybenzyl group or a tosylmethyl group; R1 is an amino radical of formula NH—R' constituting a marker cleavable by enzymatic hyrolysis from A2 with the group R' serving as carrier for the labeling means; A1 is a mono amino acid residue selected from non basic amino acid residues; A2 is a mono amino acid residue selected from the group of basic α-amino acids and the addition salts thereof.

A preference is expressed for R=$CH_3$. Compounds wherein Q=pNA are also preferred embodiments, as are compounds $CH_3O$—CO—$CH_2$—CO-L-4Hyp-L-Arg-pNA and $CH_3O$—CO—$CH_2$—CO-L-Pro-L-Arg-pNA-CO-L-Pro-L-Arg-pNA (SEQ ID NO:2) which are described as illustrating higher sensitivity towards protein C than other substrates. Nothing is stated regarding substrates having selectivity for thrombin in plasma, i.e. selectively reacting with thrombin rather than Factor Xa. Nothing is disclosed regarding design of a dipeptide substrate specific for thrombin.

Rates of hydrolysis for 16 substrates are given in solutions comprising solely thrombin, Factor Xa, plasmin or protein C. The 16 examples all comprise Arg as A2 and $CH_3O$—CO—$CH_2$—CO as Q. A1 is different for each example. The preferred substrates of the Serbio application are $CH_3O$—CO—$CH_2$—CO-L-4Hyp-L-Arg-pNA with rates of hydrolysis for thrombin, Factor Xa, plasmin and protein C of respectively 0.61, 0.34, 1.12, 0.88 for this substrate and $CH_3O$—CO—$CH_2$—CO-L-Pro-L-Arg-pNA with rates of hydrolysis for thrombin, Factor Xa, plasmin and protein C are respectively 0.68, 0.14, 0.230, 0.83 for this substrate.

As stated above SQ68, $CH_3O$—CO—$CH_2$—CO-Aib-Arg-pNA.HCl is one of the Examples of the Serbio patent. The rates of hydrolysis given in the patent for thrombin, Factor Xa, plasmin and protein C are respectively 0.04, 0.01, 0.02, 0.03 for this substrate. No significance was attached to any of these details in the Serbio patent.

By way of comparison the state of the art compound SQ68 that to date has been used in ETP determination in a continuous assay can only reliably be carried out on a sample comprising at most 0.07 U ISH/ml activity. The substrate Msc-Val-Arg-pNA for example can be used reliably on samples comprising up to 0.25 U ISH/ml activity. In addition this substrate according to the invention can provide a signal which is twice as high as that produced by SQ68 which enables values of up to 2.5% of the normal value of plasma to be determined as the limit of reliable detectability as opposed to 5% for SQ68. This lower limit of 2.5% is well below the lower limit of acceptable anticoagulation, thereby rendering a continuous assay of ETP using such a substrate or another substrate according to the invention sufficiently sensitive to indicate with reliable detectability over anticoagulation.

Another advantage of the substrate according to the invention is that its $K_m$ for Factor Xa is almost double that of SQ68 (9.6 mM versus 3.9 mM). This fact means that the concentration of substrate according to the invention that can be used in practice without inhibiting Factor Xa in prothrombinase is also more than double that of SQ68 i.e. is more than 1000 $\mu$M.

The Serbio patent also discloses and covers a substrate comprising a polar non aromatic organic protective group attached to L-valine-arginine-pNA. The substrate is $CH_3O$—CO—$CH_2$—CO-L-Val-Arg-pNA. Nothing is mentioned specifically with regard to advantages or characteristics of this substrate. The rates of hydrolysis for thrombin, Factor Xa, plasmin and protein C are respectively 0.21, 0.03, 0.08, 0.12 for this substrate.

The totally unexpected influence of the selection of Valine-Xaa as defined above, in particular Valine-Arginine as essential combination of amino acid residues in a dipeptide substrate of the subject invention can be derived neither from the Hemker H.C. et al. (1993) Thromb. Haemostas. 70, p. 617–624 nor the Serbio patent. The group of substrates that are novel and inventive is defined as a dipeptide substrate comprising the formula P-Val-Xaa-S, wherein P is an amino protective group, said group being non aromatic and polar, Val is a valine residue attached via a peptide bond to Xaa, Xaa is an amino acid residue comprising a terminal guanidino group or ureido group separated by at least 2 carbon atoms from the peptide backbone, said amino acid residue being attached to S, S is a signal group such as a chromophore that can be enzymatically hydrolysed with the proviso that the substrate is not $CH_3O$—CO—$CH_2$—CO-L-Val-Arg-pNA or H-Val-Arg-pNA. In other words not a substrate as disclosed and claimed in the Serbio patent or in the Svendsen et al article Thromb. res. 1, 267–278 described above.

That the combination of valine with Xaa of the above defined type is very specific for obtaining the desired characteristics is apparent from comparative analysis of substrates in which natural amino acid residues that are structurally relatively close to arginine have been compared to the substrate according to the invention wherein Xaa is arginine. When Xaa was Lys, Orn or Nle the substrates did not provide the unexpectedly good results of the above mentioned group of substrates according to the invention.

It is quite surprising that although a combination of Valine-Arginine provides good results a combination of Valine-Lysine does not provide good results.

Analysis of Table 3 would lead a person skilled in the art to presume that lysine would be a better choice of amino acid than arginine in a substrate for the specific purpose in mind due to the fact that factor Xa hardly hydrolyzes substrates with a lysine residue at position P1 in contrast to thrombin. In practice however this is not the case for the dipeptide substrates comprising valine as N-terminal amino acid residue. Substitution of arginine by lysine in H-Val-Arg-pNA provided a substrate that could not be recognised by either thrombin or factor Xa. Evidently the S2 cavity of thrombin no longer recognizes such a substrate. Substitution of any of norleucine, ornithine or lysine resulted in amino protected valine comprising dipeptidyl substrates for thrombin that did not possess the desired characteristics. Ornithine and Norleucine substituted substrates no longer hydrolysed thrombin.

Comparison of the amino acid structures reveals arginine has a spherical charge due to the presence of a guanidino moiety. Norleucine has no guanidino group and has a hydrophobic aliphatic neutral side chain. Norleucine also has a shorter side chain with 4 C atoms as opposed to arginine which has 4 C atoms and 2 N atoms.

Ornithine has a shorter side chain with only 3 C atoms and 1 terminal $NH_2$ group. This amino acid is not spherically charged. It does not have a guanidino moiety.

Lysine has a charged side chain, however the charge is not spherical. The side chain comprises 5 C atoms and 1 N atom. It comprises a terminal $NH_2$ group but does not comprise a guanidino moiety as opposed to arginine. The results are provided in Table 3.

From these results it is apparent that the interaction of Msc as P with the aryl binding pocket of thrombin did not result in hydrolytic cleavage of the anilide bond when the P1 residue differs from Xaa as previously defined, in particular when Xaa was Arginine.

As the substrates according to the invention described above comprise merely two amino acid residues it is presumed that arginine provides the primary recognition. Such a small peptidyl portion being capable of providing highly specific recognition of thrombin is unexpected. The fit in the pocket must be very good. The valine residue probably provides the selectivity for thrombin over Factor Xa. The characteristics of the substrate can then be further enhanced through selection of a suitable protective group P. A preferred group P will not result in lower selectivity for thrombin over Factor Xa. This latter aspect was purported to occur when substrates for thrombin were protected by a polar group. However we have found that in the substrates in which valine is combined with arginine or a similar amino acid residue the protective group P of valine can be a polar group as the Val-Arg provides sufficient selectivity. A preferred group P will result in a substrate still selective for thrombin whilst having as high a solubility as possible.

We presume the presence of a guanidinolike structure on the arginine amino acid residue probably due to the provision of a spherical charge is required for obtaining the desired characteristics of a substrate according to the invention. The length of the side chain can also be considered a relevant factor. Preferably a side chain equal to or more preferably longer than that of ornithine is required in order for hydrolysis of thrombin to occur.

We could thus determine that substrates according to the invention could also be P-Val-Xaa-S wherein P, Val and S have the meaning previously given and Xaa is an amino acid residue comprising a terminal guanidino group with at least two carbon atoms separating the guanidino group from the peptide backbone. For example the substrate can comprise norarginine as arginine derivative comprising $CH_2$—$CH_2$ between the guanidino group and the peptide backbone or homoarginine comprising $CH_2$—$CH_2$—$CH_2$—$CH_2$ between the guanidino group and the peptide backbone. Thus slightly altering the length of the chain, without altering the guanidino structure. Alternatively the guanidinogroup and the peptide backbone may be separated by $CH_2$—O—$CH_2$ or $CH_2$—S—$CH_2$. Another option is that the guanidinogroup and the peptide backbone are separated by $CH_2$-phenyl or $CH_2$-cyclohexyl, with the phenyl or cyclohexyl optionally being substituted. Preferably any difference in the composition of the amino acid side chain located between the peptide backbone and the guanidino moiety at the end of the side chain will mimic the characteristics of the corresponding part of arginine most closely. A person skilled in the art should be able to determine which modifications can be acceptable for fitting the S2 cavity of thrombin whilst not being suitable for hydrolysis by factor Xa. A number of thrombin inhibitors have been illustrated to inhibit thrombin better than Xa when aromatic side chains were used for binding the equivalent pocket, thereby indicating that an amino acid Xaa with an aromatic group could provide sufficient recognition of thrombin over Xa.

Any of the above mentioned substrates P-Val-Xaa-S may also comprise an Xaa with an uramino group instead of a guanidino group. Both groups possess similar structure. They possess a spherical charge distribution and can undergo similar binding interactions and have a similar size. Citrullin would be a suitable example as its chain length is approximately that of arginine with 4 C atoms and 2 N atoms. The only difference in the side chain structure being the presence of C═O rather than C═NH.

Most preferably the length of the side chain of Xaa will be longer than that of ornithine, preferably longer than that of lysine and most preferably correspond to that of the side chain of arginine, thereby mimicing the structure of arginine the closest. The Xaa will comprise a spherical charge preferably due to the presence of a guanidino moiety thereby most closely mimicing the structure of arginine.

The Xaa comprising guanidinophenyl or guanidinocyclohexyl are not commercially available and therefore their synthesis will be quite complicated. Preparation of a substrate according to the invention comprising citrullin will involve less work as citrullin is commercially available and will therefore be preferred. However the synthesis of such a substrate according to the invention will still remain quite complex. A person skilled in the art of peptide chemistry can however using standard synthesis techniques prepare such substrates. Obviously the more simple synthesis methods or at least cheapest methods will be preferred.

A number of other substrates according to the invention mentioned above comprising commercially available components, in particular for example Msc-Val-Arg-pNA can be very elegantly and simply synthesized. This simple method of production of the substrates according to the invention offers a further advantage over substrates such as SQ68 which are synthesized as described in the Serbio patent cited above.

The subject invention is in particular also directed at a method of synthesis of substrates according to the invention as described above wherein S is pNA. It is directed at a novel method of synthesis of H-Val-Arg-pNA. It is directed at a novel method of synthesis of Msc-Val-Arg-pNa as this can be carried out as a one step method, with obvious advantages.

Syntheses with nitroanilides are incompatible with conditions which attack or remove the nitroanilide function. This means that treatments using strong bases for hydrolysis or β-elimination, hydrazinolysis and catalytic hydrogenolysis cannot be employed in a method of substrate synthesis if the substrate comprises a nitroanilide signalmarker S. The protective functions used in the synthesis of the substrates must be removable under conditions that are compatible with conservation of the pNA moiety. This precondition means that $OCH_3$ and OEt cannot be used for carboxyl group protection, carboxylic functions cannot be preactivated with hydrazine hydrate and most members of the benzyl family cannot be applied. Furthermore when P of the substrate to be synthesized is Msc, then Msc cannot be used in amino protection in the method of synthesis. Acidolysis is an acceptable form of treatment compatible with conservation of the nitroanilide function.

It is also risky to convert existing peptides into nitroanilides. This is due to the strict conservation of the chirality of amino acyl residues which excludes the activation of N-protected peptides with C-termini other than Gly or Pro.

Synthesis approaches which are compatible with this condition are stepwise elongation of the peptide chain using N-protected amino acids and/or fragment condensation using azides to acylate an existing amino acid paranitroanilide. Azides are often used to evade racemisation during fragment condensations on condition that neutral conditions are maintained and sterically hindered bases (DIPEA) are applied to achieve this.

For example compounds H-Val-Arg-pNA and Msc-Val-Arg-pNA were obtained by acylation of the α-amino function of the partially protected nitroanilide Arg with the active ester Boc-Val-ONSu, removal of the N-protection by acidolysis, which resulted in H-Val-Arg-pNA. For preparation of Msc-Val-Arg-pNA the H-Val-Arg-pNA was subjected to subsequent acylation with Msc-Val-ONp.

Preferably a substrate useful in ETP determination in a continuous assay will exhibit $K_m$ for thrombin of 800–1250 μM, with more preference for 840–1000. The $k_{cat}$ is preferably concomitantly 0.4–0.9 for thrombin with more preference for 0.50–0.85. The ratio between $K_m/k_{cat}$ is preferably also 200–300 $(Ms)^{-1}$, preferably 225–275, most preferably 240–260. At the same time the substrate will preferably exhibit as low a $k_{cat}$ for Factor Xa as possible and as high a $K_m$ for Factor Xa as possible. Preferably the values will be $k_{cat}$=0 $s^{-1}$ and $K_m$>5000 μM.

Substrates of the above mentioned type can be used in samples exhibiting as much as 0.25 U ISH/ml heparin activity or the equivalent amount of anticoagulant activity due to any oral anticoagulant. These substrates however can also be used on samples that have not been subjected to the presence of oral anticoagulants and in particular have not been subjected to the presence of heparin. Substrates according to the invention that are preferred are capable of use in a continuous assay of ETP in a sample exhibiting heparin activity of more than 0.07 U ISH/ml or the equivalent value of other anticoagulant activity. Above this limit the state of the art compound SQ68 cannot be used reliably for ETP determination in a continuous assay.

S is preferably pNA. Other signal markers may be used but must be selected such that the kinetic parameters remain equivalent to those with pNA. Other signal markers are 5-amino-2-nitrobenzoic acid as an analogue of pNA or fluorogenic substrates such as water soluble derivatives based on 7-aminocoumarin-4-methane sulfonic acid (Sato E. et al. (1988) Chem. Pharm. Bull 36, 3496–3502).

Furthermore other substrates of a different structure were found that can also be used in a continuous assay of ETP in samples that have been subjected to the presence of high concentrations of anticoagulants in particular in samples that have been subjected to the presence of high concentrations of heparin. These substrates cannot be used for determination of ETP in samples that do not contain heparin or other anticoagulants as they exhibit an affinity for thrombin that is too high. These new substrates are capable of being used as thrombin substrates for continuous assay of ETP in samples comprising as much as 5.0 U ISH/ml heparin and/or an amount of other anticoagulant exhibiting the equivalent anticoagulant activity such that the total anticoagulant activity of the anticoagulants does not exceed 5.0 U ISH/ml or equivalent value.

Whether or not a substrate can be used as a substrate in heparinised plasma or plasma that has been subjected to treatment with one or more other anticoagulants as such or in combination with heparin is dependent in part on the values of the kinetic parameters. The first group of substrates mentioned according to the invention can be used in a sample that comprises heparin or another anticoagulant or a combination of anticoagulants. There is an upper limit of the concentration of heparin or anticoagulant activity that can be reliably tolerated. Preferably the above described P-Val-Xaa-S dipeptide substrates will not be used for determining ETP in a continuous assay when such samples exhibit more than 0.25 U ISH/ml or equivalent anticoagulant activity.

The second group of substrates whose structures are elucidated further on in the description can only be used in samples that have been subjected to treatment with one or more other anticoagulants as such or in combination with heparin.

The higher the heparin or anticoagulant concentration the lower the Michaelis constant $K_m$ and the larger the turnover number $k_{cat}$. In other words the higher the heparin concentration the more efficient the substrate must be to be converted by heparin or another anticoagulant. If the affinity for thrombin is too high it cannot be used in a continuous assay of ETP of a sample and thus it becomes impossible to monitor any inhibition of the activation cascade by the substrate.

The second group of substrates must retain high specificity for thrombin. It is subject in part to the same preconditions as set out in the description regarding the first group of substrates. The second group may hydrolyse thrombin at a higher rate than substrates of the first category but may not hydrolyse too well in view of the disruption of inhibition pattern that would occur thereby distorting the ETP curve.

In the already cited Angliker et al article it was illustrated that tailoring of di and tripeptide substrates that are especially selective towards thrombin will be difficult to achieve considering the influence of amino acids distal from the scissile bond of hydrolysis of fibrinogen by thrombin which was why they opted for use of longer substrates.

In the same article they concluded from their experiments with extended chloromethanes that residues Asp 7-Phe 8-Leu 9 of fibrinopeptide A are important for the specific interaction with thrombin.

Ac-Gly-Val-Arg-$CH_2$ is described as a relatively poor inactivator of thrombin; the $k_i$ value for this compound was $3\times10^4$ times lower than that for the best known tripeptide chloromethane inhibitor of thrombin D-Phe-Pro-Arg-$CH_2Cl$ (Hofsteenge et al (1986) Biochem. J. 237: pp243–251). Angliker et al. indicate that the hydrophobic interactions with the D-phenylalanine in the P3 position are probably responsible for the increased rate of reaction of D-Phe-Pro-Arg-$CH_2Cl$. In addition Phe 8 and Leu 9 bind to the hydrophobic aryl binding site. This site was discussed as the binding site for the D-Phenylalanine of D-Phe-Pro-Arg-$CH_2Cl$, however Phe 8 and Leu 9 enter the pocket from a different angle due to the chain reversal and occupy the site more fully.

Angliker et al. further disclose that the best inactivators based on fibrinopeptide A sequences reacted more than 100 times more slowly than did D-Phe-Pro-Arg-$CH_2Cl$. The reason therefore not being immediately apparent from the crystal structures. Angliker et al. hypothesized this could be due to the formation of a charged hydrogen bond between the α-amino group of the D-Phenylalanine and the carbonyl of Gly 216 of thrombin. A positively charged group has been shown to be essential for the optimal rate of reaction of the substrate D-Phe-pipecolyl-Arg-p-nitroaniline (Stone et al (1991) Biochemistry 25, 4622–4628)

In the light of this teaching it is therefore to be considered that the presence of D-Phenylalanine with pipecolyl or proline will not provide specificity for thrombin but will enhance rate of reaction. Also that for a substrate with specificity for thrombin the sequence Asp-Phe-Leu should be present.

Surprisingly we have found that dipeptide substrates comprising the structure Zaa-Pipecolyl-Yaa-S or Zaa-Pro-Yaa-S, wherein Zaa represents D-Phenylalanine, D-Tryptophan or D-Tyrosine, Pro represents proline, Yaa is an amino acid residue other than arginine and preferably other than alanine, phenylalanine, tryptophan and tyrosine and S is a signal marker as described for substrates of category 1 above, exhibit the desired specificity for thrombin and the desired rate of hydrolysis and solubility in aqueous solutions required for application in a continuous assay of ETP in a sample that has been subjected to the presence of heparin or one or more other anticoagulants. When Yaa is Orn a very good signal to noise ratio is obtained. As 20–50% of the initial substrate is consumed during thrombin generation this substrate cannot be used without a significant amount of heparin or other anticoagulant activity in the sample. In particular when Yaa is lysine an extremely useful substrate for use in a sample comprising heparin is provided.

Entries 1–8 of Tables 1 and 2 illustrate that the sequence H-D-Phe-Pipecolyl- or H-D-Phe-Pro- is so optimal for thrombin that even neutral or acidic side chain containing amino acids in position P1 are prone to hydrolysis. Zaa is preferably H-D-Phe. The $k_{cat}$ is low as expected but the $K_m$ is too low for use in a continuous assay for determination of ETP in a sample not comprising heparin or other anticoagulant activity. The compounds are surprisingly specific for thrombin but exhibit high rates of hydrolysis. We discovered that selecting Yaa at the P1 position to be different from arginine led to substrates that were well suited as the rates of hydrolysis were somewhat reduced. The substrates of this category can be used in continuous assays for ETP determination of samples comprising at least 2.0 U ISH/ml activity due to heparin or a corresponding amount of other anticoagulant generating an equivalent anticoagulant activity. Such a substrate can in fact successfully be used for reliable ETP determination in a continuous assay of samples comprising up to 5.0 U ISH/ml activity due to heparin or a corresponding amount of other anticoagulant generating an equivalent anticoagulant activity.

It is postulated that Pro and pip which are approximately equivalent in size fit in the S2 pocket of the thrombin binding site for fibrinogen. Smaller residues will lead to undesired interactions with Factor Xa. Valine which is larger than pro and pip fits the S2 pocket but not in the optimal way pro and pip do. D-phenylalanine is an aromatic amino acid residue and fits optimally into the $S_3$ binding pocket of thrombin. It is also possible to use D-aromatic amino acid like D-Trp or D-Tyr. Yaa is not arginine as the resulting substrate hydrolyses too fast to be of use in the continuous ETP assay. Yaa is not Ala, Phe, Trp, Tyr in order to prevent the substrate being recognized by other serine proteases present in plasma. Alanine is recognized by elastase phenylalanine, tryptophan and tyrosine by chymotrypsin and plasma peptidases.

Also surprisingly in view of the teaching of Angliker et al we discovered tripeptide substrates that exhibits the desired specificity for thrombin and the desired rate of hydrolysis and solubility in aqueous solutions required for application in a continuous assay of ETP in a sample that has been subjected to the presence of heparin or one or more other anticoagulants. This substrate comprises BOC-Gly-Val-Arg-S, with S preferably being pNA. The substrate can be used in a sample comprising more than 0.07 U ISH/ml, preferably between 0.85–2.0 U ISH/ml.

H-Gly-Val-Arg-pNA and BOC-Gly-Val-Arg-pNA are fibrinogen Aa-like fragments. A free N-terminus enhances the Km value but in this case the resulting substrate has a $k_{cat}$ that is still too high. Further research focussed on this substrate in which arginine was replaced by lysine, ornithine, or norleucine to reduce $k_{cat}$ with maintenance of the high $K_m$ value. As this substrate comprises a valine at position P2 this probably enhances the selectivity towards thrombin. The aforementioned modifications of P1 and additional polar or small neutral amino acids at the N terminus do not result in an optimal substrate suitable in the continuous registration of thrombin formation in plasma.

From Table 3 it is apparent that H-Gly-Val-Orn and H-Gly-Val-Nle-pNA are hydrolysed by neither thrombin nor Factor Xa. H-Gly-Val-Lys-pNA is hydrolysed by thrombin but not by Factor Xa which illustrates the specificity of the Val-Arg combination.

In particular from analysis of extension of the peptidyl portion of the Category 1 substrates carried out by us in which Gly-Val-Arg-pNA was analysed and illustrated a failure to hydrolyse it is all the more surprising that a BOC-Gly-Val-Arg-S substrate can be used with success.

Finally a fourth type of substrate was synthesized exhibiting the kinetic parameters required for ETP determination in a continuous assay of a sample exhibiting heparin activity. This substrate exhibits similar kinetic parameters to Msc-Val-Arg-pNA. This fourth type of substrate is H-Glu-Gly-Gly-Val-Arg-pNA. (SEQ ID NO: 3) It can be used in samples with or without heparin as described for the first category of substrate.

The subject invention is directed at improved methods of determining ETP in a continuous assay. The improved method comprises a method of determination in a continuous assay of ETP in a manner known per se, wherein the substrate for thrombin is a dipeptide substrate comprising the formula P-Val-Xaa-S, wherein

- P is an amino protective group, said group being non aromatic and polar,
- Val is a valine residue attached via a peptide bond to Xaa,
- Xaa is an amino acid residue comprising a terminal guanidino group or ureido group separated by at least 2 carbon atoms from the peptide backbone, said amino acid residue being attached to S,
- S is a signal group such as a chromophore that can be enzymatically hydrolysed with the proviso that the substrate is not $CH_3O$—CO—$CH_2$—CO-L-Val-Arg-pNa.

Preferably such a method is carried out on a sample comprising 0–0.25 U ISH/ml due to the presence of heparin or a corresponding amount of other anticoagulant exhibiting the same degree of anticoagulant activity. Such a method does not require the addition of ATIII and/or HCII or any other protease inhibitor. The method can be carried out on a sample exhibiting more than 0.07 U ISH/ml.

The subject invention is also directed at a method of determining ETP of a sample comprising more than 0.07 U ISH/ml, preferably more than 0.85 U ISH/ml in a continuous assay in a manner known per se, wherein the substrate for thrombin is Boc-Gly-Val-Arg-pNa or a salt thereof such as Boc-Gly-Val-Arg-pNa.HCl. In a preferred embodiment the sample comprises less than 2.0 U ISH/ml.

The subject invention is also directed at a method of determining ETP of a sample comprising more than 0.07 U ISH/ml, preferably more than 2.0 U ISH/ml in a continuous assay in a manner known per se, wherein the substrate for thrombin is a dipeptide substrate comprising the structure Zaa-Pipecolyl-Yaa-S or H-D-Phe-Pro-Yaa-S, wherein

- Zaa represents D-Phenylalanine, D-tryptophan or D-tyrosine,
- Pro represents proline,
- Yaa is an amino acid residue other than arginine and preferably other than alanine, phenylalanine, tryptophan and tyrosine and
- S is a signal marker as described for substrates of category 1 above.

When the sample can comprise elastase Yaa should not be analine. When the sample can comprise chymotrypsin or plasma peptidases Yaa should not be Phe, Trp or Tyr. In a preferred embodiment the sample comprises less than 5.0 U ISH/ml as at higher heparin concentrations incipient turbidities hamper the determination of the thrombin generation curve. Such a method according to the invention can suitably be carried out with H-D-Phe-Pro-Lys-pNA or a salt thereof such as 2HCl.H-D-Phe-Pro-Lys-pNA.

The invention also comprises determining ETP of a sample comprising 0.0–0.25 U ISH/ml, preferably more than 0.07 U ISH/ml in a continuous assay in a manner known per se wherein the substrate for thrombin is H-Glu-Gly-Gly-Val-Arg-pNA or a salt thereof. In the whole text where U ISH/ml is used the anticoagulant activity is implied due to heparin or the equivalent anticoagulant activity due to any other anticoagulant is implied as such or in combination with each other. In the whole text where substrate is described any salts of such substrate that are soluble in the sample are also implied.

A further improved method for determining ETP comprises addition of a selective denaturing agent of $\alpha_2$-macroglobulin to the sample to be determined prior to determination of the ETP or at the moment the ETP determination occurs. Most $\alpha_2$-macroglobulins are tetramers consisting of pairwise disulfide bridged subunits wherein an internal S-cysteinyl-γ-glutamyl thiol ester provides a potential covalent binding site for the target protease (Reviewed by: Sottrup-Jensen, L. (1989), J. Biol. Chem. 264, 11539–11542). Each thiol ester is reactive towards amines [a) Larsson, L. J. and Björk, I. (1984) Biochemistry 23, 2802–2807; b) thiol esters are weakly activated esters: Schwyzer, R. (1953) Helv. Chim. Acta 36, 414–424); aminolysis of this thiol ester results in nearly complete loss of protease binding capacity (Lonberg-Holm, K., Reed, D. L., Roberts, R. C. and Damato-McCabe, D. (1987) J. Biol. Chem. 262, 4844–4853]. In most cases methylamine is used as denaturing agent of $\alpha_2$-macroglobulin [a) Björk, I. et al. (1985) Biochemistry 24, 2653–2660; b) Eccleston E. D. and Howard, J. B. (1985) J. Biol. Chem. 260, 10169–10176], but this base (pKa=10.64) cannot be used in the continuous assay for ETP determination. hydroxylamine which is a much weaker base (pKa=6.03) is known to be an agent which selectively denaturates thiol ester bonds under neutral conditions without affecting the biological activity of enzyme systems [a) Roskoski. R., Jr. (1974) Biochemistry 13, 5141–5144; b) Duncan, R. J. S., Weston, P. D. and Wriggleworth, R. (1983) Anal. Biochem. 132. 68–73]. Inclusion of hydroxylamine in a sample of which the ETP is to be determined in a manner further known per se results in a significantly reduced end level of thrombin-$\alpha_2$-macroglobulin, without affecting thrombin generation. This result can already be achieved by addition of as little as 15 mM hydroxylamine (FIGS. 2 and 3 illustrate 25 mM). Preferably the maximum amount of hydroxylamine to be added is 100 mM.

The effect of hydroxylamine on the prothrombinase activity is presented in FIG. 4 and the decay constants are given in table 4. FIG. 4 shows that the maximum of the prothrombinase activity is not lowered but a small shift to a later time point is observed.

From these experiments it was concluded hydroxylamine is ideally suited to denaturate $\alpha_2$-macroglobulin without affecting the coagulation cascade. Hydrolytic activity of a thrombin-$\alpha_2$-macroglobulin complex towards a substrate can thus be reduced, thereby eliminating a possible source of inaccuracy. Unexpectedly the hydroxylamine does not affect the prothrombinase complex and does not interfere with the coagulation cascade.

Furthermore the addition of hydroxylamine to the sample to be tested offers the further advantage that when the sample is plasma it does not need to be defibrinated. In the presence of a large excess of hydroxylamine thrombin cleaved fibrinogen does not polymerize to form insoluble fibrin by the action of factor XIIIa. Factor XIIIa which is a transglutaminase evidently incorporates hydroxylamine in fibrin monomers instead of the standard $\epsilon$-amino group of a lysyl residue occurring in fibrin monomers. Incorporation of hydroxylamine results in the formation of a clear gel permitting the passage of light. No precipitating reaction products that can disturb the optical density recording are produced. It is thus possible to measure a thrombin generation curve in non defibrinated plasma with a zero end level of thrombin-$\alpha_2$-macroglobulin complex. In FIG. 5 it is shown that in this system even the effect of heparin (0.05 U ISH/ml) is measurable.

A preferred embodiment of the method according to the invention comprises a method for determining the ETP of a sample comprising at least 0.07 U ISH/ml or a corresponding amount of one or more other anticoagulants, resulting in a total anticoagulant activity of at least 0.07 U ISH/mi, wherein a substrate according to the invention of any of the three categories disclosed above is applied in a manner known per se for a thrombin substrate in a manner known per se for determining the ETP of a sample, said method further comprising the step of adding hydroxylamine to the sample to be tested prior to or at the beginning of the ETP determination. With particular advantage the method according to the invention wherein hydroxylamine is added to the sample is carried out with a sample of nondefibrinated plasma.

Another embodiment of the method according to the invention comprises a method for determining the ETP of a sample comprising at least 0.07 U ISH/ml or a corresponding amount of one or more other anticoagulants, resulting in a total anticoagulant activity of at least 0.07 U ISH/ml, wherein a substrate according to the invention of any of the four categories disclosed above is applied in a manner known per se for a thrombin substrate in a manner known per se for determining the ETP of a sample.

Any other methods other than ETP determination in which the novel substrates according to the invention can be used as substrates for thrombin will be apparent to a person skilled in the art on the basis of the characteristics given. The use of such substrates is obviously not necessarily restricted to the ETP determination.

EXAMPLE 1

The Synthesis of Chromogenic Substrates According to the Invention

Methods of Synthesis S2238-derived substrates (scheme 2): The dipeptide ester Boc-D-Phe-Pip-OMe was prepared from Boc-D-Phe-OH and HCl.H-Pip-OMe using DCC/HOBt in EtOAc as solvent in the presence of 1 eq. DIPEA as described by König and Geiger[26]. In this strategy the $\alpha$-amino function was protected by a Boc-group; this enables a single deprotection step of the protected tripeptide p-nitroanilide (vide infra) for conversion into the desired substrate. As carboxyl protection, a methyl ester was used. The methyl ester can be easily converted into the corresponding hydrazide. After work-up the dipeptide methyl ester was obtained as a colourless oil in 74% yield and directly used for further synthesis. Its conversion into the protected dipeptide hydrazide was carried out by treatment with 5 eq. of $N_2H_4.H_2O$ in MeOH for three days at room temperature. The product was obtained as white crystals after recrystallization from iso-propyl alcohol in 70% yield. Hydrazide derivatives give access to azides which can be coupled to amino components via the azide method as described by Curtius[27]. This is one of the earliest peptide coupling methods described in the literature. Its value has been found in the fact that acylpeptides can be coupled without or with a minimal degree of racemization. The conversion of Boc-D-Phe-Pip-$N_2H_3$ to its corresponding azide was performed by tert.-butyl nitrite in the presence of a strong mineral acid (HCl in EtOAc) in DMF as solvent at −20° C. as described by Honzl and Rudinger[28]. They studied the conditions in which the unwanted Curtius rearrangement is largely suppressed and the desired coupling reaction is favoured.

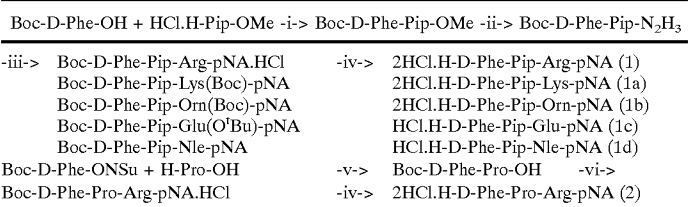

Boc-D-Phe-OH + HCl.H-Pip-OMe -i-> Boc-D-Phe-Pip-OMe -ii-> Boc-D-Phe-Pip-$N_2H_3$

| | | | |
|---|---|---|---|
| -iii-> | Boc-D-Phe-Pip-Arg-pNA.HCl | -iv-> | 2HCl.H-D-Phe-Pip-Arg-pNA (1) |
| | Boc-D-Phe-Pip-Lys(Boc)-pNA | | 2HCl.H-D-Phe-Pip-Lys-pNA (1a) |
| | Boc-D-Phe-Pip-Orn(Boc)-pNA | | 2HCl.H-D-Phe-Pip-Orn-pNA (1b) |
| | Boc-D-Phe-Pip-Glu($O^tBu$)-pNA | | HCl.H-D-Phe-Pip-Glu-pNA (1c) |
| | Boc-D-Phe-Pip-Nle-pNA | | HCl.H-D-Phe-Pip-Nle-pNA (1d) |
| Boc-D-Phe-ONSu + H-Pro-OH | | -v-> | Boc-D-Phe-Pro-OH -vi-> |
| Boc-D-Phe-Pro-Arg-pNA.HCl | | -iv-> | 2HCl.H-D-Phe-Pro-Arg-pNA (2) |

-continued

| Boc-D-Phe-OH + HCl.H-Pip-OMe -i-> Boc-D-Phe-Pip-OMe -ii-> Boc-D-Phe-Pip-$N_2H_3$ | |
|---|---|
| Boc-D-Phe-Pro-Lys(Boc)-pNA | 2HCl.H-D-Phe-Pro-Lys-pNA (2a) |
| Boc-D-Phe-Pro-Nle-pNA | HCl.H-D-Phe-Pro-Nle-pNA (2b) |

Scheme 2: Synthesis scheme of substrates derived from S2238 as lead structure;
i) DCC/HOBt/DIPEA in EtOAc;
ii) $N_2H_4.H_2O$ in MeOH;
iii) 1. tert.-BuONO/HCl at −20° C., 2. DIPEA, 3. H-Xaa-pNA/DIPEA in DMF at 0° C.;
iv) HCl in AcOH/EtOAc 1:1 v/v;
v) $NaHCO_3$ in $H_2O/CH_3CN$ 1:1 v/v;
vi) DCC/HOBt/DIPEA/H-Xaa-pNA.

This coupling procedure was used to come to five fully protected tripeptides. The side chain functionalities were protected with acid-labile protective groups. The ω-amino function of lysine and ornithine was protected by a Boc-group. The carboxyl side chain of glutamic acid was protected as a tert.-butyl ester. The guanidino function of arginine was protected by protonation only, to avoid harsh deprotection conditions when the usual protective groups would be used. The α-amino function is selectively liberated from the dihydrochloride by addition of DIPEA due to its lower $PK_a$ value; the guanidino function is the stonger base. Boc-D-Phe-Pip-$N_3$ was synthesized in situ and coupled to the amino acid p-nitroanilide in DMF at 0° C. during 16 hrs at neutral pH. The amino components were added as hydrochlorides (2HCl.H-Arg-pNA, HCl.H-Nle-pNA) or as free amines (H-Lys(Boc)-pNA, H-Orn(Boc)-pNA and H-Glu ($O^tBu$)-pNA). The latter three were obtained from their corresponding Fmoc-protected derivatives. Fmoc-removal was carried out with 20% piperidine in DMF for 30 min at room temperature. After removal of the solvent and coevaporation with DMF to remove excess piperidine, the p-nitroanilides were used for synthesis without further purification. When the acylation was complete, DMF was evaporated in vacuo and the product was purified by column chromatography. Arginine derivatives were purified by counter current distribution after Craig[29,30]. The protected tripeptides were obtained as amorphous products in yields of 62–95%. Final deprotection was with HCl in EtOAc. Purification by counter current distribution and lyophilization from $H_2O$ gave the products as off-white fluffy powders in 46–94% yield.

The derivatives in which pipecolic acid is replaced by a proline residue were synthesized as follows. H-Pro-OH was acylated by Boc-D-Phe-ONSu in $H_2O/CH_3CN$ 1:1 v/v in the presence of 2.25 eq. $NaHCO_3$. The dipeptide acid was obtained as a white solid in 72% yield. Since acylpeptides with a carboxy-terminal proline can be coupled without racemization, the amino acid p-nitroanilides were acylated directly with Boc-D-Phe-Pro-OH using DCC/HOBt. The coupling reactions were carried out in EtOAc as solvent (DMF was used for arginine p-nitroanilide; work-up was performed in BuOH after evaporation of DMF). After work-up by aqueous extraction, the product was purified by column chromatography. The arginine derivative was purified by counter current distribution. Drying of compounds with protonated guanidino functions is not recommended: premature crystallization of sulphate salts can occur and appears as a source of unnecessary product loss. The protected tripeptides were obtained as amorphous products in 55–90% yield. After deprotection, the unprotected compounds were purified by counter current distribution, the lyophilized products were off-white fluffy materials and were obtained in 75–91% yield.

SQ68-derived substrates: (scheme 3): Boc-Xaa-Arg-pNA.HCl dipeptides were synthesized from 2HCl.H-Arg-pNA by acylation with Boc-Xaa-ONSu in DMF as the solvent in the presence of 1 eq. DIPEA during 16 hrs at room temperature. Boc-Gly-OH was coupled using DCC/HOBt to H-Arg-pNA.HCl. When the reactions were complete, DMF was evaporated in vacuo and the residue was dissolved in BuOH and subsequently washed with aqueous acid and -base. The BuOH solution was not dried but directly evaporated to dryness. The obtained products were purified by counter current distribution in 70–89% yield. The work-up and purification of Boc-Gly-Arg-pNA.HCl was slightly different due to the substantial water solubility. The reaction mixture was concentrated and the crude dipeptide was directly purified by counter current distribution, yield: 88%. The five dipeptides were lyophilized from AcOH to obtain amorphous powders. After Boc-removal and subsequent purification, the α-amino function was modified by a malonic acid derivative. These couplings were carried out by DCC/HOBt (or the ONSu ester of MZ) in DMF in the presence of 1 eq. DIPEA. The products were purified by counter current distribution and lyophilized from $H_2O$ which resulted in off-white fluffy powders, yield: 34–74%. The β-naphtalenesulfonyl- and p-toluenesulfonyl modifications were performed with the acid chlorides using dry pyridine in the presence of 2 eq. DIPEA during 16 hrs at room temperature. After removal of the solvent, the products were purified by counter current distribution and lyophilized from AcOH, yield: 59 respectively 63%.

Boc-Gly-OH + 2HCl.H-Arg-pNA-i->
Boc-Gly-Arg-pNA.HCl-ii->2HCl.H-Gly-Arg-pNA(3)

| | |
|---|---|
| -iii-> | MZ-Gly-Arg-pNA.HCl (3a) |
| | MMZ-Gly-Arg-pNA.HCl (3b) |
| | DMMZ-Gly-Arg-pNA.HCl (3c) |
| | DEMZ-Gly-Arg-pNA.HCl (3d) |
| -iv-> | βNS-Gly-Arg-pNA.HCl (3e) |
| | pTS-Gly-Arg-pNA.HCl (3f) |

Boc-Xaa-ONSu + 2HCl.H-Arg-pNA-v->
Boc-Xaa-Arg-pNAHCl-ii->2HCl.H-Xaa-Arg-pNA

| | |
|---|---|
| --> 2HCl.H-Ala-Arg-pNA(4) -iii-> | MZ-Ala-Arg-pNA.HCl (4a) |
| | MMZ-Ala-Arg-pNA.HCl (4b) |
| | DMMZ-Ala-Arg-pNA.HCl (4c) |
| --> 2HCl.H-D-Ala-Arg-pNA(5)-iii-> | MZ-D-Ala-Arg-pNA.HCl (5a) |
| --> 2HCl.H-Val-Arg-pNA(6)-iii-> | MZ-Val-Arg-pNA.HCl (6a) |
| --> 2HCl.H-D-Val-Arg-pNA(7)-iii-> | MZ-D-Val-Arg-pNA.HCl (7a) |

Scheme 3: Synthesis scheme of substrates with SQ68 as lead structure;
i) DCC/HOBt/NMM in DMF,
ii) HCl in EtOAc/AcOH 1:1 v/v,
iii) malonic acid monomethyl ester/DCC/HOBt/DIPEA (or MZ-ONSu/DIPEA) in DMF,
iv) arylsulfonyl chloride/DIPEA in dry pyridine,
v) DIPEA in DMF.

Conclusion

It was shown that orthogonally protected amino acid p-nitroanilides are well suited for fragment condensations in DCC/HOBt- or azide-mediated coupling procedures. Protonation of the guanidino side function of arginine has the advantage of evading harsh deprotection conditions. However, its highly polar character necessitates modified work-up and purification methods. Some of the substrates described in this example were to be used in the continuous registration of thrombin formation in plasma, but some of them could not be used due to the low water solubility.

Experimental Procedures

General $^1$H NMR spectra were recorded on Bruker AM 100 and Bruker AM 400 spectrometers. As an internal standard the residual solvent peak was used. Chemical shifts are given in part per million (ppm). Optical rotations were measured on a Perkin Elmer 241 polarimeter in a 10 cm cuvette at room temperature. Melting points were determined with a Büchi melting point apparatus (Tottoli). TLC was performed on Merck SILICAGEL $60F_{254}$ plates, and column chromatography on Merck KIESELGEL 60, 70–230 Mesh ASTM. Spots were detected by UV-fluorescence quenching, ninhydrine (free amino functions), chlorine/TDM (NH groups), Barton's—(hydrazides) and Sakaguchi's (arginine residues) reagent. Methanol was refluxed on magnesium turnings for two hours, distilled and stored on 3 Å molsieves. Pyridine was distilled over KOH pellets and stored on 4 Å molsieves. Boc-amino acids were synthesized by the method of Schnabel[31]. Their hydroxysuccinimide esters were prepared according to Anderson et al.[32] Amino acid p-nitroanilides were prepared as described elsewere. The resolution of DL-pipecolic acid was carried out according to the method of Mende and Lukes et al.[33] Malonic acid and dimethylmalonic acid were converted to their corresponding dimethyl esters by heating the dicarboxylic acid with an excess of methanol in the presence of concentrated sulfuric acid[34]. Dimethyl methylmalonate was prepared by generating the mono-sodio derivative of dimethyl malonate which reacts with methyl iodide via a $S_N2$ mechanism[34]. The corresponding half esters were prepared by controlled partial hydrolysis of the diester with one equivalent of potassium hydroxide[35]. The monomethyl ester of diethylmalonic acid was obtained in a direct way by refluxing the acid in an excess of methanol with sulfuric acid as catalyst. Dimethylmalonic acid and DL-pipecolic acid were from Janssen, diethylmalonic acid and D(−)-tartaric acid were from Aldrich. Naphtalene-2-sulfonyl chloride, toluene-4-sulfonyl chloride and D-alanine were obtained from Fluka. Boc-Nle-OH, Boc-D-Val-ONSu and Fmoc-Orn(Boc)-OH were from Bachem. D-Phenylalanine was a generous gift of Dr. J. Kamphuis (DSM Research, Geleen, The Netherlands).

Syntheses

Boc-D-Phe-Pip-$N_2H_3$

To a solution of Boc-D-Phe-OH (19.88 g, 75 mmol) in EtOAc (350 mL) was added HCl.H-Pip-OMe[33] (13.46 g, 75 mmol, 1.0 eq.), HOBt (12.62 g, 82.5 mmol, 1.10 eq.) and NMM (8.75 mL, 78.7 mmol, 1.05 eq.). The obtained suspension was cooled on ice and DCC (16.22 g, 78.7 mmol, 1.05 eq.) was added. After stirring for two hrs at 0° C. and 16 hrs at room temperature, DCU was filtered off. The pale yellow EtOAc solution was successively washed with 2N $KHSO_4$, $H_2O$, saturated $NaHCO_3$ and saturated NaCl (four times 50 mL each). The obtained organic solution was dried on $Na_2SO_4$, filtered and evaporated in vacuo. The residual oil contained some DCU, so diethyl ether was added and the suspension was filtered. The filtrate was evaporated in vacuo; the obtained residue was a clear yellowish oil, yield: 21.52 g (74%). This product was checked by TLC on purity and directly used for further synthesis ($R_f$($CH_2Cl_2$/MeOH 9:1 v/v): 0.87). The protected dipeptide methyl ester was dissolved in MeOH (150 mL) and $N_2H_4.H_2O$ (13.5 mL, 278 mmol, 5.0 eq.) was added. This reaction mixture was left for three days at room temperature. The formed precipitate was filtered off and dried, yield: 12.48 g (58%). The filtrate was evaporated to 25 mL and dropped out into $H_2O$ (500 mL), to give another crop of 2.53 g. Total yield: 15.01 g (70%, overall: 52%), $R_f$($CH_2Cl_2$/MeOH 9:1 v/v): 0.54, $[\alpha]_D$=−77.1° C.=0.98 DMP, mp: 202–204° C., $^1$H NMR ($CD_3OD$): δ=1.15–1.38 (m, 6H, $CH_2$-Pip (3×2H)); 1.44 (s, 9H, Boc); 3.08/3.18 (dm, 2H, β-$CH_2$-Phe); 3.28 (m, 2H, N—$CH_2$-Pip); 4.58 (m, 1H, α-CH-Pip); 4.74 (m, 1H, α-CH-Phe); 7.20–7.33 (m, 5H, arom Phe).

Boc-D-Phe-Pip-X-pNA a) X=Arg.HCl

Boc-D-Phe-Pip-$N_2H_3$ (0.39 g, 1.0 mmol) was dissolved in DMF (10 mL) and cooled to −20° C. with dry ice/aceton. To this solution was added 2.3 M HCl/EtOAc (1.20 mL, 2.75 mmol, 2.75 eq.) followed by tert.-BuONO (0.114 mL, 1.20 mmol, 1.20 eq.). This reaction mixture was stirred for 15 min at −20° C. (After this period the azide-formation was complete.) The acid solution was neutralized by adding DIPEA (0.48 mL, 2.77 mmol). 2HCl.H-Arg-pNA (0.367 g, 1.0 mmol, 1.0 eq.) was added followed by 1.0 eq. DIPEA. This reaction mixture was kept on neutrality by adding DIPEA at regular time intervals. The obtained reaction medium was allowed to react during 16 hrs at 0° C. After this period, DMF was removed in vacuo and the oily residue was dissolved in BuOH (10 mL). The BuOH solution was washed with $H_2O$, saturated $NAHCO_3$ and saturated NaCl (three times 5 mL each) and evaporated in vacuo. Boc-D-Phe-Pip-Arg-pNA.HCl was purified by counter current distribution with BuOH/AcOH/$H_2O$ 4:1:5 v/v/v as solvent system (K=10.52) and lyophilized from AcOH. Yield: 0.613 g (89%), $R_f$(BuOH/AcOH/$H_2O$ 4:1:1 v/v/v): 0.75, $[\alpha]_D$=−90.0° C.=1 MeOH, $^1$H NMR ($CD_3OD$): δ=1.33 (s, 9H, Boc); 1.41 (m, 6H, $CH_2$-Pip (3×2H)); 1.67 (m, 2H, δ-$CH_2$-Arg); 1.86/2.04 (dm, 2H, β-$CH_2$-Arg); 2.93–3.04 (bm, 4H, β-$CH_2$-Phe/N—$CH_2$-Pip); 3.21 (m, 2H, δ-$CH_2$-Arg); 4.54 (m, 1H, α-CH-Pip); 4.78 (m, 1H, α-CH-Arg); 4.96 (m, 1H, α-CH-Phe); 7.21–7.35 (bm, 5H, arom Phe); 7.90/7.92–8.20/8.23 (dd, 4H, arom pNA).

b) X=Lys(Boc)

In general as described for a)

Quantities used: Boc-D-Phe-Pip-$N_2H_3$: 0.398 g (1.019 mmol), H-Lys(Boc)-pNA: 0.373 g (1.022 mmol). Extractions were performed with EtOAc, after drying on $Na_2SO_4$, the solvent was removed under reduced pressure. The obtained foam was purified by column chromatography with $CH_2Cl_2$/MeOH 98:2 v/v as eluens. Yield: 0.69 g (95%), $R_f$($CH_2Cl_2$/MeOH 98:2 v/v): 0.30, $[\alpha]_D$=−61.8° C.=0.44 MeOH, $^1$H NMR ($CD_3OD$): δ=1.18–1.56 (bm, 10H, γ-$CH_2$/δ-$CH_2$-Lys/$CH_2$-Pip (3×2H)); 1.34 (s, 9H, Boc); 1.41 (s, 9H, Boc); 1.93 (m, 2H, β-$CH_2$-Lys); 3.02 (m, 6H, N—$CH_2$-Pip/ε-$CH_2$-Lys/β-$CH_2$-Phe); 4.45 (m, 1H, α-CH-Pip); 4.78 (m, 1H, α-CH-Lys); 5.11 (m, 1H, α-CH-Phe); 7.21–7.34 (m, 5H, arom Phe); 7.85/7.87–8.16/8.18 (dd, 4H, arom pNA).

c) X=Orn(Boc)

Obtained as described for b)

Quantities used: Fmoc-Orn(Boc)-pNA: 0.625 g ( 1.089 mmol). The Fmoc-protection was removed by treatment with 20% piperidine in DMF (15 mL) during 35 min. After this period, the reaction mixture was evaporated to dryness and coevaporated with DMF to remove any residual piperidine. Yield: 0.525 g (74%). $R_f$($CH_2Cl_2$/MeOH 98:2 v/v): 0.22, $[\alpha]_D$=−64.8° C.=0.13 MeOH, $^1$H NMR ($CD_3OD$): δ=1.26–1.48 (bm, 6H, $CH_2$-Pip (3×2H)); 1.34 (s, 9H, Boc);

1.41 (s, 9H, Boc); 1.56/1.65 (dm, 2H, γ-$CH_2$-Orn); 1.78/1.99 (dm, 2H, β-$CH_2$-Orn); 2.97 (m, 2H, β-$CH_2$-Phe); 3.07 (m, 4H, δ-$CH_2$-Orn/N—$CH_2$-Pip); 4.48 (m, 2H, α-CH-Orn/α-CH-Pip); 4.79 (m, 1H, α-CH-Phe); 7.25–7.32 (m, 5H, arom Phe); 7.86/7.88–8.18/8.20 (dd, 4H, arom pNA).

d) X=Glu($O^tBu$)

Obtained as described for b)

Quantities used: Fmoc-Glu($O^tBu$)-pNA: 0.577 g ( 1.06 mmol). The Fmoc-protection was removed as described above. Yield: 0.422 g (62%), $R_f$($CH_2Cl_2$/MeOH 98:2 v/v): 0.44, $[\alpha]_D$=−78.5° C.=0.33 MeOH, $^1$H NMR ($CD_3OD$): δ=1.26–1.54 (bm, 8H, β-$CH_2$-Glu/$CH_2$-Pip (3×2H)); 1.33 (s, 9H, $O^tBu$); 1.43 (s, 9H, Boc); 2.38 (m, 2H, γ-$CH_2$-Glu); 2.96 (m, 2H, β-$CH_2$-Phe); 3.08 (m, 2H, N—$CH_2$-Pip); 4.53 (dd, 1H, α-CH-Glu); 4.59 (m, 1H, α-CH-Pip); 4.82 (m, 1H, α-CH-Phe); 7.26–7.33 (m, 5H, arom Phe); 7.89/7.91–8.20/8.22 (dd, 4H, arom pNA).

e) X=NZe

Obtained as described for b)

Quantities used: HCl.H-Nle-pNA: 0.288 g (1.0 mmol), DIPEA: 0.173 mL (1.0 mmol). Yield: 0.512 g (84%), $R_f$($CH_2Cl_2$/MeOH 98:2 v/v): 0.42, $[\alpha]_D$=−93.9° C.=0.23 MeOH.

nHCO.H-D-Phe-Pip-X-pNA

The protected tripeptide was dissolved in EtOAc or AcOH (1 mmol in 5 mL). To the solution 2.3 M HCl/EtOAc (10 mL for 1 mmol) was added and the reaction mixture was stirred until deprotection was complete. The acid was quenched with tert.-BuOH (10 mL) and evaporated in vacuo. The residue was coevaporated with tert.-BuOH (twice) and with MeOH (once). The residue was dissolved in $H_2O$ and lyophilized. Crude tripeptides were purified by counter current distribution with BuOH/AcOH/$H_2O$ 4:1:5 v/v/v as solvent system.

a) n=2, X=Arg (1)

Yield: 0.436 g (96%), $R_f$(BuOH/AcOH/$H_2O$ 4:1:1 v/v/v): 0.52 (K=0.92), $[\alpha]_D$=−128.7° C.=1 MeOH, $^1$H NMR ($D_2O$): δ=1.18 (m, 2H, $CH_2$-Pip); 1.44 (m, 2H, γ-$CH_2$-Arg); 1.63 (m, 4H, $CH_2$-Pip (2×2H)); 1.88 (m, 2H, β-$CH_2$-Arg); 3.13 (m, 2H, β-$CH_2$-Phe); 3.21 (m, 4H, δ-$CH_2$-Arg/N—$CH_2$-Pip); 4.40 (m, 1H, α-CH-Arg); 4.69 (bs, 1H, α-CH-Pip); 4.81 (m, 1H, α-CH-Phe); 7.26 (m, 2H, arom Phe); 7.38 (m, 3H, arom Phe); 7.63/7.65–8.18/8.20 (dd, 4H, arom pNA).

b) n=2, X=Lys (1a)

Yield: 0.297 g (72%), $R_f$(BuOH/AcOH/$H_2O$ 4:1:1 v/v/v): 0.60, $[\alpha]_D$=−115.3° C.=0.15 MeOH, $^1$H NMR ($CD_3OD$): δ=1.17–1.60 (bm, 8H, γ-$CH_2$-Lys/$CH_2$-Pip (3×2H)); 1.71 (m, 2H, δ-$CH_2$-Lys); 1.94 (m, 2H, β-$CH_2$-Lys); 2.94 (t, 2H, ε-$CH_2$-Lys); 3.08/3.18 (dm, 2H, β-$CH_2$-Phe); 3.28 (bs, 2H, N—$CH_2$-Pip); 4.48 (m, 1H, α-CH-Lys); 4.58 (m, 1H, α-CH-Pip); 4.72 (m, 1H, α-CH-Phe); 7.29–7.41 (m, 5H, arom Phe); 7.85/7.88–8.20/8.22 (dd, 4H, arom pNA).

c) n=2, X=Orn (1b)

Yield: 0.315 g (96%), $R_f$(BuOH/AcOH/$H_2O$ 4:1:1 v/v/v): 0.42 (K=0.71), $[\alpha]_D$=−96.7° C.=0.18 MeOH, $^1$H NMR ($CD_3OD$): δ=1.29–1.49 (m, 6H, $CH_2$-Pip (3×2H)); 1.62–1.77 (dm, 2H, γ-$CH_2$-Orn); 2.00–2.15 (dm, 2H, β-$CH_2$-Orn); 2.98 (m, 6H, β-$CH_2$-Phe/N—$CH_2$-Pip/δ-$CH_2$-Orn); 4.34 (m, 1H, α-CH-Pip); 4.46 (m, 1H, α-CH-Orn); 4.57 (m, 1H, α-CH-Phe); 7.23–7.35 (m, 5H, arom Phe); 7.85/7.87–8.20/8.22 (dd, 4H, arom pNA).

d) n=1, X=GZu (1c)

Yield: 0.158 g (64%), $R_f$(BuOH/AcOH/$H_2O$ 4:1:1 v/v/v): 0.67 (K=5.15), $[\alpha]_D$=−107.4° C.=0.22 MeOH, $^1$H NMR ($CD_3OD$): δ=1.11–1.35 (m, 6H, $CH_2$-Pip (3×2H); 2.03 (in, 2H, β-$CH_2$-Glu); 2.26/2.42 (dm, 2H, γ-$CH_2$-Glu); 2.82/3.55 (dm, 2H, N—$CH_2$-Pip); 3.11/3.24 (dm, 2H, β-$CH_2$-Phe); 4.17 (m, 1H, α-CH-Glu); 4.52 (m, 1H, α-CH-Pip); 4.82 (m, 1H, α-CH-Phe); 7.26–7.41 (m, 5H, arom Phe); 7.84/7.86–8.19/8.22 (dd, 4H, arom pNA).

e) n=1, X=Nle (1d)

Yield: 0.124 g (46%). $R_f$(BuOH/AcOH/$H_2O$ 4:1:1 v/v/v): 0.82, $[\alpha]_D$=−117.1° C.=0.17 MeOH, $^1$H NMR ($CD_3OD$): δ=0.93 (t, 3H, ε-$CH_3$-Nle); 1.29–1.48 (bm, 10H, γ-$CH_2$-Nle/δ-$CH_2$-Nle/$CH_2$-Pip (3×2H)); 1.78/1.87 (dm, 2H, β-$CH_2$-Nle); 3.00 (m, 4H, N—$CH_2$-Pip/β-$CH_2$-Phe); 4.45 (m, 2H, α-CH-Nle/α-CH-Pip); 5.07 (m, 1H, α-CH-Phe); 7.24–7.37 (m, 5H, arom Phe); 7.82/7.84–8.19/8.21 (dd, 4H, arom pNA).

Boc-D-Phe-Pro-OH

To a solution of H-Pro-OH (1.00 g, 8.70 mmol, 1.09 eq.) and $NaHCO_3$ (1.40 g, 16.7 mmol, 2.09 eq.) in $H_2O$ (10 mL) a solution of Boc-D-Phe-ONSu (2.90 g, 8.01 mmol) in $CH_3CN$ (30 mL) was added dropwise. The obtained reaction mixture was stirred at room temperature for 16 hrs. After this period of stirring the reaction mixture was evaporated in vacuo, the resulting syrup was diluted with water and the solution was acidified with 2N $KHSO_4$ to pH=3 and extracted into EtOAc (50 mL). The EtOAc solution was washed with saturated NaCl (three times 20 mL), dried on $Na_2SO_4$, filtered and evaporated to dryness. The residue was precipitated in diethyl ether, filtered and dried. Yield: 2.12 g (73%), $R_f$($CH_2Cl_2$/MeOH 8:2 v/v): 0.45, $[\alpha]_D$=−56.5° C.=0.78 MeOH, mp: 168° C., $^1$H NMR ($CDCl_3$): δ=1.43 (s, 9H, Boc); 2.24 (m, 2H, $CH_2$-Pro); 2.51 (m, 2H, $CH_2$-Pro); 3.02 (d, 2H, β-$CH_2$-Phe); 3.55 (m, 2H, N—$CH_2$-Pro); 4.34 (m, 1H, α-CH-Pro); 4.61 (m, 1H, α-CH-Phe); 5.33 (d, 1H, NH); 7.26 (bs, 5H, arom Phe).

Boc-D-Phe-Pro-Arg-pNA.HCl

To a solution of Boc-D-Phe-Pro-OH (0.362 g, 1.00 mmol), 2HCl.H-Arg-pNA (0.365 g. 0.995 mmol, 0.995 eq.), HOBt (0.172 g, 1.12 mmol, 1.12 eq.) and DIPEA (0.18 mL, 1.05 mmol, 1.05 eq.) in DMF (10 mL), DCC (0.221 g, 1.07 mmol, 1.07 eq.) was added. The obtained reaction mixture was stirred for one hour on ice and 17 hrs at room temperature. The formed DCU was filtered off and DMF was evaporated in vocuo. The oily residue was dissolved in BuOH (20 mL) and subsequently washed with $H_2O$, saturated $NaHCO_3$ and saturated NaCl (four times 10 mL each). The clear organic solution was evaporated in vacuo and the residue was purified by counter distribution with the solvent system: BuOH/AcOH/$H_2O$ 4:1:5 v/v/v. The pure product was lyophilized from AcOH. Yield: 0.51 g (76%), $R_f$(BuOH/AcOH/$H_2O$ 4:1:1 v/v/v): 0.65 (K=6.48), $[\alpha]_D$=−31.3° C.=0.22 MeOH, $^1$H NMR ($CD_3OD$): δ=1.20 (s, 9H, Boc); 1.58–2.18 (bm, 8H, β-$CH_2$-Arg/γ-$CH_2$-Arg/$CH_2$-Pro (2×2H)); 2.77/3.69 (dm, 2H, N—$CH_2$-Pro); 3.02 (m, 2H, γ-$CH_2$-Phe); 3.22 (m, 2H, δ-$CH_2$-Arg); 4.27 (m, 1H, α-CH-Pro); 4.49 (m, 1H, α-CH-Arg); 4.55 (m, 1H, α-CH-Phe); 7.28–7.36 (m, 5H, arom Phe); 8.12/8.15–8.23/8.26 (dd, 4H, arom pNA).

Boc-D-Phe-Pro-X-pNA a) X=Lys(Boc)

Boc-D-Phe-Pro-OH (0.1975 g, 0.546 mmol, 1.01 eq.) was coupled in EtOAc (10 mL) with H-Lys(Boc)-pNA (0.1982 g, 0.543 mmol) using DCC (0.113 g, 0.55 mmol, 1.01 eq.) in the presence of HOBt (0.077 g, 0.55 mmol, 1.01 eq.). After one hour of stirring at 0° C. the reaction mixture was stirred overnight at room temperature. DCU was filtered off, and the organic solution was washed with saturated $NaHCO_3$, $H_2O$, 2N $KHSO_4$ and saturated NaCl (three times 10 mL each). The clear yellowish EtOAc solution was dried on $Na_2SO_4$, filtered and evaporated in vacuo. The resulting foam was purified by column chromatography on silica gel with $CH_2Cl_2$/MeOH 98:2 v/v as eluent. Yield: 0.212 g (55%), $R_f$($CH_2Cl_2$/MeOH 98:2 v/v): 0.21, $R_f$($CH_2Cl_2$/MeOH 95:5 v/v): 0.62, $[\alpha]_D$=−52.9° C.=0.18 MeOH, $^1$H NMR ($CD_3OD$): δ=1.20 (s, 9H, Boc); 1.33–1.60 (bm, 6H, γ-$CH_2$-Lys/$CH_2$-Pro (2×2H)); 1.42 (s, 9H, Boc); 1.77–2.10 (bm, 4H, β-$CH_2$-Lys/δ-$CH_2$-Lys); 2.73/3.70 (dm, 2H, N—$CH_2$-Pro); 3.03 (m, 4H, ε-$CH_2$-Lys/β-$CH_2$-Phe); 4.26 (m, 1H, α-CH-Pro); 4.48 (m, 2H, α-CH-Lys/α-CH-Phe); 7.26–7.35 (m, 5H, arom Phe); 8.12/8.14–8.22/8.24 (dd, 4H, arom pNA).

b) X=Nle

Obtained as described for a)

Quantities used: Boc-D-Phe-Pro-OH: 0.202 g (0.558 mmol), HCl.H-Nle-pNA: 0.162 g (0.562 mmol, 1.01 eq.), HOBt: 95.4 mg (0.624 mmol, 1.12 eq.), DIPEA: 100 μL (0.575 mmol, 1.03 eq.) and DCC: 0.132 g (0.641 mmol, 1.15 eq.) in 10 mL EtOAc. Yield: 0.299 g (90%), $R_f$($CH_2Cl_2$/MeOH 98:2 v/v): 0.38, $[\alpha]_D$=−72.0° C.=0.15 MeOH.

nHCl.H-D-Phe-Pro-X-pNA

The protected tripeptide was dissolved in EtOAc or AcOH (1 mmol in 5 mL). To this solution, 2.3 M HCl/EtOAc (5 mL for 1 mmol) was added and stirred for a period until deprotection was complete. After completion, the acid was quenched with tert.-BuOH (10 mL) and the mixture was evaporated in vacuo. After coevaporation with tert.-BuOH (twice 10 mL) and MeOH (once 10 mL) the residue was dissolved in $H_2O$ and lyophilized.

a) n=2, X=Arg (2)

Yield: 0.330 g (91%), $R_f$(BuOH/AcOH/$H_2O$ 4:1:1 v/v/v): 0.48, $[\alpha]_D$=−102.0° C.=0.10 MeOH, $^1$H NMR ($CD_3OD$): δ=1.51–2.04 (bm, 8H, β-$CH_2$/γ-$CH_2$-Arg/$CH_2$-Pro (2×2H)); 2.64/3.65 (dm, 2H, N—$CH_2$-Pro); 3.14 (m, 2H, β-$CH_2$-Phe); 3.23 (m, 2H, δ-$CH_2$-Arg); 4.34 (m, 1H, α-CH-Pro); 4.43 (m, 2H, α-CH-Arg/α-CH-Phe); 7.30–7.42 (m, 5H, arom Phe); 7.94/7.96–8.21/8.23 (dd, 4H, arom pNA).

b) n=2, X=Lys (2a)

Yield: 0.110 g (75%), $R_f$(BuOH/AcOH/$H_2O$ 4:1:1 v/v/v): 0.44, $[\alpha]_D$=−138.9° C.=0.27 MeOH, $^1$H NMR ($CD_3OD$): δ=1.50–2.00 (bm, 10H, β-$CH_2$/γ-$CH_2$/δ-$CH_2$-Lys/$CH_2$-Pro (2×2H)); 2.63–3.63 (dm, 2H, N—$CH_2$-Pro); 2.96 (m, 2H, ε-$CH_2$-Lys); 3.17 (m, 2H, β-$CH_2$-Phe); 4.33 (m, 1H, α-CH-Pro); 4.43 (m, 2H, α-CH-Lys/α-CH-Phe); 7.30–7.39 (m, 5H, arom Phe); 7.93/7.95–8.21/8.23 (dd, 4H, arom pNA).

c) n=1, X=NZe (2b)

Yield: 0.167 g (75%), $R_f$(BuOH/AcOH/$H_2O$ 4:1:1 v/v/v): 0.80, $[\alpha]_D$=−125.0° C.=0.16 MeOH, $^1$H NMR ($CD_3OD$): δ=0.94 (t, 3H, ε-$CH_3$-Nle); 1.36–1.51 (bm, 8H, γ-$CH_2$/δ-$CH_2$-Nle/$CH_2$-Pro (2×2H)); 1.75–1.94 (bm, 2H, β-$CH_2$-Nle); 2.68/3.51 (dm, 2H, N—$CH_2$-Pro); 3.01 (m, 2H, β-$CH_2$-Phe); 4.09 (m, 1H, α-CH-Pro); 4.31 (m, 1H, α-CH-Nle); 4.41 (m, 1H, α-CH-Phe); 7.25–7.36 (m, 5H, arom Phe); 7.88/7.91–8.20/8.23 (dd, 4H, arom pNA).

Boc-X-Arg-pNA.HCl a) X=Gly

Boc-Gly-OH (1.75 g, 10 mmol), 2HCl.H-Arg-pNA (3.67 g, 10 mmol, 1.0 eq.), HOBt (1.60 g, 10.1 mmol, 1.01 eq.) and NMM (1.10 mL, 10.0 mmol, 1.0 eq.) were dissolved in DMF (75 mL). This reaction mixture was cooled on ice and DCC (2.16 g, 10.5 mmol, 1.05 eq.) was added. After stirring for one hr at 0° C. and 16 hrs at room temperature, DCU was filtered off and DMF was removed under reduced pressure. The residue was purified by counter current distribution with BuOH/AcOH/$H_2O$ 4:1:5 v/v/v (K=1.84) as the solvent system. After work-up the pure product was lyophilized from AcOH. Yield: 4.29 g (88%), $R_f$(BuOH/AcOH/$H_2O$ 4:1:1 v/v/v): 0.64, $[\alpha]_D$=−36.8° C.=0.63 MeOH.

b) X=Ala

Boc-Ala-ONSu (2.91 g, 10.14 mmol, 1.01 eq.) was coupled to 2HCl.H-Arg-pNA (3.69 g, 10.05 mmol) in the presence of DIPEA (1.83 mL, 10.5 mmol, 1.04 eq.) in 75 mL DMF. After 16 hrs of stirring at room temperature, DMF was removed under reduced pressure and the residue was diluted with BuOH (75 mL). The BuOH solution was washed with $H_2O$, saturated $NaHCO_3$, $H_2O$ and saturated NaCl (four times 20 mL each). The organic layer was evaporated in vacuo. The residue was purified by counter current distribution with the solvent system BuOH/AcOH/ $H_2O$ 4:1:5 v/v/v. The pure product was lyophilized from AcOH. Yield: 4.06 g (81%), $R_f$(BuOH/AcOH/$H_2O$ 4:1:1 v/v/v): 0.62, $[\alpha]_D$=−44.5° C.=0.72 MeOH, $^1$H NMR ($D_2O$/$CD_3OD$ 3:1 v/v): δ=0.83 (d, 3H, β-$CH_3$-Ala (J=7.14 Hz)); 0.92 (s, 9H, Boc); 1.29 (m, 4H, γ-$CH_2$-Arg/β-$CH_2$-Arg); 2.78 (m, 2H, δ-$CH_2$-Arg); 3.60 (q, 1H, α-CH-Ala); 4.04 (m, 1H, α-CH-Arg); 7.20/7.30–7.72/7.82 (dd, 4H, arom pNA).

c) X=D-Ala

Obtained as described for b)

Quantities used: Boc-D-Ala-ONSu: 1.43 g (5.0 mmol), 2HCl.H-Arg-pNA: 1.84 g (5.0 mmol), DIPEA: 1.92 mL (11.0 mmol, 2.2 eq.) in 30 mL DMF. Yield: 1.76 g (70%), $R_f$(BuOH/AcOH/$H_2O$ 4:1:1 v/v/v): 0.59 (K=1.93), $[\alpha]_D$=−47.0° C.=0.77 MeOH, $^1$H NMR ($CD_3OD$): δ=1.33 (d, 3H, β-$CH_3$-Ala (J=7.12 Hz)); 1.43 (s, 9H, Boc); 1.71 (m, 2H, γ-$CH_2$-Arg); 1.80/2.06 (dm, 2H, β-$CH_2$-Arg); 3.22 (m, 2H, δ-$CH_2$-Arg); 4.07 (q, 1H, α-CH-Ala (J=7.12 Hz)); 4.56 (m, 1H, α-CH-Arg); 7.92/7.94–8.20/8.22 (dd, 4H, arom pNA).

d) X=Val

Obtained as described for b)

Quantities used: Boc-Val-ONSu: 1.57 g (5.0 mmol), 2HCl.H-Arg-pNA: 1.80 g (5.0 mmol), DIPEA: 1.92 mL in 30 mL DMF. Yield: 2.36 g (89%), $R_f$(BuOH/AcOH/$H_2O$ 4:1:1 v/v/v): 0.69 (K=2.11), $[\alpha]_D$=−44.4° C.=0.59 MeOH, $^1$H NMR ($CD_3OD$): δ=0.94–0.98 (dd, 6H, γ-$CH_3$/γ'-$CH_3$-Val); 1.44 (s, 9H, Boc); 1.70 (m, 1H, β-CH-Val); 1.82 (m, 2H, γ-$CH_2$-Arg); 2.03 (m, 2H, β-$CH_2$-Arg); 3.23 (m, 2H, δ-$CH_2$-Arg); 3.88 (d, 1H, α-CH-Val); 4.56 (m, 1H, α-CH-Arg); 7.84/7.86–8.20/8.22 (dd, 4H, arom pNA).

e) X=D-Val

Obtained as described for b)

Quantities used: Boc-D-Val-ONSu: 1.57 g (5.0 mmol), 2HCl.H-Arg-pNA: 1.80 g (5.0 mmol), DIPEA: 1.92 mL in 30 mL DMF. Yield: 1.93 g (73%), $R_f$(BuOH/AcOH/$H_2O$ 4:1:1 v/v/v): 0.68 (K=2.59), $[\alpha]_D$=−50.6° C.=0.88 MeOH, $^1$H NMR ($CD_3OD$): δ=0.98–1.01 (dd, 6H, γ-$CH_3$/γ'-$CH_3$-Val); 1.42 (s, 9H, Boc); 1.66–1.80 (bm, 3H, β-$CH_2$-Arg(1H)/γ-$CH_2$-Arg); 1.99–2.09 (bm, 2H, β-$CH_2$-Arg(1H)/β-CH-Val); 3.23 (m, 2H, δ-$CH_2$-Arg); 3.79 (d, 1H, α-CH-Val); 4.56 (m, 1H, α-CH-Arg); 7.93/7.95–8.20/8.22 (dd, 4H, arom pNA).

2HCl.H-X-Arg-pNA

Protected dipeptides were dissolved in AcOH (1 mmol in 2 mL) and to this solution 2.3 M HCl in EtOAc (5 mL for 1 mmol) was added. The resulting solution was stirred for 2.5 hrs at room temperature. After acid quenching with tert.-BuOH (10 mL for 1 mmol) the solution was evaporated in vacuo and residual solvents were removed by coevaporation with tert.-BuOH (two times 10 mL) and with MeOH. The residue was dissolved in $H_2O$ (10 mL for 1 mmol) and washed with EtOAc (three times). The resulting aqueous solution was lyophilized. When necessary the product was purified by counter current distribution with the solvent system: BuOH/AcOH/$H_2O$ 4:1:5 v/v/v.

a) X=Gly (3)

Yield: 0.360 g (85%), $R_f$(BuOH/AcOH/$H_2O$ 4:1:1 v/v/v): 0.29 (K=0.62), $[\alpha]_D$=−14.1° C.=0.75 MeOH, $^1$H NMR ($D_2O$): δ=1.58 (m, 4H, β-$CH_2$/γ-$CH_2$-Arg); 2.92 (m, 2H, δ-$CH_2$-Arg); 3.63 (s, 2H, $CH_2$-Gly); 4.21 (m, 1H, α-CH-Arg); 7.27/7.37–7.80/7.89 (dd, 4H, arom pNA).

b) X=Ala (4)

Yield: 0.407 g (93%), $R_f$(BuOH/AcOH/$H_2O$ 4:1:1 v/v/v): 0.33 (K=0.36), $[\alpha]_D$=−5.5° C.=0.24 MeOH, $^1$H NMR ($D_2O$): δ=1.32 (d, 3H, β-$CH_3$-Ala (J=7.1 Hz)); 1.62 (m, 4H, β-$CH_2$/γ-$CH_2$-Arg); 2.99 (m, 2H, δ-$CH_2$-Arg); 3.89 (q, 1H, α-CH-Ala (J=7.1 Hz)); 4.31 (m, 1H, α-CH-Arg); 7.44/7.54–8.01/8.10 (dd, 4H, arom pNA).

c) X=D-Ala (5)

Yield: 0.385 g (88%), $R_f$(BuOH/AcOH/$H_2O$ 4:1:1 v/v/v): 0.33, $[\alpha]_D$=−26.8° C.=0.40 MeOH, $^1$H NMR ($D_2O$): δ=1.29 (d, 3H, $CH_3$-Ala (J=7.1 Hz)); 1.54 (m, 4H, β-$CH_2$/γ-$CH_2$-Arg); 2.96 (m, 2H, δ-$CH_2$-Arg); 3.91 (q, 1H, α-CH-Ala (J=7.1 Hz)); 4.24 (m, 1H, α-CH-Arg); 7.33/7.42–7.85/7.94 (dd, 4H, arom pNA).

d) X=Val (6)

Yield: 0.401 g (86%), $R_f$(BuOH/AcOH/$H_2O$ 4:1:1 v/v/v): 0.40, $[\alpha]_D$=−5.7° C.=0.21 MeOH, $^1$H NMR ($CD_3OD$): δ=1.05/1.07–1.08/1.10 (dd, 6H, γ-$CH_3$/γ'-$CH_3$-Val); 1.70–1.89 (m, 3H, γ-$CH_2$-Arg/β-CH-Val); 1.96/2.25 (dm, 2H, β-$CH_2$-Arg); 3.26 (m, 2H, δ-$CH_2$-Arg); 3.82 (d, 1H, α-CH-Val); 4.58 (m, 1H, α-CH-Arg); 7.85/7.87–8.20/8.22 (dd, 4H, arom pNA).

e) X=D-Val (7)

Yield: 0.447 g (96%), $R_f$(BuOH/AcOH/$H_2O$ 4:1:1 v/v/v): 0.40, $[\alpha]_D$=−40.8° C.=0.25 MeOH, $^1$H NMR ($D_2O$): δ=0.69/0.76 (dd, 6H, γ-$CH_3$/γ'-$CH_3$-Val); 1.44–1.51 (m, 4H, γ-$CH_2$/β-$CH_2$-Arg); 1.90 (m, 1H, β-CH-Val); 2.91 (m, 2H, δ-$CH_2$-Arg); 3.60 (d, 1H, α-CH-Val); 4.22 (m, 1H, α-CH-Arg); 7.26/7.35–7.76/7.86 (dd, 4H, arom pNA).

R-X-Arg-pNA.HCl

The monomethyl ester of the malonic acid derivative was coupled with DCC/HOBt with 2HCl.H-X-Arg-pNA in the presence of DIPEA for one hour at 0° C. and 16 hrs at room temperature (or as ONSu active ester in the presence of 1 eq. DIPEA). After filtration, the clear DMF solution was evaporated in vacuo. The residue was purified by counter current distribution with the solvent system: BuOH/AcOH/$H_2O$ 4:1:5 v/v/v. The pure product was lyophilized from $H_2O$.

a) R=MZ, X=Gly (3a)

Quantities used: 2HCl.H-Gly-Arg-pNA: 0.557 g (1.31 mmol), malonic acid monomethyl ester: 0.31 g (2.62 mmol, 2.0 eq.), HOBt: 0.235 g (1.54 mmol, 1.17 eq.), DIPEA: 0.24 mL (1.38 mmol, 1.05 eq.) and DCC: 0.289 g (1.40 mmol, 1.07 eq.) in 10 mL DMF. Yield: 0.319 g (50%), $R_f$(BuOH/AcOH/$H_2O$ 4:1:1 v/v/v): 0.45 (K=0.85), $[\alpha]_D$=−16.2° C.=0.29 MeOH, $^1$H NMR ($D_2O$): δ=1.63 (m, 2H, γ-$CH_2$-Arg); 1.85 (m, 2H, β-$CH_2$-Arg); 3.16 (m, 2H, δ-$CH_2$-Arg); 3.47 (s, 2H, $CH_2$-malonic acid); 3.67 (s, 3H, $OCH_3$); 3.96 (s, 2H, $CH_2$-Gly); 4.42 (m, 1H, α-CH-Arg); 7.55/7.57–8.07/8.09 (dd, 4H, arom pNA).

b) R=MZ, X=Ala (4a)

Quantities used: 2HCl.H-Ala-Arg-pNA: 0.438 g (1.0 mmol), malonic acid monomethyl ester: 0.158 g (1.34 mmol, 1.34 eq.), HOBt: 0.171 g (1.08 mmol, 1.08 eq.), DIPEA: 0.19 mL (1.05 mmol, 1.05 eq.) and DCC: 0.216 g (1.05 mmol, 1.05 eq.) in 10 mL DMF. Yield: 0.201 g (40%), $R_f$(BuOH/AcOH/$H_2O$ 4:1:1 v/v/v): 0.40 ( K=0.91), $[\alpha]_D$=−28.1° C.=0.26 MeOH, $^1$H NMR ($D_2O$): δ=1.35 (d, 3H, β-$CH_3$-Ala (J=7.2 Hz)); 1.65 (m, 2H, γ-$CH_2$-Arg); 1.79/1.90 (dm, 2H, β-$CH_2$-Arg); 3.17 (m, 2H, δ-$CH_2$-Arg); 3.43 (s, 2H, $CH_2$-malonic acid); 3.66 (s, 3H, $OCH_3$); 4.28 (q, 1H, α-CH-Ala (J=7.2 Hz)); 4.42 (m, 1H, α-CH-Arg); 7.57/7.59–8.09/8.11 (dd, 4H, arom pNA).

c) R=MZ, X=D-Ala (5a)

Quantities used: 2HCl.H-D-Ala-Arg-pNA: 0.183 g (0.419 mmol), 0.87 mL of 0.5 M MZ-ONSu in $CH_3CN$ (0.435 mmol, 1.04 eq.), DIPEA: 0.144 mL (0.838 mmol, 2.0 eq.) in 2 mL DMF. Yield: 0.101 g (48%), $R_f$(BuOH/AcOH/$H_2O$ 4:1:1 v/v/v): 0.45 (K=1.60), $[\alpha]_D$=−18.3° C.=0.18 MeOH, $^1$H NMR ($D_2O$): δ=1.26/1.33 (d, 3H, β-$CH_3$-Ala (J=7.2 Hz)); 1.60 (m, 4H, γ-$CH_2$/β-$CH_2$-Arg); 1.80 (s, 2H, $CH_2$-malonic acid); 3.10 (m, 2H, δ-$CH_2$-Arg); 3.58 (s, 3H, $OCH_3$); 4.23 (q, 1H, α-CH-Ala (J=7.2 Hz)); 4.32 (m, 1H, α-CH-Arg); 7.50/7.59–8.03/8.13 (dd, 4H, arom pNA).

d) R=MZ, X=Val (6a)

Quantities used: 2HCl.H-Val-Arg-pNA: 0.172 g (0.368 mmol), 0.76 mL of 0.5 M MZ-ONSu in $CH_3CN$ (0.38 mmol, 1.03 eq.), DIPEA: 0.126 mL (0.733 mmol, 1.99 eq.) in 2 mL DMF. Yield: 79.9 mg (41%), $R_f$(BuOH/AcOH/$H_2O$ 4:1:1 v/v/v): 0.57 (K=1.99), $[\alpha]_D$=−27.6° C.=0.21 MeOH, $^1$H NMR ($D_2O$): δ=0.79 (dd, 6H, γ-$CH_3$/γ'$CH_3$-Val); 1.54 (m, 2H, γ-$CH_2$-Arg); 1.70 (m, 1H, β-CH-Val); 1.80/1.94 (dm, 2H, β-$CH_2$-Arg); 3.06 (m, 2H, δ-$CH_2$-Arg); 3.34 (s, 2H, $CH_2$-malonic acid); 3.57 (s, 3H, $OCH_3$); 3.99 (d, 1H, α-CH-Val); 4.34 (m, 1H, α-CH-Arg); 7.52/8.07 (dd. 4H, arom pNA).

e) R=MZ, X=D-Val (7a)

Quantities used: 2HCl.H-D-Val-Arg-pNA: 0.183 g (0.393 mmol), 0.82 mL of 0.5 M MZ-ONSu in $CH_3CN$ (0.41 mmol, 1.04 eq.), DIPEA: 0.134 mL (0.78 mmol, 1.98 eq.) in 2 mL DMF. Yield: 70.8 mg (34%), $R_f$(BuOH/AcOH/$H_2O$ 4:1:1 v/v/v): 0.59 (K=2.10), $[\alpha]_D$=−35.3° C.=0.10 MeOH, $^1$H NMR ($D_2O$): δ=0.91/0.96 (dd, 6H, γ-$CH_3$/γ'-$CH_3$-Val); 1.62–2.11 (m, 5H, β-CH-Val/β-$CH_2$-Arg/γ-$CH_2$-Arg); 1.86 (s, 2H, $CH_2$-malonic acid); 3.19 (m, 2H, δ-$CH_2$-Arg); 3.62 (s, 3H, $OCH_3$); 4.07 (d, 1H, α-CH-Val); 4.43 (m, 1H, α-CH-Arg); 7.59/7.69–8.14/8.23 (dd, 4H, arom pNA).

f) R=MMZ, X=Gly (3b)

Quantities used: 2HCl.H-Gly-Arg-pNA: 0.557 g (1.31 mmol), methylmalonic acid monomethyl ester: 0.31 g (2.34 mmol, 1.79 eq.), HOBt: 0.228 g, (1.49 mmol, 1.14 eq.), DIPEA: 0.24 mL (1.38 mmol, 1.05 eq.) and DCC: 0.316 g (1.54 mmol, 1.17 eq.) in 10 mL DMF. Yield: 0.407 g (62%), $R_f$(BuOH/AcOH/$H_2O$ 4:1:1 v/v/v): 0.48 (K=1.18), $[\alpha]_D$=−16.9° C.=0.29 MeOH, $^1$H NMR ($D_2O$): δ=1.30–1.32 (d, 3H, $CH_3$-methylmalonic acid (J=7.0 Hz)); 1.63 (m, 2H, γ-$CH_2$-Arg); 1.80/1.91 (dm, 2H, β-$CH_2$-Arg); 3.16 (m, 2H, δ-$CH_2$-Arg); 3.58/3.61 (dq, 1H, CH-methylmalonic acid (J=7.0 Hz)); 3.65 (s, 3H, $OCH_3$); 3.95 (s, 2H, $CH_2$-Gly); 4.45 (m, 1H, α-CH-Arg); 7.55/7.57–8.06/8.08 (dd, 4H, arom pNA).

g) R=MMZ, X=Ala (4b)

Quantities used: 2HCl.H-Ala-Arg-pNA: 0.431 g (0.98 mmol), methylmalonic acid monomethylester: 0.22 g (1.67 mmol, 1.70 eq.), HOBt: 0.193 g, (1.26 mmol, 1.29 eq.), DIPEA: 0.19 mL (1.05 mmol, 1.07 eq.) and DCC: 0.243 g (1.18 mmol, 1.21 eq.) in 10 mL DMF. Yield: 0.283 g (56%), $R_f$(BuOH/AcOH/$H_2O$ 4:1:1 v/v/v): 0.46 (K=1.18), $[\alpha]_D$=−39.3° C.=0.29 MeOH, $^1$H NMR ($D_2O$): δ=1.28–1.40 (3×d, 6H, β-$CH_3$-Ala/$CH_3$-methylmalonic acid); 1.63 (m, 2H, γ-$CH_3$-Arg); 1.85/1.91 (dm, 2H, β-$CH_2$-Arg); 3.18 (m, 2H, δ-$CH_2$-Arg); 3.54 (dq, 1H, CH-methylmalonic acid); 3.60–3.68 (ds, 3H, $OCH_3$); 4.26 (q, 1H, α-CH-Ala); 4.42 (m, 1H, α-CH-Arg); 7.59/7.62–8.13/8.15 (dd, 4H, arom pNA).

h) R=DMMZ, X=Gly (3c)

Quantities used: 2HCl.H-Gly-Arg-pNA: 0.557 g (1.31 mmol), dimethylmalonic acid monomethyl ester: 0.52 g (3.57 mmol, 2.72 eq.), HOBt: 0.225 g, (1.47 mmol, 1.12 eq.), DIPEA: 0.24 mL (1.38 mmol, 1.05 eq.) and DCC: 0.291 g (1.41 mmol, 1.08 eq.) in 10 mL DMF. Yield: 0.492 g (73%), $R_f$(BuOH/AcOH/$H_2O$ 4:1:1 v/v/v): 0.49 (K=1.40), $[\alpha]_D$=−30.3° C.=0.45 MeOH, $^1H$ NMR ($D_2O$): δ=1.41 (s, 6H, $(CH_3)_2$-C-dimethylmalonic acid (2×3H)); 1.64 (m, 2H, γ-$CH_2$-Arg); 1.78/1.91 (dm, 2H, β-$CH_2$-Arg); 3.17 (m, 2H, δ-$CH_2$-Arg); 3.66 (s, 3H, $OCH_3$); 3.92 (s, 2H, $CH_2$-Gly); 4.45 (m, 1H, α-CH-Arg); 7.58/7.60–8.10/8.12 (dd, 4H, arom pNA).

i) R=DMMZ, X=Ala (4c)

Quantities used: 2HCl.H-Ala-Arg-pNA: 0.435 g (0.99 mmol), dimethylmalonic acid monomethyl ester: 0.22 g (1.51 mmol, 1.53 eq.), HOBt: 0.182 g, (1.19 mmol, 1.20 eq.), DIPEA: 0.19 mL (1.05 mmol, 1.06 eq.) and DCC: 0.245 g (1.19 mmol, 1.20 eq.) in 10 mL DMF. Yield: 0.283 g (54%), $R_f$(BuOH/AcOH/$H_2O$ 4:1:1 v/v/v): 0.52 (K=1.40), $[\alpha]_D$=−35.2° C.=0.28 MeOH, $^1H$ NMR ($D_2O$): δ=1.36 (d, 3H, β-$CH_3$-Ala (J=7.3 Hz)); 1.39 (s, 6H, $(CH_3)_2$-C-dimethylmalonic acid (2×3H)); 1.67 (m, 2H, γ-$CH_2$-Arg); 1.81/1.92 (dm, 2H, β-$CH_2$-Arg); 3.18 (m, 2H, δ-$CH_2$-Arg); 3.66 (s, 3H, $OCH_3$); 4.28 (q, α-CH-Ala (J=7.3 Hz)); 4.42 (m, 1H, α-CH-Arg); 7.59/7.62–8.12/8.14 (dd, 4H, arom pNA).

j) R=DEMZ, X=Gly (3d)

Quantities used: 2HCl.H-Gly-Arg-pNA: 0.419 g (0.99 mmol), diethylmalonic acid monomethyl ester: 0.30 g (1.72 mmol, 1.74 eq.), HOBt: 0.153 g, (1.0 mmol, 1.01 eq.), DIPEA: 0.182 mL (1.01 mmol, 1.02 eq.) and DCC: 0.206 g (1.0 mmol, 1.01 eq.) in 10 mL DMF. Yield: 0.398 g (74%), $R_f$(BuOH/AcOH/$H_2O$ 4:1:1 v/v/v): 0.57 (K=2.31), $[\alpha]_D$=−29.8° C.=0.27 MeOH, $^1H$ NMR ($D_2O$): δ=0.85 (t, 6H, $CH_3$~diethylmalonic acid (2×3H)); 1.59 (m, 4H, β-$CH_2$/γ-$CH_2$-Arg); 1.92 (q, 4H, ~$CH_2$~diethylmalonic acid (2×2H)); 3.19 (m, 2H, δ-$CH_2$-Arg); 3.79 (s, 3H, $OCH_3$); 3.92 (s, 2H, $CH_2$-Gly); 4.24 (m, 1H, α-CH-Arg); 7.25/7.32–7.64/7.73 (dd, 4H, arom pNA).

βNS-Gly-Arg-pNA.HCl (3e)

2HCl.H-Gly-Arg-pNA (0.2632 g, 0.621 mmol) was dissolved in dry pyridine (10 mL). To this solution were added DIPEA (120 μL, 0.689 mmol, 1.11 eq.) and β-naphtalenesulfonyl chloride (0.1588 g. 0.701 mmol, 1.13 eq.). The obtained reaction mixture was stirred overnight at room temperature. After completion of the reaction, pyridine was removed under reduced pressure and the oily residue was coevaporated with toluene (twice) and MeOH (once). The foamy residue was purified by counter current distribution with the solvent system: BuOH/AcOH/$H_2O$ 4:1:5 v/v/v. The pure product was lyophilized from AcOH. Yield: 0.211 g (59%), $R_f$(BuOH/AcOH/$H_2O$ 4:1:1 v/v/v): 0.67 (K=7.13), $[\alpha]_D$=−39.5° C.=0.19 MeOH, $^1H$ NMR ($CD_3OD$): δ=1.59 (m, 2H, γ-$CH_2$-Arg); 1.74/1.95 (dm, 2H, β-$CH_2$-Arg); 3.16 (m, 2H, δ-$CH_2$-Arg); 3.66 (dd, 2H, $CH_2$-Gly); 4.47 (m, 1H, α-CH-Arg); 7.58–7.66 (m, 2H, arom βNS); 7.78/7.80 (d, 2H, arom pNA); 7.84–8.03 (m, 4H, arom βNS); 8.16/8.18 (d, 2H, arom pNA); 8.45 (s, 1H, arom βNS).

pTS-Gly-Arg-pNA.HCl (3f)

Obtained as described for βNS-Gly-Arg-pNA.HCl

Quantities used: 2HCl.H-Gly-Arg-pNA: 0.2717g (0.641 mmol); DIPEA: 124 μL (0.712 mmol, 1.11 eq.); p-toluenesulfonyl chloride: 0.1352 g (0.709 mmol, 1.11 eq.) in 10 mL pyridine. Yield: 0.211 g (63%), $R_f$(BuOH/AcOH/$H_2O$ 4:1:1 v/v/v): 0.71 ( K=4.38), $[\alpha]_D$=−34.0° C.=0.15 MeOH, $^1H$ NMR ($CD_3OD$): δ=1.65 (m, 2H, γ-$CH_2$-Arg); 1.78/1.96 (dm, 2H, β-$CH_2$-Arg); 2.36 (s, 3H, $CH_3$); 3.21 (m, 2H, δ-$CH_2$-Arg); 3.59 (dd, 2H, $CH_2$-Gly); 4.55 (m, 1H, α-CH-Arg); 7.37/7.39–7.74/7.77 (dd. 4H, arom tosyl); 7.84/7.87–8.20/8.22 (dd, 4H, arom pNA).

REFERENCES

26. König, W. and Geiger, R. (1970) *Chem. Ber.* 103, 788–798.

27. Curtius, Th. (1902) Ber. dtsch. *Chem. Ges.* 35, 3226–3228.

28. Honzl, J. and Rudinger, J. (1961) *Coll. Czech. Chem. Commun.* 26, 2333–2344.

29. (a) Craig, L. C. (1944) *J. Biol. Chem.* 155, 519–534; (b) Craig, L. C., Hausmann, W., Ahrens, E. H. jr. and Harfenist, E. J. (1951) *Anal. Chem.* 23, 1236–1244.

30. Hecker, E. (1955) In: *Verteitungsverfahren im Laboratorium*, Verlag Chemie GmbH, Weinheim-Bergstrasse, Germany.

31. Schnabel, E. (1967) *Liebigs Ann. Chem.* 702, 188–196.

32. Anderson, G. W., Zimmerman, J. F. and Callahan, F. M. (1964) *J. Am. Chem. Soc.* 86, 1839–1842.

33. In: *The Chemistry of the Amino Acids* (1961) Greenstein, J. P. and Winitz, M. (Eds.) 3, 2538–2539, John Wiley and Sons Inc., New York, U.S.A.

34. In: *Vogel's Textbook of Organic Chemistry* (1989) Furniss, B. S. et at. (Eds.) $5^{th}$ edition, 680; 697, Longman Scientific and Technical, Essex, England.

35. Breslow, D. S., Baumgarten, E. and Hauser, C. R. (1944) *J. Am. Chem. Soc.* 66, 1286–1288.

EXAMPLE 2

The Application of Peptide p-Nitroanilides in the Continuous Registration of Thrombin Generation in Plasma This example describes the biochemical evaluation of a set of substrates which could be used in the continuous registration of thrombin formation in plasma.

Materials and Methods

Materials

Chromogenic substrates: The syntheses of the substrates are described in Example 1. The preparation of Boc-Gly-Val-Arg-pNA.HCl and 2HCl.H-Gly-Val-Arg-pNA is described in elsewere. The substrates were dissolved in distilled water to obtain 10 mM stock solutions. The concentration was determined at 316 nm using a molar extinction coefficient of 12,500. Stock solutions were stored in the dark at 4° C. Factor Xa substrate methyloxycarbonyl-D-cyclohexylglycyl-glycyl-arginine p-nitroanilide acetate ($CH_3O$—CO-D-Chg-Gly-Arg-pNA.AcOH) was obtained from Pentapharm (Basel, Switzerland). Thrombin substrate SQ68 (malonyl-α-aminoisobutyryl-arginine p-nitroanilide methyl ester monohydrochloride, $CH_3O$—CO—$CH_2$—CO-Aib-Arg-pNA.HCl) was purchased from Serbio Laboratories, France.

Phospholipids: Phospholipids required were 80 mol-% dioleoyl phosphatidyl choline and 20 mol-% dioleoyl phosphatidyl serine solutions in chloroform; they were obtained from Avanti Polar Lipids. They were used to prepare vesicles as described by Rosing et al.[6]

Buffers: Buffer A: 0.05 M Tris-HCl, 0.1 M NaCl pH=7.35 containing 0.5 g/L bovine serum albumin (Sigma). Buffer B: buffer A containing additional EDTA (20 mM), pH=7.90.

Enzyme preparations: Pure human α-thrombin and human factor Xa samples were generous gifts of Dr. T. Lindhout (University of Limburg, Maastricht, The Netherlands). The euglobulin thrombin fraction was prepared from defibrinated human plasma by acid precipitation at low ionic strength as described by Josso and Prou-Wartelle[7]. The precipitate was dissolved in half the original volume of buffer A, containing 0.02 M trisodium citrate.

Plasma: Plasma was prepared by collecting 9 parts of blood (from 10 healthy donors) on 1 part of 0.13 M trisodium citrate. Following centrifugation at 900 g (15° C., 15 min) and 10,000 g (15° C., 15 min) the obtained plasma was pooled and centrifuged at 4° C. for 1 hour at 23,000 g; this plasma was stored at −80° C. Plasma was defibrinated by mixing an aliquot of plasma with 1/50 volume of reptilase (Laboratories Stago, Asnières, France; the solution was made as instructed by the manufacturer), letting a clot form for 10 min at 37° C. followed by 10 min on ice. The fibrin clot was removed by winding it on a plastic spatula.

Tissue factor: Recombinant tissue factor (RECOMPLASTIN S, Dade, Baxter Diagnostics Inc., Deerfield Ill., U.S.A.) was used as a trigger for coagulation. The solution was prepared according to the instructions of the manufacturer. The intrinsic pathway was triggered by Actin FS, activated PTT reagent from soy phosphatides, containing $1.10^{-4}$ M ellagic acid and was obtained from Baxter.

Methods

Kinetic parameters: The hydrolysis experiments were run in buffer A at 37° C. The liberation of p-nitroaniline was monitored at 405 nm in a dual wavelength (405–546 nm) spectrophotometer made in our workshop, using a personal computer for data recording. In a polystyrene microcuvette (total volume 500 μL), buffer A and substrate solution were added to obtain a final substrate concentration between 1 to 2000 μM. After 5 min of incubation at 37° C., enzyme solution was added to achieve a final concentration between 0.5 to 100 nM. The measurement was carried out at 37° C. in a thermostated cuvette-holder. The Michaelis constant ($K_m$) and the catalytic constant ($k_{cat}$) were obtained by measuring initial reaction velocities at different substrate concentrations. The data obtained were fitted by linear regression on the Michaelis-Menten equation.

Factor Xa inhibition experiments[8]: In a polystyrene microcuvette were added: buffer A (the substrate to be tested on inhibitory effects on factor Xa in the concentration range between 0 to 1000 μM), the chromogenic substrate $CH_3O$—CO-D-Chg-Gly-Arg-pNA.AcOH at a concentration of 100 μM and factor Xa at a concentration of 1.0 nM. In an other fashion the inhibitor (the substrate to be tested) concentration was kept at 250 μM and the chromogenic substrate concentration ($CH_3O$—CO-D-Chg-Gly-Arg-pNA.AcOH) was varied between 25 to 1000 μM at the same enzyme concentration. Both measurements were carried out in a total volume of 500 μL at 37° C. Optical density was measured as above.

Continuous registration of the thrombin generation curve: Extrinsic pathway: In a polystyrene microcuvette were added: 400 μL defibrinated plasma, 20 μL of a 45 μM phospholipid solution (final concentration: 1.5 μM), 140 μL of buffer A which contains the substrate at the desired final concentration (100–2000 μM). After 4 min of incubation at 37° C., 20 μL tissue factor (undiluted) was added. Thrombin generation was started by adding 20 μL of a 0.5 M $CaCl_2$ solution (final concentration: 16.67 mM); during the measurement the temperature was kept at 37° C. The optical density was monitored at 405 nm. From the obtained optical density curve, the first derivative was calculated. This gives the enzyme concentration during the measurement. Intrinsic pathway: 400 μL defibrinated plasma, 110 μL buffer A (eventually containing the substances to be tested) and 40 μL Actin FS (undiluted) were added in a plastic microcuvette, intensively mixed and incubated at 37° C. during 4 min. Then 30 μL of a 10 mM substrate solution (final concentration: 500 μM), followed by 20 μL of a 0.5 M $CaCl_2$ solution (final concentration: 16.7 mM) were added (both solutions were prewarmed at 37° C. for 4 min). The optical density was measured at 37° C. at 405 nm during 20 min.

Decay constants of thrombin in plasma: To 120 μL defibrinated plasma was added: 50 μL of buffer A which contained the substrate at a concentration range between 0 to 2000 μM. To this mixture was added 10 μL of a thrombin preparation to achieve a final concentration of 100 nM. At regular time intervals (5–10 s) 10 μL samples were subsampled into 490 μL buffer B which contained 200 μM of S2238 to determine thrombin activity. After 2 min the reaction was stopped by adding 300 μL 1M citric acid. The moment of sampling and stopping were recorded on a personal computer with pushbutton-equipped pipettes. The optical density was then read at 405 nm and the obtained amidolytic activities were used to calculate the decay constants. The obtained decay constant is the sum of the decay constants of the reaction of thrombin with antithrombin III ($k_1$) and $\alpha_2$-macroglobulin ($k_2$).

Manual determination of thrombin generation in plasma: Extrinsic pathway: To 480 μL defibrinated plasma were added: 172 μL buffer A which contains the substrate at concentrations between 0 to 2000 μM and 20 μL of a 54 μM phospholipid solution (final concentration: 1.5 μM). After incubation of 4 min at 37° C., 24 μL tissue factor (undiluted) was added. Thrombin formation started at zero time by adding 24 μL of a 0.5 M $CaCl_2$ solution (final concentration: 16.67 mM). At regular time intervals of 12 s samples of 10 μL were subsampled as described above. From the amidolytic activities thus obtained, the thrombin generation curve can be drawn. The decay constant $k_2$ can be calculated from these data in an alternatively way, see reference 9 for further details. Intrinsic pathway: To 480 μL defibrinated plasma were added: 168 μL buffer A which contains the substrate at concentrations between 0 to 1000 μM and 48 μL Actin FS (undiluted). This mixture was intensively mixed and incubated for 4 min at 37° C. Thrombin generation was started at zero time by adding 24 μL of a 0.5 M $CaCl_2$ solution (final concentration: 16.67 mM).

Influence of the substrate on the prothrombinase-complex: With the obtained decay constants and from the curves obtained by the subsampling method we calculated the course of prothrombin conversion and the course of prothrombinase concentration.

Results

Kinetic parameters: In a preliminary experiment, the substrate was hydrolyzed under the following conditions: enzyme concentration: 10 to 20 nM, substrate concentration: 200 μM in buffer A to get an impression of the initial velocity. From these data (not shown) the conditions at which the substrate was hydrolyzed to obtain the kinetic parameters $K_m$ and $k_{cat}$ were selected. The results are given in table 1 and 2 for thrombin and factor Xa respectively. The $K_m$ and $k_{cat}$ for each substrate were determined from the initial velocities measured for at least six substrate concentrations in the concentration range as given. The enzyme concentration used gives a good signal to noise ratio. The data given are obtained from one or two experiments. The data from table 1 and 2 were only used as the first selection criterion to get a rough impression of the hydrolysis behaviour. Notwithstanding the preliminary character of the measurement it was helpful in the design of the substrates of our interest. The narrow substrate concentration range used in entries 6, 7 and 25 is due to the restricted water solubility of the substrates.

Continuous registration of the thrombin generation curve: After application of the first two selection criteria only four substrates (entries: 5, 8, 12 and 22) were selected for evaluation in the continuous registration of thrombin formation in plasma, see FIGS. 6–14 and compared to SQ68, our reference. All of them show the characteristic thrombin generation curve, but the signal to noise ratio and the degree of substrate conversion is strongly substrate dependent. On basis of a low degree of substrate conversion when thrombin formation is over and a reasonable signal to noise ratio only one substrate (entry 12: 2HCl.H-Val-Arg-pNA) remained. The continuous thrombin generation curves triggered by Actin FS are given for SQ68 (reference) and 2HCl.H-Val-Arg-pNA, see FIG. 15.

Decay constants of thrombin in plasma: The decay of thrombin in a plasma sample gives information about the influence of the substrate on the efficiency of antithrombin III. AT-III as well as substrate compete for the active-site of thrombin. In the presence of substrate, thrombin decay must be minimally influenced by substrate, that means thrombin decay in the presence of substrate should be approximately the same as in the control experiment. In table 6 the data of thrombin decay in the presence of substrate 2HCl.H-Val-Arg-pNA are given. Compared to the decay constants of SQ68 (given in reference 1) it can be concluded that 2HCl.H-Val-Arg-pNA interferes to a lesser extent with AT-III. This is in agreement with a higher $K_m$ value which is inversely proportional to competitive interaction with AT-III.

Manual determination of thrombin formation in plasma and the influence of substrate on the prothrombinase-complex: The thrombin generation curves obtained by the subsampling method are given in FIGS. 16 and 17. As can be seen the peak of the curve is shifted to the right at increasing substrate concentration. This unfortunately means that the maximum of thrombin concentration is at a later point of time. The maximum of the curve increases at increasing substrate concentration due to the diminished action of antithrombin III in the presence of substrate. The $\alpha_2$-macroglobulin concentration in each of the four cases is the same, from these data $k_2$ can be determined in an alternative way, the obtained decay constants are shown in table 6.

From the velocity of thrombin formation and the decay constants, the activity of the prothrombinase-complex can be calculated, the results are shown in FIG. 7. As can be seen these curves have a lower maximum. The thrombin generation curves obtained by activating the intrinsic pathway are given in FIGS. 9 and 10.

REFERENCES

1. Hemker, H. C., Wielders, S., Kessels, H. and B_guin, S. (1993) *Thromb. Haemostas.* 70, 617–624.
6. Rosing, J., Tans, C., Govers-Riemslag, J. W. P., Zwaal, R. F. A. and Hemker, H. C. (1980) *J. Biol. Chem.* 255, 274–283.
7. Josso, F. and Prou-Wartelle, O. (1972) In: *Techniques en hematozogie*, Alagille, D. et al. (Eds.), 101–108, Paris, France.
8. Orthner, C. L., Morris, S. and Kosow, D. P. (1981) *Thromb. Res.* 23, 533–539.

EXAMPLE 3

The Synthesis of Chromogenic Substrates Fitting Thrombin

Abstract

A series of 18 peptide p-nitroanilides was synthesized. The lead structure was derived from human fibrinogen Aα(7-16) decapeptide since this fragment constitutes the minimal sequence which binds to thrombin with high affinity. In this sequence Glu11 participates in an important salt-bridge to Arg173 of thrombin; Gly12 is involved in a type II β-turn enabling the fold-back of the side chains of Phe8 and Leu9 for interaction with the active-site. The role of the guanidinium group in Arg16 was considered by the exchange of this residue against Lys, Orn or Nle in the C-terminal tripeptide p-nitroanilides. We similarly considered the glycyl-spacer by extension of the fragment Glu-$(Gly)_n$-Val-Arg16-pNA (SEQ ID NO: 4) to three units and stepwise shortening to zero, respectively by replacement of Gly12 or Gly13 of the extended chain by Pro, to mimic a β-turn. Finally, the N-terminus of the substrate Val-Arg-pNA was substituted with the polar 2-(methylsulfonylethyl) oxycarbonyl group (Msc) whilst the arginine residue was substituted for Lys, Orn or Nle. Using the methods described in example 1, a general racemization-free synthesis was developed for compounds of the type: Y-Val-X-pNA. The compounds synthesized in this study are given in table 7.

The substrates are defined herein as valine derivatives, since this aminoacyl residue, occurring in the P2 position and fits the S2 pocket of thrombin fairly well. In the series studied, the amino group of valine is either protonated or substituted either with a slim, polar aminoprotective function (Msc)[18], or with acyl(peptidyl) groups of variable bulkiness, length and polarity.

The structure of these substrates is incompatible with the S2 pocket of factor Xa which is so narrow that only glycyl in position P2 will fit[19]. The importance of the conspicuous glycyl-spacer (positions 12–14) in the substrate, which can attain a β-turn, was studied. As the second approach to affect the $K_m$ by modification of the linker length and its flexibility (compounds 3a–g); the peptide chain was changed by insertion of Pro as a constraint either in position 13 (P4, 3h) or in position 12 (P5, 3i), cf. Kahn[20]. Variation of the length of the glycyl-spacer, affects the ability to form the salt-bridge between Glu11 and Arg173 in thrombin and this would be revealed by the value of the $K_m$. Proline is known to facilitate the formation of a β-turn and might thus replace the hydrophobic binding exerted by the residues Phe8 and Leu9, which causes the reversal of the peptide backbone and the formation of the salt-bridge.

Methods of Synthesis

Syntheses with nitroanilides are incompatible with conditions which attack or remove the nitroanilide function; these are: treatment with strong bases for hydrolysis or β-elimination, hydrazinolysis and catalytic hydrogenolysis. The necessary protective functions should be removable using conditions compatible with the conservation of the nitroanilide moiety. Excluded are thus the use of OMe and OEt for carboxyl protection, Msc for amino protection, preactivation of carboxylic functions with hydrazine hydrate and finally, application of most of the members of the benzyl "family". Acidolysis is compatible with the conservation of the nitroanilide function.

Strict conservation of the chirality of aminoacyl residues excludes the activation of N-protected peptides with C-termini other than Gly or Pro. It is therefore risky to convert an existing peptide into a nitroanilide. The approaches which are compatible with this condition are stepwise elongation of the chain using activated N-protected amino acids and/or fragment condensation using azides to acylate an existing amino acid p-nitroanilide. Azides are often used to evade racemization during fragment condensations, on condition that neutral conditions are maintained and use is made of sterically hindered bases (DIPEA) to effect this.

Compounds of the type 1 and 2 (see table 7) were obtained by acylation of the α-amino function of the partially protected nitroanilide X with the active ester Boc-Val-ONSu, removal of the N-protection by acidolysis (1a), subsequent acylation with monomethyl malonate (2) or by acylation with Msc-Val-ONp (2a), respectively Msc-Val-ONSu (2b–d). Compounds of type 3 were obtained by acylation of the α-amino group of the nitroanilide X with acylated valine azides and subsequent treatment with acid (3, 3a–c), see scheme 1.

Boc-Val-ONSu + 2HCl.H-Arg-pNA -i-> Boc-Val-Arg-pNA.HCl -ii-> 2HCl.H-Val-Arg-pNA (1) -iii-> MZ-Val-Arg-pNA.HCl (2)
Boc-Val-ONSu + H-Lys(Boc)-pNA -i-> Boc-Val-Lys(Boc)-pNA -ii-> 2HCl.H-Val-Lys-pNA (1a)

Scheme 1A:
i) DIPEA in DMF;
ii) HCl in EtOAc/AcOH 1:1 v/v;
iii) malonic acid monomethyl ester, DCC/HOBt/DIPEA in DMF.

Msc-ONSu + H-Val-OH -i-> Msc-Val-OH -ii->/
-iii-> Msc-Val-ONSu/Msc-Val-ONp
Msc-Val-ONp + 2HCl.H-Arg-pNA -iv-> Msc-Val-Arg-pNA.HCl (2a)
Msc-Val-ONSu + H-Lys(Boc)-pNA -iv-> Msc-Val-Lys(Boc)-pNA -v-> Msc-Val-Lys-pNA.HCl (2b)
Msc-Val-ONSu + HCl.H-Orn(Boc)-pNA -iv-> Msc-Val-Orn(Boc)-pNA -v-> Msc-Val-Orn-pNA.HCl (2c)
Msc-Val-ONSu + HCl.H-Nle-pNA -iv-> Msc-Val-Nle-pNA (2d)

Scheme 1B:
i) TEA in $CH_3CN/H_2O$ 4:1 v/v;
ii) DCC/HONSu;
iii) DCC/HONp;
iv) TEA in DMF;
v) HCl in EtOAc/AcOH 1:1 v/v.

Compounds representing a modified glycyl-spacer were obtained by acylation of compound 1 and 3 respectively (see scheme 2) with Boc-Glu(O$^t$Bu)-ONSu and subsequent acidolysis (3d,e). Similarly, the introduction of Boc-Glu(O$^t$Bu)-Gly-ONSu into compound 3 afforded the substrate with the shortened glycyl-spacer (3f). The introduction of the complete glycyl-spacer was performed by acylation of 3 with Boc-Gly-Gly-ONSu, removal of the Boc-group and acylation with Boc-Glu(O$^t$Bu)-ONSu (3g). The modified spacers were inserted using the same route, replacing Boc-Gly-Gly-ONSu by Boc-Gly-Pro-ONSu (3h) or Boc-Pro-Gly-ONSu (3i). Deprotection of compounds containing the Boc-Glu(O$^t$Bu) moiety (3d–i) was performed using Sieber's method[21], to evade incomplete reactions as a consequence of the induced field effect by $N^\alpha$.

Boc-Gly-OH + HCl.H-Val-OMe -i->
Boc-Gly-Val-OMe -ii-> Boc-Gly-Val-$N_2H_3$

| | |
|---|---|
| -iii-> | Boc-Gly-Val-Arg-pNA.HCl (3') -iv-> 2HCl.H-Gly-Val-Arg-pNA (3) |
| -iii-> | Boc-Gly-Val-Lys(Boc)-pNA -iv-> 2HCl.H-Gly-Val-Lys-pNA (3a) |
| -iii-> | Boc-Gly-Val-Orn(Boc)-pNA -iv-> 2HCl.H-Gly-Val-Orn-pNA (3b) |
| -iii-> | Boc-Gly-Val-Nle-pNA -iv-> HCl.H-Gly-Val-Nle-pNA (3c) |

Scheme 1C:
i) DCC/HOBt/DIPEA in EtOAc;
ii) $N_2H_4.H_2O$ in MeOH;

-continued

Boc-Gly-OH + HCl.H-Val-OMe -i->
Boc-Gly-Val-OMe -ii-> Boc-Gly-Val-$N_2H_3$ iii) 1. tert.-BuONO/HCl at −20° C., 2. DIPEA, 3. H-Xaa-pNA/DIPEA in DMF at 0° C.;
iv) HCl in EtOAc/AcOH 1:1 v/v.

2HCl.H-Val-Arg-pNA -i-> Boc-Glu(O$^t$Bu)-Val-Arg-pNA.HCl -ii-> 2HCl.H-Glu-Val-Arg-pNA (3d)

Scheme 2A:
i) Boc-Glu(O$^t$Bu)-ONSu, DIPEA in DMF;
ii) 37% HCl at 0° C. (SEQ ID NOS:5–13).

2HCl.H-Gly-Val-Arg-pNA -i->
Boc-Glu(O$^t$Bu)-Gly-Val-Arg-pNA.HCl -ii->
2HCl.H-Glu-Gly-Val-Arg-pNA (3e)
-iii-> Boc-Glu(O$^t$Bu)-Gly-Gly-Val-Arg-pNA.HCl -ii->
2HCl.H-Glu-Gly-Gly-Val-Arg-pNA (3f)
-iv> Boc-Glu(O$^t$Bu)-Gly-Gly-Gly-Val-Arg-pNA.HCl
-ii->
2HCl.H-Glu-Gly-Gly-Gly-Val-Arg-pNA (3g)
-v-> Boc-Glu(O$^t$Bu)-Gly-Pro-Gly-Val-Arg-pNA.HCl
-ii->
2HCl.H-Glu-Gly-Pro-Gly-Val-Arg-pNA (3h)
-vi-> Boc-Glu(O$^t$Bu)-Pro-Gly-Gly-Val-Arg-pNA.HCl -ii->
2HCl.H-Glu-Pro-Gly-Gly-Val-Arg-pNA (3i)

Scheme 2B:
i) Boc-Glu(O$^t$Bu)-ONSu, DIPEA in DMF;
ii) 37% HCl at 0° C. (SEQ ID NOS:14–16);
iii) Boc-Glu(O$^t$Bu)-Gly-ONSu, 2HCl.H-Gly-Val-Arg-pNA, DIPEA in DMF;
iv) Boc-Glu(O$^t$Bu)-ONSu, 2HCl.H-Gly-Gly-Gly-Val-Arg-pNA, DIPEA in DMF;
v) Boc-Glu(O$^t$Bu)-ONSu, 2HCl.H-Gly-Pro-Gly-Val-Arg-pNA, DIPEA in DMF;
vi) Boc-Glu(O$^t$Bu)-ONSu, 2HCl.H-Pro-Gly-Gly-Val-Arg-pNA, DIPEA in DMF.

Conclusion

The chromogenic substrates described in this chapter were synthesized by classical solution methods and were obtained in good yields. The N-terminal stepwise elongation of the peptide chain proved to be an efficient strategy for the rapid synthesis of tri-, tetra-, penta- and hexapeptides. Pentapeptides were synthesized by coupling of protected activated dipeptides to N-terminal deprotected tripeptides. The C-terminal glycine- or proline residues in the dipeptides were not prone to racemization during activation. The deprotection of the N-terminal Boc-Glu(O$^t$Bu)$^-$ residue was performed in concentrated hydrochloric acid in a very efficient way.

Experimental Procedures

General $^1$H NMR spectra were recorded on Bruker AM 100 and AM 400 spectrometers. As an internal standard the residual solvent peak was used. Chemical shifts are given in part per million (ppm). Optical rotations were measured on a Perkin Elmer 241 polarimeter in a 10 cm cuvette at room temperature. Melting points were determined with a Büchi melting point apparatus (Tottoli). Peptides (1 μmol) were hydrolysed in 5.7 M HCl (Merck SUPRAPUR 30% HCl) for 24 hrs at 120° C. and analysed on a Varian Star amino acid analyser. TLC was performed on Merck SILICAGEL $60F_{254}$ plates, and column chromatography on Merck KIESELGEL 60 70–230 Mesh ASTM. Spots were detected by UV-fluorescence quenching, ninhydrine (free amino functions), chlorine/TDM (NH groups), Barton's—(hydrazides) and Sakaguchi's (arginine residues) reagent. Boc-amino acids were synthesized by the method of Schnabel[22]. Amino acid methyl esters were prepared as their hydrochlorides by the method of Brenner and Huber[23]. Amino acid p-nitroanilides were synthesized as described in chapter 1. Arginine nitroanilide derivatives were never dried with anhydrous sulfates to prevent their crystallization as sulfates. Boc-Val-ONSu was from Bachem.

The synthesis of p-nitroanilides from paranitroaniline can occur in a number of manners described in the literature. The use of DCC[2]DCC/HOBt[3] or the mixed anhydride method[4] give yields in the range between 30–58%. Acid chlorides[5] or thermal activation[6] are recommended to overcome the low nucleophilicity of p-nitroaniline. As an alternative to p-nitroaniline, syntheses using pure p-nitrophenylisocyanate[7], are in situ generated from p-nitrobenzoic acid through the modified Curtius reaction with diphenyl phosphorazidate[8], are found to be general and efficient methods. Burdick et al[9] describe a synthesis of peptide p-nitroanilides using an urethane-linked p-aminoanilide resin in which the peptide is built up by SPPS. Reiter[10] describes the use of p-(Boc-amino)aniline as precursor for p-nitroaniline. The final oxidation step limits its practical use when methionine, tryptophan and cysteine are incorporated in the peptide. The first syntheses of tert-butyloxycarbonyl amino acid p-nitroanilides have been reported by Okada et al[3] for Boc-Met-pNA and Boc-Lys(Z)-pNA, by Shiori et al[8] for Boc-Leu-pNA, Boc-Lys(Z)-pNA and Boc-Arg(Mts)-pNA and by Noda et al[16]. Both Bajusz[17] and Oyamada et al[28] use the phospho-azo method for the synthesis of Boc-Arg-pNA.HCl. Oyamada et al. reinvestigated the phospho-azo method and synthesized p-nitroanilides of Z- and Boc-amino acids. They achieved yields in the range between 43–94%. The recent results of Noda et al[16] and Oyamada et al[28] prompted us to publish our results obtained using phosphorus oxychloride as the condensing agent[19]. We found that phosphorus oxychloride is a versatile condensing agent for the synthesis of protected amino acid p-nitroanilides. p-Nitroanilides in which the α-amino function is protected by a base-labile protective group[20] is described. Introduction of a base-labile protective function gives access to orthogonally protected p-nitroanilides which can be used as synthons in the synthesis of chromogenic substrates. The use of phosphorus oxychloride in peptide synthesis was for the first time described by Wieland et al[31]. This method was applied and was found to be an excellent and even general way to synthesize p-nitroanilides of protected amino acids. The method implies activation of a protected amino acid with phosphorus oxychloride in pyridine at −15° C. The reaction proved to be complete within 15–30 min.

The syntheses started with Z-amino acids since the acid stability of the Z-group precludes the occurrence of side reactions in the phosphorus oxychloride/pyridine reaction mixture. The use of pyridine as solvent enables the synthesis of p-nitroanilides at low temperature and can also be performed when acid-labile protective groups are used, since the solvent acts as a weak base. To arrive at orthogonality, Boc-protected amino acids require benzyl-derived protections in their side chains. Deprotection of the latter evidently cannot be performed by hydrogenolysis, which would convert p-nitroanilides into p-aminoanilides and thus removal of benzyl functions requires rather severe conditions (HBr/AcOH) which are usually unfavorable. When the α-amino function is protected by a base-labile group, the side chain can be protected by groups which are removable under mildly acidic conditions. This however, requires good stability of the p-nitroanilide bond in media, which attack the base-labile protection. The acid stability of the p-nitroanilide bond is well documented in the literature[2a, 32, 33, 7].

The base stability of the p-nitroanilide bond in Boc-Ala-pNA was found to be stable in 10, 25 and 50% piperidine in DMF and 25% pyrrolidine in DMF. Since the Fmoc-group is removed within 10 min in 25% piperidine in DMF, the p-nitroanilide bond cannot be expected to undergo damage. Activation of Boc-Arg-OH.HCl by phosphorus oxychloride in pyridine in the presence of p-nitroaniline worked very well even at large scale. The experiments were carried out in 300 ml dry pyridine in a 500 ml flask, mechanically stirred and cooled on dry ice/acetone (−80° C.) so that the temperature lies between −20° C./−15° C. during the addition of phosphorus oxychloride.

REFERENCES 2. (a) Erlanger, B. F. et al. (1961) Arch. Biochem. Biophys. 95, 271–278; (b) Tuppy, H. et al. (1962) Hoppe Seylers Z. Physiol. Chem. 329, 278–290; (c) Femfert, U et al (1969) FEBS letters 4, 262–264; (d) Fujiwara, K. et al. (1978), J. Biochem. 83, 1145–1149; (e) Wenzel, H. R. et al. (1980) Hoppe Seylers Z. Physiol. Chem. 361, 1413–1416; (f) Sharma, S. K. et al. (1990) thromb. Res. 57, 127–138.

3. Okada, Y. et al. (1982) Chem. Pharm. Bull. 30, 4060–4066

4. (a) Orlowski, M. and Meister, A. (1963) Biochim. Biophys. Acta 73, 679–681; (b) lit 16

5. (a) lit 2a; (b) Nagel, W. et al. (1965) Hoppe Seylers Z. Physiol. Chem. 340, 1–10; (c) Dagiene, M. (1975) Metody Biokhim. S'ezdu Biokhim. Kit. SSR 2nd, 67–72, Chem. Abstr. (1977) 87, 6317b; (d) Zimmerman, M. and Ashe B. M. 91977) Biochim. Biophys. Acta 480, 241–245; (e) Teno et al. 91991) Chem. Pharm. Bull. 39, 2340–2346.

6. (a) Haverback B. J. et al. (1960) Am. J. Med. 29, 424–433; (b) Bundy, H. F. (1962) Anal. Biochem. 3, 431–435; (c) Bundy, H. F. 91963) Arch Biochem. Biophys. 102, 416–422.

7. (a) Nishi, N. et al. (1970) Bull. Chem. Soc. Jpn. 43, 2900–2907; (b) Nishi, N. et al. (1973) Bull. Chem. Soc. Jpn. 46, 572–576.

8. Shiori, T. et al. (1987) Chem. Pharm. Bull. 35, 2698–2704

9. Burdick, D. J. et al. (1993), Tetrahedron Lett. 34, 2589–2592

10. Reiter, L. A. (1994) Int. J. Peptide Protein Res. 43, 87–96

16. Noda K. et al. (1990) Int. J. Peptide Protein Res. 36, 197–200

17. Bajusz S. et al. (1988) Hung. Teljes HU 40615; Chem Abstr. (1988) 108, 112956w 28. Oyamada, H. et al. (1991) Bull Chem. Soc. Jpn 64, 1422–1424

29. (a) Rijkers, D. T. S. et al (1991) Becl. Trav. Chim. Pays-Bas 110, 347–348; (b) Rijkers, D. T. S. et al (1993) In: Peptides 1992, Proceedings of the 22nd European Peptide Symposium, Schneider, C. H. and Eberle, A. N. (Eds.) 175–176, ESCOM Science Publishers B.V. Leiden, the Netherlands 30. Another synthesis of Fmoc-protected amino acid p-nitroanilides was recently described by Nedev et al. who used isobutyl chloroformate as condensing agent; Nedev, H., Naharisoa, H. and Haertlé, /t. (1993) Tetrahedron Lett. 34, 4201–4204.

31. Wieland, Th et al. (1956) Liebigs Ann. Chem. 599, 70–80

32. Somorin, O et al. (1978) Bull. Chem. Soc. Jpn 51, 1255–1256

33. Shiori, t., et al. (1987) Chem. Pharm. Bull. 35, 2698–2704

Syntheses

Boc-Val-Arg-pNA.HCl

Boc-Val-ONSu (3.40 g, 10.0 mmol) was allowed to react with 2HCl.H-Arg-pNA (3.67 g 10.0 mmol, 1.0 eq.) in the presence of 1.05 eq DIPEA (1.36 g, 1.83 mL, 10.5 mmol) in DMF (75 mL) at room temperature for 16 hrs. After this period of stirring, DMF was evaporated in vacuo and the residue was diluted with BuOH (100 mL). The organic solution was washed with $H_2O$, saturated $NaHCO_3$, $H_2O$ and saturated NaCl (four times 30 mL each). The obtained organic solution was directly evaporated in vacuo. The residue was purified by counter current distribution with the solvent system BuOH/AcOH/$H_2O$ 4:1:5 v/v/v. The product fractions were collected, evaporated in vacuo and lyophilized from AcOH. Yield: 4.71 g (89%), $R_f$(BuOH/AcOH/$H_2O$ 4:1:1 v/v/v): 0.69 (K=2.11), $[\alpha]_D$=−44.4° C.=0.59 MeOH, $^1$NMR ($CD_3OD$): δ_=0.94–0.98 (dd, 6H, γ-$CH_3$/γ'-$CH_3$-Val, J=6.91 Hz); 1.44 (s, 9H, Boc); 1.70 (m, 1H, β-CH-Val (J=6.82 Hz)); 1.82 (m, 2H, γ-$CH_2$-Arg); 2.03 (m, 2H, β-$CH_2$-Arg); 3.23 (m, 2H, δ-$CH_2$-Arg); 3.88 (d, 1H, α-CH-Val (J=6.86 Hz)); 4.56 (m, 1H, α-CH-Arg); 7.84/7.86–8.20/8.22 (dd, 4H, arom pNA).

2HCl.H-Val-Arg-pNA (1)

Boc-Val-Arg-pNA.HCl (2.50 g, 4.72 mmol) was dissolved in AcOH (10 mL) and 2.3 M HCl in EtOAc (10 mL). The reaction mixture was stirred for 2.5 hrs at room temperature. The excess of hydrochloric acid was quenched with tert.-BuOH (50 mL) and the solution was evaporated in vacuo, and coevaporated with tert.-BuOH (twice 20 mL) and MeOH (three times 20 mL). The residue was dissolved in $H_2O$ (50 mL) and washed with $CH_2Cl_2$ (twice 10 mL) and EtOAc (once 10 mL). The resulting aqueous phase was lyophilized. Yield: 1.89 g (86%), $R_f$(BuOH/AcOH/$H_2O$ 4:1:1 v/v/v): 0.40, $[\alpha]_D$=−5.7° C.=0.21 MeOH, $^1$H NMR ($CD_3OD$): δ=1.05/1.07–1.08/1.10 (dd, 6H, γ-$CH_3$/γ'-$CH_3$-Val); 1.70–1.89 (m, 3H, γ-$CH_2$-Arg/β-CH-Val); 1.96–2.25 (dm, 2H, β-$CH_2$-Arg); 3.26 (m, 2H, δ-$CH_2$-Arg); 3.82 (d, 1H, α-CH-Val); 4.58 (m, 1H, α-CH-Arg); 7.85/7.87–8.20/8.22 (dd, 4H, arom pNA).

Boc-Val-Lys(Boc)-pNA

Boc-Val-OH (0.217 g, 1.0 mmol), H-Lys(Boc)-pNA (0.367 g, 1.0 mmol) and HOBt (0.168 g, 1.10 mmol, 1.10 eq.) were dissolved in EtOAc (10 mL) and cooled on ice. DCC (0.219 g, 1.06 mmol, 1.06 eq.) was added and the reaction mixture was stirred for one hour at 0° C. and then for 16 hrs at room temperature. DCU was filtered off and the organic layer was subsequently washed with $H_2O$, 2N $KHSO_4$, $H_2O$, saturated $NaHCO_3$ and saturated NaCl (three times each). The EtOAc layer was dried on $Na_2SO_4$, filtered and evaporated in vocuo. The resulting foam was purified by column chromatography on silica gel, eluens: $CH_2Cl_2$/MeOH 98:2 v/v. Yield: 0.441 g (78%), $R_f$($CH_2Cl_2$/MeOH 95:5 v/v): 0.35, $[\alpha]_D$=−42.4° C.=0.67 MeOH, $^1$H NMR ($CDCl_3$): δ=0.96/1.02 (dd, 6H, γ-$CH_3$/γ'-$CH_3$-Val); 1.44 (s, 18H, Boc (2×9H)); 1.52 (m, 4H, γ-$CH_2$/δ-$CH_2$-Lys); 1.76 (m, 1H, β-CH-Val); 2.04/2.22 (dm, 2H, β-$CH_2$-Lys); 3.15 (m, 2H, ϵ-$CH_2$-Lys); 4.04 (m, 1H, α-CH-Val); 4.52 (m, 1H, α-CH-Lys); 7.84/8.17 (dd, 4H, arom pNA).

2HCl.H-Val-Lys-pNA (1a)

Boc-Val-Lys(Boc)-pNA (0.400 g, 0.71 mmol) was dissolved in AcOH (10 mL) and 3.5 M HCl in EtOAc (10 mL) was added. After stirring for 4 hrs at room temperature, the acid was quenched by the addition of tert.-BuOH (20 mL) and the mixture was evaporated in vacuo. The residue was coevaporated with tert.-BuOH (once 10 mL) and MeOH (twice 10 mL). The crude deprotected product was purified by counter current distribution with BuOH/AcOH/$H_2O$ 4:1:5 v/v/v as the solvent system. Fractions containing the pure product were collected and evaporated in vacuo. The residue was dissolved in $H_2O$ and lyophilized. Yield: 0.233 g (75%), $R_f$(BuOH/AcOH/$H_2O$ 4:1:1 v/v/v): 0.34 (K=0.34), $[\alpha]_D$=−10.7° C.=0.36 MeOH, $^1$H NMR ($D_2O$): δ=0.87 (dd, 6H, γ-$CH_3$/γ'-$CH_3$-Val); 1.37 (m, 2H, γ-$CH_2$-Lys); 1.57 (m, 2H, δ-$CH_2$-Lys); 1.77 (m, 2H, β-CH-Val/β-$CH_2$-Lys(1H)); 2.11 (m, 1H, β-$CH_2$-Lys(1H)); 2.86 (m, 2H, ϵ-$CH_2$-Lys); 3.75 (d, 1H, α-CH-Val); 4.35 (m, 1H, α-CH-Lys); 7.51/8.04 (dd, 4H, arom pNA).

MZ-Val-Arg-pNA.HCl (2)

2HCl.H-Val-Arg-pNA (0.1716 g, 0.368 mmol) was dissolved in DMF (2 mL) which contained DIPEA (126 μL, 0.723 mmol, 2.0 eq.). To this solution was added MZ-ONSu (0.76 mL of a 0.5 M solution in $CH_3CN$, 0.38 mmol, 1.03 eq.) and the reaction mixture was stirred for two days at room temperature. DMF was evaporated in vacuo and the oily residue was purified by counter current distribution using the solvent combination BuOH/AcOH/$H_2O$ 4:1:5 v/v/v. The pure product fractions were collected, evaporated in vacuo, dissolved in $H_2O$ and lyophilized. Yield: 80 mg (41%), $R_f$(BuOH/AcOH/$H_2O$ 4:1:1 v/v/v): 0.57 (K=1.99), $[\alpha]_D$=−27.6° C.=0.21 MeOH, $^1$H NMR ($D_2O$): δ=0.79 (dd, 6H, γ-$CH_3$/γ'-$CH_3$-Val); 1.54 (m, 2H, γ-$CH_2$-Arg); 1.70 (m, 1H, β-CH-Val); 1.80/1.94 (dm, 2H, β-$CH_2$-Arg); 3.06 (m, 2H, δ-$CH_2$-Arg); 3.34 (s, 2H, $CH_2$-malonic acid); 3.57 (s, 3H. $OCH_3$); 3.99 (d, 1H, α-CH-Val); 4.34 (m, 1H, α-CH-Arg); 7.52/8.07 (dd, 4H, arom pNA).

Msc-Val-OH

This compound was synthesized according to the method of Tesser and Balvert-Geers[18]. H-Val-OH (5.7 g, 48.7 mmol, 1.09 eq.) was suspended into $CH_3CN/H_2O$ 4:1 v/v (50 mL). Msc-ONp (11.8 g, 44.5 mmol) was added followed by TEA (6.2 mL, 44.5 mmol, 1.0 eq.). The obtained turbid reaction mixture was stirred for 3 hrs at room temperature. After this period of stirring, the reaction mixture was filtered and evaporated in vacuo to remove the co-solvent $CH_3CN$. The aqueous phase was turbid and was acidified to pH=3 with 3N HCl. The clear solution was stored at 0° C. for several days. The crystals were filtered off, washed with ice-cold $H_2O$ and dried over $P_2O_5$. Yield: 3.60 g (30%, first crop; 2.5 g (21%, second crop), total: 6.10 g (51%), lit: 66%), $R_f$(BuOH/AcOH/$H_2O$ 4:1:1 v/v/v): 0.65, $[\alpha]_D$=−0.95° C.=1.16 AcOH, mp: 128° C. (lit: $[\alpha]_D$=−2.2° C.=1 AcOH, mp: 128° C.), $^1$H NMR ($D_2O$): δ=0.67/0.71–0.73/0.78 (dd, 6H, γ-$CH_3$/γ'-CH-Val); 1.94 (m, 1H, β-$CH_3$-Val); 2.93 (s, 3H, $CH_3$—$SO_2$~ Msc); 3.39 (t, 2H, ~$SO_2$—$CH_2$~ Msc); 3.82 (d, 1H, α-CH-Val); 4.26 (t, 2H, ~$CH_2$—O—$CO^{18}$ Msc).

Msc-Val-ONSu

Msc-Val-OH (1.08 g, 4.04 mmol) and HONSu (0.47 g, 4.09 mmol, 1.01 eq.) were dissolved in $CH_3CN$ (40 mL). The solution was cooled on ice, DCC (0.88 g, 4.27 mmol, 1.06 eq.) was added and the reaction mixture was stirred for 16 hrs at room temperature. DCU was filtered off and the $CH_3CN$ phase was evaporated to dryness. The residue was recrystallized from iso-propyl alcohol. Yield: 1.10 g (75%), $[\alpha]_D$=−31.8° C.=1 dioxane, mp: 129° C., $^1$H NMR ($CDCl_3$): δ=1.03/1.06–1.09/1.13 (dd, 6H, γ-$CH_3$/γ'-$CH_3$-Val); 2.31 (m, 1H, β-CH-Val); 2.86 (s, 4H, $CH_2$-ONSu (2×2H)); 2.97 (s, 3H, $CH_3$—$SO_2$~ Msc); 3.37 (t, 2H, ~$SO_2$—$CH_2$~ Msc); 4.53–4.63 (m, 3H, α-CH-Val/~$CH_2$—O—CO~ Msc); 5.35 (bd, 1H, NH).

Msc-Val-ONp

Msc-Val-OH (2.0 g, 7.49 mmol) and p-nitrophenol (1.3 g, 9.75 mmol, 1.25 eq.) were dissolved in $CH_3CN$ (50 mL).

The solution was cooled on ice and DCC (1.62 g, 7.86 mmol, 1.05 eq.) was added. After stirring of 16 hrs at room temperature, DCU was filtered off and the solution was evaporated in vacuo. The residual oil was solidified in diethyl ether and recrystallized from iso-propyl alcohol. Yield: 2.0 g (69%), $[\alpha]_D$=−39.9° C.=1 dioxane, mp: 114° C., $^1$H NMR ($CDCl_3$): δ=1.06 (dd, 6H, γ-$CH_3$/γ'-$CH_3$-Val); 2.40 (m, 1H, β-CH-Val); 2.99 (s, 3H, $CH_3$—$SO_2$~ Msc); 3.37 (t, 2H, ~$SO_2$—$CH_2$~ Msc); 4.56 (m, 3H, α-CH-Val/~$CH_2$—O—CO~ Msc); 5.31 (d, 1H, NH); 7.26/7.34–8.25/8.36 (dd, 4H, arom ONp).

Msc-Val-Arg-pNA. HCl (2a)

Msc-Val-ONp (116 mg, 0.30 mmol), 2HCl.H-Arg-pNA (120 mg, 0.33 mmol, 1.10 eq.) were dissolved in DMF (3 mL) and TEA (51 μL, 0.37 mmol, 1.23 eq.) was added. The suspension was stirred for 16 hrs at room temperature, and DMF was removed under reduced pressure. The oily residue was dissolved in $H_2O$ (20 mL) and washed with diethyl ether (three times 5 mL). The aqueous phase was lyophilized. The product was purified by counter current distribution with the solvent system BuOH/AcOH/$H_2O$ 4:1:5 v/v/v. The pure product fractions were collected, evaporated in vacuo, dissolved in $H_2O$ and lyophilized. Yield: 147 mg, (85%), $R_f$(BuOH/AcOH/$H_2O$ 4:1:1 v/v/v): 0.48 (K=1.50), $[\alpha]_D$=−37.6° C.=0.29 MeOH, $^1$H NMR ($D_2O$): δ=0.76 (dd, 6H, γ-$CH_3$/γ'-$CH_3$-Val); 1.50 (m, 2H, γ-$CH_2$-Arg); 1.62–1.94 (bm, 3H, β-CH-Val/β-$CH_2$-Arg); 2.94 (s, 3H, $CH_3$—$SO_2$~ Msc); 3.05 (t, 2H, δ-$CH_2$-Arg); 3.41 (t, 2H, ~$SO_2$—$CH_2$~ Msc); 3.75 (d, 1H, α-CH-Val); 4.33 (m, 3H, α-CH-Arg/~$CH_2$—O—CO~ Msc); 7.49/8.04 (dd, 4H, arom pNA).

Msc-Val-X-pNA a) X=Lys(Boc)

Msc-Val-ONSu (109 mg, 0.30 mmol), H-Lys(Boc)-pNA (122 mg, 0.33 mmol, 1.10 eq.) were dissolved in DMF (3 mL) and TEA ( 51 μL, 0.37 mmol, 1.23 eq.) was added. After stirring overnight at room temperature the reaction mixture was evaporated in vacuo. The residue was dissolved in EtOAc and subsequently washed with $H_2O$, saturated $NaHCO_3$, 2N $KHSO_4$ and saturated NaCl. The EtOAc layer was dried on $Na_2SO_4$, filtered and evaporated to dryness. The resulting foam was purified by column chromatography on silica gel with $CH_2Cl_2$/MeOH 95:5 v/v as eluent. Yield: 145 mg (79%), $R_f$($CH_2Cl_2$/MeOH 95:5 v/v): 0.22, $R_f$(BuOH/AcOH/$H_2O$ 4:1:1 v/v/v): 0.87, $[\alpha]_D$=−32.8° C.=0.56 MeOH, $^1$H NMR ($CDCl_3$): δ=0.97 (dd, 6H, γ-$CH_3$/γ'-$CH_3$-Val); 1.43 (m, 13H, Boc(9H)/γ-$CH_2$/δ-$CH_2$-Lys); 1.74 (m, 3H, β-CH-Val/β-$CH_2$-Lys); 2.92 (m, 5H, $CH_3$—$SO_2$~ Msc/ε-$CH_2$-Lys); 3.11 (t, 2H, ~$SO_2$—$CH_2$~ Msc); 4.05 (m, 1H, α-CH-Val); 4.60 (m, 3H, α-CH-Lys/~$CH_2$—O—CO~ Msc); 5.54 (d, 1H, NH); 7.10 (d, 1H, NH); 7.76/7.88–8.13/8.22 (dd, 4H, arom pNA); 9.21 (s, 1H, arom NH).

b) X=Orn(Boc)

Obtained as described for a)

Quantities used: Msc-Val-ONSu: 76 mg (0.21 mmol), HCl.H-Orn(Boc)-pNA: 81 mg (0.21 mmol), TEA: 62 μL (0.45 mmol, 2.14 eq.). Yield: 60 mg (47%), $R_f$($CH_2Cl_2$/MeOH 95:5 v/v): 0.22, $R_f$(BuOH/AcOH/$H_2O$ 4:1:1 v/v/v): 0.84, $[\alpha]_D$=−43.6° C.=1 MeOH.

c) X=Nle (2d)

Obtained as described for a)

Quantities used: Msc-Val-ONSu: 181 mg (0.50 mmol), HCl.H-Nle-pNA: 142 mg (0.50 mmol), TEA: 146 μL (1.06 mmol, 2.12 eq.). This product was purified by counter current distribution with BuOH/AcOH/$H_2O$ 4:1:5 v/v/v (K=10.52) as the solvent combination. After work-up the pure product was lyophilized from AcOH. Yield: 144 mg (58%), $R_f$($CH_2Cl_2$/MeOH 95:5 v/v): 0.37, $R_f$(BuOH/AcOH/$H_2O$ 4:1:1 v/v/v): 0.87, $[\alpha]_D$=−51.4° C.=0.25 MeOH, $^1$H NMR ($CD_3OD$): δ=0.95 (t, 3H, ε-$CH_3$-Nle); 0.99 (dd, 6H, γ-$CH_3$/γ'-$CH_3$-Val); 1.39 (bm, 4H, γ-$CH_2$/δ-$CH_2$-Nle); 1.78/1.89 (dm, 2H, β-$CH_2$-Nle); 2.10 (m, 1H, β-CH-Val); 3.05 (s, 3H, $CH_3$—$SO_2$~ Msc); 3.48 (t, 2H, ~$SO_2$—$CH_2$~ Msc); 3.97 (d, 1H, α-CH-Val); 4.48 (m, 1H, α-CH-Nle); 4.56 (m, 2H, ~$CH_2$—O—CO~ Msc); 7.86/8.22 (dd, 4H, arom pNA).

Msc-Val-X-pNA.HCl

The Boc-protected dipeptides were dissolved in AcOH (2 mL) and 3.5 M HCl in EtOAc (2 mL) was added. After 2 hrs of stirring, the acid was quenched with tert.-BuOH (10 mL) and the reaction mixture was evaporated in vacuo. The residue was coevaporated with tert.-BuOH (once 5 mL) and MeOH (twice 10 mL). The residue was dissolved in $H_2O$ (15 mL) and subsequently washed with $CH_2Cl_2$ (twice 10 mL) and diethyl ether (once 10 mL). The aqueous phase was lyophilized.

a) X=Lys (2b)

Yield: 95 mg (73%), $R_f$(BuOH/AcOH/$H_2O$ 4:1:1 v/v/v): 0.49, $[\alpha]_D$=−52.6° C.=0.23 MeOH, $^1$H NMR ($D_2O$): δ=0.81 (dd, 6H, γ-$CH_3$/γ'-$CH_3$-Val); 1.36 (m, 2H, δ-$CH_2$-Lys); 1.58 (m, 2H, γ-$CH_2$-Lys); 1.76/1.92 (dm, 3H, β-CH-Val/β-$CH_2$-Lys); 2.86 (t, 2H, ε-$CH_2$-Lys); 2.99 (s, 3H, $CH_3$—$SO_2$~ Msc); 3.45 (t, 2H, ~$SO_2$—$CH_2$~ Msc); 3.79 (d, 1H, α-CH-Val); 4.23 (m, 1H, α-CH-Lys); 4.37 (t, 2H, ~$CH_2$—O—CO~ Msc); 7.51/8.04 (dd, 4H, arom pNA).

b) X=Orn (2c)

Yield: 47 mg (88%), $R_f$(BuOH/AcOH/$H_2O$ 4:1:1 v/v/v): 0.45, $[\alpha]_D$=−49.3 c=0.14 MeOH, $^1$H NMR ($D_2O$): δ=0.82 (dd, 6H, γ-$CH_3$/γ'-$CH_3$-Val); 1.57–1.84 (bm, 3H γ-$CH_2$-Orn/β-CH-Val); 1.84–1.95 (m, 2H, β-$CH_2$-Orn); 2.92 (t, 2H, δ-$CH_2$-Orn); 2.99 (s, 3H, $CH_3$—$SO_2$~ Msc); 3.46 (t, 2H, ~$SO_2$—$CH_2$~ Msc); 3.81 (d, 1H, α-CH-Val); 4.39 (m, 3H, α-CH-Orn/~$CH_2$—O—CO~Msc); 7.53/8.08 (dd, 4H, arom pNA).

Boc-Gly-Val-$N_2H_3$

Boc-Gly-OH (1.80 g, 10.3 mmol), HCl.H-Val-OMe (1.70 g, 10.1 mmol), HOBt (1.70 g, 11.1 mmol, 1.10 eq.) were suspended in EtOAc (50 mL). This mixture was cooled on ice and the amino component was set free with DIPEA (1.85 mL, 10.6 mmol, 1.05 eq.). Then DCC (2.16 g, 10.5 mmol, 1.04 eq.) was added and the suspension was stirred for one hour at 0° C. and for 16 hrs at room temperature. After this period DCU was filtered off and the clear organic solution was subsequently washed with 2N $KHSO_4$, $H_2O$, saturated $NaHCO_3$ and saturated NaCl (three times 30 mL each). The EtOAc layer was dried on $Na_2SO_4$, filtered and evaporated in vacuo, yielding an oil which still contained residual DCU; it was therefore dissolved in diethyl ether and filtered, and appeared then to be free of DCU ($R_f$($CH_2Cl_2$/MeOH 9:1 v/v): 0.60, single spot). The ester was used as such in the hydrazinolysis. The obtained oil was dissolved in MeOH (20 mL) and $N_2H_4$.$H_2O$ (2.5 mL, 51.5 mmol, 5.1 eq.) was added. This reaction mixture was stirred for three days at room temperature. After this period the reaction mixture was evaporated in vacuo and the residue was coevaporated with MeOH (three times 20 mL). The residue was recrystallized from diiso-propyl ether. Yield: 2.16 g (75%), $R_f$($CH_2Cl_2$/MeOH 9:1 v/v): 0.37, mp: 118–121° C., $[\alpha]_D$=27.0 c=0.70 MeOH, $^1$H NMR ($CDCl_3$): δ=0.91/0.96 (dd, 6H, γ-$CH_3$/γ'-$CH_3$-Val); 1.45 (s, 9H, Boc); 2.11 (m, 1H, β-CH-Val); 3.64 (dd, 2H, $CH_2$-Gly); 3.66 (m, 1H, NH); 4.29 (dd, 1H, α-CH-Val); 5.73 (m, 1H, NH); 7.17 (d, <2H, $NH_2$); 8.46 (s, 1H, NH).

Boc-Gly-Val-Arg-pNA.HCl (3')

Boc-Gly-Val-$N_2H_3$ (1.23 g, 4.26 mmol) was dissolved in DMF (40 mL). This solution was cooled on dry ice/aceton to −20° C. To this solution were added: 2.3 M HCl in EtOAc (5.2 mL, 12.0 mmol, 2.81 eq.) and tert.-BuONO (0.60 mL, 5.04 mmol, 1.18 eq.). This reaction mixture was stirred for 15 min at −20° C. (no Barton positive material is present: azide formation is complete). The reaction mixture was neutralized by adding DIPEA (2.05 mL, 11.7 mmol) and 2HCl.H-Arg-pNA (1.56 g, 4.26 mmol, 1.0 eq.) followed by DIPEA (0.75 mL, 4.31 mmol, 1.01 eq.) were added. The reaction mixture was kept at 0° C. for 16 hrs; at regular time intervals the pH was checked and when necessary DIPEA was added to maintain the pH at 7 to 8. When the reaction was complete, the solvent was evaporated in vacuo and the residue was diluted with BuOH. The solution was washed with $H_2O$, saturated $NaHCO_3$, $H_2O$ and saturated NaCl respectively. After removal of the solvent the residue was purified by counter current distribution with BuOH/AcOH/$H_2O$ 4:1:5 v/v/v as solvent system. The pure fractions were collected and evaporated in vocuo. The residue was dissolved in AcOH and lyophilized. Yield: 2.22 g (89%), $R_f$(BuOH/AcOH/$H_2O$ 4:1:1 v/v/v): 0.66 (K=2.96), $[\alpha]_D$=−28.7° C.=0.57 MeOH, $^1$H NMR ($CD_3OD$): δ=0.99 (dd, 6H, γ-$CH_3$/γ'-$CH_3$-Val); 1.40 (s, 9H, Boc); 1.65–1.88 (dm, 3H, γ-$CH_2$-Arg/β-CH-Val); 1.93/2.15 (dm, 2H, β-$CH_2$-Arg); 3.23 (m, 2H, δ-$CH_2$-Arg); 3.71/3.84 (dd, 2H, $CH_2$-Gly); 4.18 (d, 1H, α-CH-Val); 4.54 (m, 1H, α-CH-Arg); 7.91/7.93–8.19/8.22 (dd, 4H, arom pNA).

2HCl.H-Gly-Val-Arg-pNA (3)

Boc-Gly-Val-Arg-pNA.HCl (1.2037 g, 2.052 mmol) was dissolved in AcOH (10 mL) and 2.3 M HCl in EtOAc (10 mL) was added. The reaction mixture was stirred for three hrs, the acid was quenched with tert.-BuOH (20 mL) and evaporated in vacuo. The residue was coevaporated with tert.-BuOH and with MeOH (once 20 mL each). The residue was purified by counter current distribution with BuOH/AcOH/$H_2O$ 4:1:5 v/v/v as solvent combination. The pure product was dissolved in $H_2O$ and lyophilized. Yield: 0.94 g (88%), $R_f$(BuOH/AcOH/$H_2O$ 4:1:1 v/v/v): 0.32 (K=0.37), $[\alpha]_D$=−42.7° C.=0.26 MeOH, $^1$H NMR ($CD_3OD$): δ=0.98–1.03 (dd, 6H, γ-$CH_3$/γ'-$CH_3$-Val (J=6.8 Hz)); 1.61–2.05 (m, 4H, β-$CH_2$-Arg(1H)/β-CH-Val/γ-$CH_2$-Arg); 2.17 (dm, 1H, β-$CH_2$-Arg(1H)); 3.26 (m, 2H, δ-$CH_2$-Arg); 3.76–3.87 (dd, 2H, $CH_2$-Gly); 4.28 (d, 1H, α-CH-Val (J=6.4 Hz)); 4.53 (m, 1H, α-CH-Arg); 7.88/7.90–8.20/8.23 (dd, 4H, arom pNA).

Boc-Gly-Val-X-pNA a) X=Lys(Boc)

Boc-Gly-Val-$N_2H_3$ (0.288 g, 1.0 mmol) was dissolved in DMF (10 mL) and cooled to −20° C. Subsequently 3.5 M HCl in EtOAc (0.80 mL, 2.75 mmol, 2.75 eq.) and tert.-BuONO (0.14 mL, 1.20 mmol, 1.2 eq.) were added. After 15 min the conversion to the corresponding azide was complete (negative Barton test) and the reaction mixture was neutralized by adding DIPEA (0.473 mL, 2.75 mmol, 2.75 eq.). H-Lys(Boc)-pNA (0.366 g, 1.0 mmol, 1.0 eq.) was added to the azide solution. The reaction mixture was kept for 16 hrs at 0° C. Then the solvent was removed under reduced pressure and the residue was diluted with EtOAc (30 mL). The organic solution was subsequently washed with $H_2O$, 2N KHSO, $H_2O$, saturated $NaHCO_3$, $H_2O$ and saturated NaCl (three times 10 mL each). After drying on $Na_2SO_4$, evaporation in vacuo resulted in a foam which was purified by column chromatography on slica gel with $CH_2Cl_2$/MeOH 95:5 v/v as eluens. Yield: 0.51 g (81%), $R_f$($CH_2Cl_2$/MeOH 95:5 v/v): 0.17, $R_f$($CH_2Cl_2$/MeOH 9:1 v/v): 0.60, $[\alpha]_D$=−27.8° C.=0.39 MeOH, $^1$H NMR ($CD_3OD$): δ=0.97/0.99–1.00/1.02 (dd, 6H, γ-$CH_3$/γ'-$CH_3$-Val); 1.39 (s, 9H, Boc); 1.41 (s, 9H, Boc); 1.48 (m, 4H, γ-$CH_2$/δ-$CH_2$-Lys); 1.80 (m, 1H, β-CH-Val); 1.93/2.13 (dm, 2H, β-$CH_2$-Lys); 3.04 (m, 2H, ε-$CH_2$-Lys); 3.74 (dd, 2H, $CH_2$-Gly); 4.21 (d, 1H, α-CH-Val); 4.44 (m, 1H, α-CH-Lys); 7.91/7.93–8.19/8.21 (dd, 4H, arom pNA).

b) X=Orn(Boc)

Obtained as described for a)

Quantities used: HCl.H-Orn(Boc)-pNA: 0.389 g (0.776 mmol), DIPEA: 0.20 mL (1.16 mmol, 1.50 eq.). Yield: 0.31 g (66%), $R_f$($CH_2Cl_2$/MeOH 95:5 v/v): 0.17, $R_f$($CH_2Cl_2$/MeOH 9:1 v/v): 0.57, $[\alpha]_D$=−29.2° C.=0.27 MeOH, $^1$H NMR ($CD_3OD$): δ=0.97/0.99–0.99/1.01 (dd, 6H, γ-$CH_3$/γ'-$CH_3$-Val); 1.40 (s, 9H, Boc); 1.42 (s, 9H, Boc); 1.55 (m, 2H, γ-$CH_2$-Orn); 1.77 (m, 1H, β-CH-Val); 1.89/2.13 (dm, 2H, β-$CH_2$-Orn); 3.08 (m, 2H, δ-$CH_2$-Orn); 3.74 (dd, 2H, $CH_2$-Gly); 4.21 (d, 1H, α-CH-Val); 4.47 (m, 1H, α-CH-Orn); 7.90/7.92–8.19/8.22 (dd, 4H, arom pNA).

c) X=Nle

Obtained as described for a)

Quantities used: HCl.H-Nle-pNA: 0.288 g (1.00 mmol), DIPEA: 0.20 mL (1.16 mmol, 1.16 eq.). Yield: 0.40 g (79%), $R_f$($CH_2Cl_2$/MeOH 95:5 v/v): 0.21, $R_f$($CH_2Cl_2$/MeOH 9:1 v/v): 0.63, $[\alpha]_D$=−38.0° C.=0.36 MeOH, $^1$H NMR ($CD_3OD$): δ=0.93 (m, 3H, ε-$CH_3$-Nle); 0.97/0.99–1.00/1.01 (dd, 6H, γ-$CH_3$/γ'-$CH_3$-Val); 1.38 (s, 9H, Boc); 1.45 (m, 4H, γ-$CH_2$/δ-$CH_2$-Nle); 1.79 (m, 1H, β-CH-Val); 1.93/2.14 (dm, 2H, β-$CH_2$-Nle); 3.73 (dd, 2H, $CH_2$-Gly); 4.21 (d, 1H, α-CH-Val); 4.43 (m, 1H, α-CH-Nle); 7.93/7.95–8.19/8.21 (dd, 4H, arom pNA).

nHCl.H-Gly-Val-X-pNA a) X=Lys, n=2 (3a)

Boc-Gly-Val-Lys(Boc)-pNA was dissolved in AcOH (5 mL) and 3.5 M HCl in EtOAc (5 mL) was added. After 2 hrs of stirring at room temperature the acid was quenched with tert.-BuOH (10 mL) and evaporated in vacuo. The obtained residue was coevaporated with tert.-BuOH (twice 10 mL) and MeOH (10 mL), dissolved in $H_2O$ and lyophilized. After purification by counter current distribution using the solvent combination BuOH/AcOH/$H_2O$ 4:1:5 v/v/v the pure product was obtained as a fluffy off-white powder. Yield: 0.29 g (72%), $R_f$(BuOH/AcOH/$H_2O$ 4:1:1 v/v/v): 0.33 (K=0.32), $[\alpha]_D$=−56.1° C.=0.36 MeOH, $^1$H NMR ($D_2O$): δ=0.78 (dd, 6H, γ-$CH_3$/γ'-$CH_3$-Val); 1.33 (m, 2H, γ-$CH_2$-Lys); 1.53 (m, 2H, δ-$CH_2$-Lys); 1.74 (m, 2H, β-$CH_2$Lys(1H)/β-CH-Val); 1.92 (m, 1H, β-$CH_2$-Lys(1H)); 2.82 (m, 2H, ε-$CH_2$-Lys); 3.71 (dd, 2H, $CH_2$-Gly); 4.05 (d, 1H, α-CH-Val); 4.28 (m, 1H, α-CH-Lys); 7.49/8.05 (dd, 4H, arom pNA).

b) X=Orn, n=2 (3b)

Obtained as described for a)

Yield: 0.18 g (73%), $R_f$(BuOH/AcOH/$H_2O$ 4:1:1 v/v/v): 0.33 (K=0.29), $[\alpha]_D$=−52.7° C.=0.25 MeOH, $^1$H NMR ($D_2O$): δ=0.77 (dd, 6H, γ-$CH_3$/γ'-$CH_3$-Val); 1.54–1.85 (bm, 4H, β-$CH_2$-Orn(1H)/β-CH-Val/γ-$CH_2$-Orn); 1.94 (m, 1H, β-$CH_2$-Orn(1H)); 2.86 (m, 2H, δ-$CH_2$-Orn); 3.71 (dd, 2H, $CH_2$-Gly); 4.04 (d, 1H, α-CH-Val); 4.23 (m, 1H, α-CH-Orn); 7.52/8.06 (dd, 4H, arom pNA).

c) X=Nle, n=1 (3c)

Obtained as described for a)

Yield: 0.28 g (80%), $R_f$(BuOH/AcOH/$H_2O$ 4:1:1 v/v/v): 0.68 (K=2.40), $[\alpha]_D$=−67.2° C.=0.24 MeOH, $^1$H NMR ($CD_3OD$): δ=0.84 (t, 3H, ε-$CH_3$-Nle); 0.86/0.90 (dd, 6H, γ-$CH_3$/γ'-$CH_3$-Val); 1.29 (m, 4H, γ-$CH_2$/δ-$CH_2$-Nle); 1.66 (m, 1H, β-CH-Val); 1.79/2.02 (dm, 2H, β-$CH_2$-Nle); 3.60 (s, 2H, $CH_2$-Gly); 4.21 (d, 1H, α-CH-Val); 4.35 (m, 1H, α-CH-Nle); 7.75/8.11 (dd, 4H, arom pNA).

Boc-Glu(O$^t$Bu)-OH

H-Glu(O$^t$Bu)-OH ($R_f$(BuOH/AcOH/$H_2O$ 4:1:1 v/v/v): 0.52, $[\alpha]_D$=+9.3° C.=1.05 $H_2O$, mp: 181° C. (dec.); lit[24]:

$[\alpha]_D$=+9.8° C.=2 $H_2O$, mp: 182° C.) (2.0 g, 9.85 mmol), $NaHCO_3$ (1.86 g, 22.2 mmol, 2.25 eq.) were dissolved in $H_2O$ (40 mL) and $Boc_2O$[25] (2.36 g, 10.8 mmol, 1.10 eq.) dissolved in dioxane (20 mL) was added. The reaction mixture became turbid and gas evolution started. After 3 hrs of stirring at room temperature, the reaction mixture was partially evaporated in vacuo. The aqueous solution was acidified with 10% citric acid and the precipitating oil was taken up into EtOAc (three extractions 20 mL). The EtOAc layer was subsequently washed with $H_2O$ (five times 30 mL), saturated NaCl (three times 30 mL) and dried on $Na_2SO_4$. The residue obtained after evaporation in vacuo was an oil which crystallized slowly. Yield: 2.91 g (98%), $R_f$(BuOH/AcOH/$H_2O$ 4:1:1 v/v/v): 0.87, $R_f$($CH_2Cl_2$/MeOH 9:1 v/v): 0.17, $[\alpha]_D$=−10.3° C.=0.93 MeOH, mp: 98–99° C. (lit[26]: $[\alpha]_D$=−10.9° C.=1 MeOH, mp:101–102° C.), $^1H$ NMR ($CDCl_3$): δ=1.44 (s, 18H, Boc/O$^t$Bu (2×9H)); 1.99/2.18 (dm, 2H, β-$CH_2$); 2.38 (m, 2H, γ-$CH_2$); 4.34 (m, 1H, α-CH); 5.23 (d, 1H, NH).

Boc-Glu(O$^t$Bu)-ONSu

Boc-Glu(O$^t$Bu)-ONSu was prepared according to the literature[27]. Quantities used: Boc-Glu(O$^t$Bu)-OH: 2.56 g (8.45 mmol), DCC: 1.83 g (8.88 mmol, 1.05 eq.), HONSu: 1.07 g (9.30 mmol, 1.10 eq.), $CH_3CN$: 30 mL. Yield: 2.98 g (88%), $[\alpha]_D$=−26.6° C.=0.64 dioxane, mp: 134–137° C. (recrystallized from iso-propyl alcohol).

Boc-Glu(O$^t$Bu)-Gly-OH

H-Gly-OH (0.13 g, 1.73 mmol, 1.16 eq.) and $NaHCO_3$ (0.28 g, 3.38 mmol, 2.25 eq.) were dissolved in $H_2O$ (10 mL) and Boc-Glu(O$^t$Bu)-ONSu (0.60 g, 1.50 mmol), dissolved in $CH_3CN$ (15 mL), was added dropwise. The resulting turbid reaction mixture was stirred at room temperature. After a period of 16 hrs of stirring, the organic solvent was removed in vacuo and the aqueous phase was acidified to pH=3 with 2N $KHSO_4$. The precipitated oil was extracted into EtOAc (twice 10 mL) and subsequently washed with 2N $KHSO_4$ and saturated NaCl (once respectively twice 10 mL). The EtOAc layer was dried on $Na_2SO_4$, filtered and evaporated in vacuo. The resulting foam did not crystallize. Yield: 0.51 g (94%), $R_f$($CH_2Cl_2$/MeOH 9:1 v/v): 0.19, $R_f$($CH_2Cl_2$/MeOH 8:2 v/v): 0.22, $R_f$(BuOH/AcOH/$H_2O$ 4:1:1 v/v/v): 0.84, $[\alpha]_D$=−12.6° C.=0.67 MeOH, $^1H$ NMR ($CDCl_3$): δ=1.44 (s, 18H, Boc/O$^t$Bu (2×9H)); 1.91/2.10 (dm, 2H, β-$CH_2$-Glu); 2.36 (m, 2H, γ-$CH_2$-Glu); 4.07 (2×dd, 2H, $CH_2$-Gly); 4.35 (m, 1H, α-CH-Glu); 5.68 (d, 1H, NH-Glu); 7.35 (m, 1H, NH-Gly).

Boc-Gly-Gly-OH, Boc-Gly-Pro-OH and Boe-Pro-Gly-OH

Were obtained as described for Boc-Glu(O$^t$Bu)-Gly-OH. Due to the good water solubility, acidification leads to clear aqueous solutions. The dipeptides were extracted into EtOAc after saturation of the aqueous phase with NaCl. The products were recrystallized from iso-propyl alcohol/diisopropyl ether.

Quantities used: Boc-Gly-Gly-OH: Boc-Gly-ONSu: 1.36 g (5.0 mmol), H-Gly-OH: 0.41 g (5.47 mmol, 1.09 eq.), $NaHCO_3$: 0.95 g (11.31 mmol, 2.26 eq.). Yield: 1.13 g (97%), $R_f$($CH_2Cl_2$/MeOH 8:2 v/v): 0.08, $R_f$(BuOH/AcOH/$H_2O$ 4:1:1 v/v/v): 0.66, mp: 123–124° C. (dec.), $^1H$ NMR (DMSO-$d_6$): δ=1.38 (s, 9H, Boc); 3.57 (d, 2H, $CH_2$-Gly (C-terminal)); 3.76 (d, 2H, $CH_2$-Gly (N-terminal)); 6.98 (t, 1H, NH); 8.04 (t, 1H, NH). Boc-Gly-Pro-OH: Boc-Gly-ONSu: 1.36 g (5.0 mmol), H-Pro-OH: 0.63 g (5.48 mmol, 1.10 eq.), $NaHCO_3$: 0.95 g (11.31 mmol, 2.26 eq.). Yield: 1.36 g (quant.), $R_f$($CH_2Cl_2$/MeOH 8:2 v/v): 0.18, $R_f$(BuOH/AcOH/$H_2O$ 4:1:1 v/v/v): 0.67, $[\alpha]_D$=−70.8° C.=0.98 MeOH, mp: 123° C., $^1H$ NMR ($CDCl_3$): δ=1.44 (s, 9H, Boc); 2.14 (m, 4H, $CH_2$-Pro (2×2H)); 3.54 (m, 2H, N—$CH_2$-Pro); 3.98 (dd, 2H, $CH_2$-Gly); 4.50 (m, 1H, α-CH-Pro); 5.82 (m, <1H, NH); 8.46 (s, 1H, COOH).

Boc-Pro-Gly-OH: Boc-Pro-ONSu: 1.56 g (5.0 mmol), H-Gly-OH: 0.41 g (5.47 mmol, 1.09 eq.), $NaHCO_3$: 0.95 g (11.31 mmol, 2.26 eq.). Yield: 1.36 g (quant.), $R_f$($CH_2Cl_2$/MeOH 8:2 v/v): 0.18, $R_f$(BuOH/AcOH/$H_2O$ 4:1:1 v/v/v): 0.73, $[\alpha]_D$=−66.0° C.=0.78 MeOH, mp: 149–151° C. (dec.), $^1H$ NMR ($CDCl_3$/$CD_3OD$ 1:1 v/v): δ=1.23 (s, 9H, Boc); 1.64–1.96 (bm, 4H, $CH_2$-Pro (2×2H)); 3.25 (m, 2H, N—$CH_2$-Pro); 3.76 (s, 2H, $CH_2$-Gly); 4.04 (m, 1H, α-CH-Pro).

Boc-Glu(O$^t$Bu)-Gly-ONSu, Boc-Gly-Gly-ONSu, Boc-Gly-Pro-ONSu and Boc-Pro-Gly-ONSu The protected dipeptide acids were converted to their ONSu-esters following the literature[27].

Quantities used: Boc-Glu(O$^t$Bu)-Gly-ONSu: Boc-Glu(O$^t$Bu)-Gly-OH: 0.54 g (1.5 mmol), DCC: 0.32 g (1.55 mmol, 1.04 eq.), HONSu: 0.19 g (1.65 mmol, 1.10 eq.), $CH_3CN$: 15 mL. Yield: 0.569 g (83%), $[\alpha]_D$=−19.6° C.=0.70 dioxane, mp: 79–83° C.

Boc-Gly-Gly-ONSu: Boc-Gly-Gly-OH: 1.16 g (5.0 mmol), DCC: 1.08 g (5.24 mmol, 1.05 eq.), HONSu: 0.63 g (5.48 mmol, 1.10 eq.), $CH_3CN$/EtOAc (1:1 v/v): 50 mL. Yield: 1.40 g (85%), mp: 143–145° C.

Boc-Gly-Pro-ONSu: Boc-Gly-Pro-OH: 1.36 g (5.0 mmol), $CH_3CN$: 30 mL. Yield: 1.70 g (92%), $[\alpha]_D$=−65.2° C.=1.12 dioxane, mp: amorphous.

Boc-Pro-Gly-ONSu: Boc-Pro-Gly-OH: 1.36 g (5.0 mmol), $CH_3CN$: 30 mL. Yield: 1.80 g (97%), $[\alpha]_D$=−43.7° C.=1.11 dioxane, mp: amorphous.

Boc-Glu(O$^t$Bu)-$(Gly)_n$-Val-Arg-pNA.HCl (SEQ ID NO: 11)

a) n=0

Boc-Glu(O$^t$Bu)-ONSu (0.202 g, 0.505 mmol, 1.39 eq.), 2HCl.H-Val-Arg-pNA (0.169 g, 0.362 mmol) were dissolved in DMF (10 mL) and DIPEA (100 μL, 0.57 mmol, 1.59 eq.) was added to start the reaction. The obtained reaction mixture was stirred for 16 hrs at room temperature. After this period of stirring, DMF was evaporated under reduced pressure and the residue was diluted with BuOH (25 mL). The organic solution was subsequently washed with $H_2O$, saturated $NaHCO_3$ and $H_2O$ (three times 10 mL each) and evaporated in vacuo. The obtained residue was purified by counter current distribution with BuOH/AcOH/$H_2O$ 4:1:5 v/v/v as solvent combination. The pure product fractions were collected and evaporated in vacuo. The residue was lyophilized from AcOH. Yield: 226 mg (87%), $R_f$(BuOH/AcOH/$H_2O$ 4:1:1 v/v/v): 0.81 (K=6.81), $[\alpha]_D$=−43.60 c=0.39 MeOH, $^1H$ NMR ($CD_3OD$): δ=0.97/0.99 (d, 6H γ-$CH_3$/γ'-$CH_3$-Val); 1.43 (s, 18H, Boc(9H)/O$^t$Bu(9H)); 1.51–2.12 (bm, 7H, β-$CH_2$-Glu/β-CH-Val/β-$CH_2$-Arg/γ-$CH_2$-Arg); 2.34 (m, 2H, γ-$CH_2$-Glu); 3.23 (m, 2H, δ-$CH_2$-Arg); 4.08 (m, 1H, α-CH-Glu); 4.16 (m, 1H, α-CH-Val); 4.54 (m, 1H, α-CH-Arg); 7.86/7.88–8.21/8.23 (dd, 4H, arom pNA).

b) n=1

Obtained as described for a)

Quantities used: Boc-Glu(O$^t$Bu)-ONSu: 0.205 g (0.511 mmol, 1.01 eq.), 2HCl.H-Gly-Val-Arg-pNA: 0.265 g (0.506 mmol), DIPEA: 200 μL (1.14 mmol, 2.25 eq.) in 10 mL DMF. Yield: 352 mg (90%), $R_f$(BuOH/AcOH/$H_2O$ 4:1:1 v/v/v): 0.78 (K=10.52), $[\alpha]_D$=−30.0° C.=0.28 MeOH, $^1H$ NMR ($CD_3OD$): δ=0.99/1.01 (d, 6H, γ-$CH_3$/γ'-$CH_3$-Val);

1.43 (s, 18H, Boc(9H)/O$^t$Bu(9H)); 1.69–2.16 (bm, 7H, β-$CH_2$-Glu/β-CH-Val/β-$CH_2$-Arg/γ-$CH_2$-Arg); 2.31 (m, 2H, γ-$CH_2$-Glu); 3.24 (m, 2H, δ-$CH_2$-Arg); 3.90 (dd, 2H, $CH_2$-Gly); 4.04 (m, 1H, α-CH-Glu); 4.16 (d, 1H, α-CH-Val); 4.52 (m, 1H, α-CH-Arg); 7.89/7.91–8.20/8.22 (dd, 4H, arom pNA).

c) n=2

Obtained as described for a)

Quantities used: Boc-Glu(O$^t$Bu)-Gly-ONSu: 0.115 g (0.251 mmol, 1.23 eq.), 2HCl.H-Gly-Val-Arg-pNA: 0.107 g (0.204 mmol), DIPEA: 86 μL (0.50 mmol, 2.45 eq.) in 10 mL DMF. Yield: 134 mg (79%), $R_f$(BuOH/AcOH/$H_2O$ 4:1:1 v/v/v): 0.74 (K=6.81), $[α]_D$=−29.1° C.=0.17 MeOH, $^1H$ NMR ($CD_3OD$): δ=0.91 (dd, 6H, γ-$CH_3$/γ'-$CH_3$-Val); 1.33 (m, 20H, Boc(9H)/O$^t$Bu(9H)/γ-$CH_2$-Arg); 1.62 (m, 1H, β-CH-Val); 1.76 (m, 2H, β-$CH_2$-Glu); 1.93/2.06 (dm, 2H, β-$CH_2$-Arg); 2.24 (m, 2H, γ-$CH_2$-Glu); 3.14 (m, 2H, δ-$CH_2$-Arg); 3.80 (dd, 4H, $CH_2$-Gly (2×2H)); 3.92 (m, 1H, α-CH-Glu); 4.03 (d, 1H, α-CH-Val); 4.46 (m, 1H, α-CH-Arg); 7.79/8.12 (dd, 4H, arom pNA). Boc-(Gly)$_x$-(Pro)$_y$-(Gly)$_z$-Val-Arg-pNA.HCl (SEQ ID NO: 18) a) x=3, y=z=0

Boc-Gly-Gly-ONSu (98.4 mg, 0.299 mmol, 1.18 eq.), 2HCl.H-Gly-Val-Arg-pNA (132.1 mg, 0.253 mmol) were dissolved in DMF (10 mL) and DIPEA (86 μL, 0.49 mmol, 1.94 eq.) was added. After stirring for 16 hrs at room temperature, DMF was removed under reduced pressure. The residue was purified by counter current extraction with BuOH/AcOH/$H_2O$ 4:1:5 v/v/v as the solvent combination. The product fractions were collected and evaporated in vacuo and subsequently lyophilized from AcOH. Yield: 148.2 mg (81%), $R_f$(BuOH/AcOH/$H_2O$ 4:1:1 v/v/v): 0.55 (K=2.97), $[α]_D$=−30.0° C.=0.28 MeOH, $^1H$ NMR ($CD_3OD$): δ=0.90 (dd, 6H, γ-$CH_3$/γ'-$CH_3$-Val); 1.34 (s, 9H, Boc); 1.61 (m, 2H, γ-$CH_2$-Arg); 1.75 (m, 1H, β-CH-Val); 1.84/2.04 (dm, 2H, β-$CH_2$-Arg); 3.14 (m, 2H, δ-$CH_2$-Arg); 3.66–3.92 (3×dd, 6H, $CH_2$-Gly (3×2H)); 4.04 (d, 1H, α-CH-Val); 4.44 (m, 1H, α-CH-Arg); 7.78/8.13 (dd, 4H, arom pNA).

b) x=y=z=1

Obtained as described for a)

Quantities used: Boc-Gly-Pro-ONSu: 110.0 mg (0.298 mmol, 1.17 eq.), 2HCl.H-Gly-Val-Arg-pNA: 136.0 mg (0.260 mmol), DIPEA: 86 μL (0.50 mmol, 1.92 eq.) in 10 mL DMF. Yield: 145.8 mg (76%), $R_f$(BuOH/AcOH/$H_2O$ 4:1:1 v/v/v): 0.50 (K=3.75), $[α]_D$=−49.4° C.=0.17 MeOH, $^1H$ NMR ($CD_3OD$): δ=0.90 (dd, 6H, γ-$CH_3$/γ'-$CH_3$-Val); 1.32 (s, 9H, Boc); 1.63–2.12 (bm, 9H, δ-$CH_2$-Arg/β-CH-Val/γ-$CH_2$-Arg/$CH_2$-Pro (2×2H)); 3.14 (m, 2H, δ-$CH_2$-Arg); 3.52 (m, 2H, N—$CH_2$-Pro); 3.71–3.89 (dd, 4H, $CH_2$-Gly (2×2H)); 4.04 (d, 1H, α-CH-Val); 4.28 (m, 1H, α-CH-Pro); 4.43 (m, 1H, α-CH-Arg); 7.81/8.12 (dd, 4H, arom pNA).

c) x=0, y=1, z=2

Obtained as described for a)

Quantities used: Boc-Pro-Gly-ONSu: 101.2 mg (0.274 mmol, 1.05 eq.), 2HCl.H-Gly-Val-Arg-pNA: 132.7 mg (0.254 mmol), DIPEA: 86 μL (0.50 mmol, 1.92 eq.) in 10 mL DMF. Yield: 158.9 mg (81%), $R_f$(BuOH/AcOH/$H_2O$ 4:1:1 v/v/v): 0.65 (K=4.90), $[α]_D$=−42.1° C.=0.24 MeOH, $^1H$ NMR ($CD_3OD$): δ=0.91 (dd, 6H, γ-$CH_3$/γ'-$CH_3$-Val); 1.36 (s, 9H, Boc); 1.63–2.12 (bm, 9H, β-$CH_2$-Arg/β-CH-Val/γ-$CH_2$-Arg/$CH_2$-Pro (2×2H)); 3.14 (m, 2H, δ-$CH_2$-Arg); 3.38 (m, 2H, N—$CH_2$-Pro); 3.82 (d, 4H, $CH_2$-Gly (2×2H)); 4.04 (d, 1H, α-CH-Val); 4.09 (m, 1H, α-CH-Pro); 4.45 (m, 1H, α-CH-Arg); 7.78/8.13 (dd, 4H, arom pNA).

2HCl.H-(Gly)$_x$-(Pro)$_y$-(Gly)$_z$-Val-Arg-pNA (SEQ ID NO: 19)

a) x=3, y=z=0

Boc-Gly-Gly-Gly-Val-Arg-pNA.HCl (100.7 mg, 0.140 mmol) was dissolved in AcOH (5 mL) and 3.5 M HCl in EtOAc (5 mL) was added. After stirring for 2 hrs at room temperature, the acid was quenched by the addition of tert.-BuOH (20 mL) and the solution was evaporated in vacuo. The residue was coevaporated with tert.-BuOH (once 10 mL) and MeOH (twice 10 mL). The foamy residue was dissolved in $H_2O$ (25 mL) and subsequently washed with $CH_2Cl_2$ (twice 10 mL) and diethyl ether (once 20 mL). The aqueous phase was lyophilized and the crude deprotected product was used as obtained. Yield: 90.4 mg (quant.), $R_f$(BuOH/AcOH/$H_2O$ 4:1:1 v/v/v): 0.21.

b) x=y=z=1

Obtained as described for a)

Quantities used: Boc-Gly-Pro-Gly-Val-Arg-pNA.HCl (SEQ ID NO: 21): 110.6 mg (0.146 mmol). Yield: 110.1 mg (quant.), $R_f$(BuOH/AcOH/$H_2O$ 4:1:1 v/v/v): 0.15.

c) x=0, y=1, z=2

Obtained as described for a)

Quantities used: Boc-Pro-Gly-Gly-Val-Arg-pNA.HCl (SEQ ID NO: 22): 110.9 mg (0.146 mmol). Yield: 88.1 mg (87%), $R_f$(BuOH/ACOH/$H_2O$ 4:1:1 v/v/v): 0.15.

Boc-Glu(O$^t$Bu)-(Gly)$_x$-(Pro)$_y$-(Gly)$_z$-Val-Arg-pNA.HCl (SEQ ID NO: 23)

a) x=3, y=z=0

Boc-Glu(O$^t$Bu)-ONSu (56.5 mg, 0.142 mmol, 1.03 eq.) and 2HCl.H-Gly-Gly-Gly-Val-Arg-pNA (SEQ ID NO: 24) (90 mg, 0.138 mmol) were dissolved in DMF (10 mL). The reaction was started by the addition of DIPEA (50 μL, 0.294 mmol, 2.13 eq.) and kept overnight at room temperature. The next day, DMF was removed under reduced pressure and the residue was diluted with BuOH (20 mL). The organic solution was subsequently washed with $H_2O$, saturated $NaHCO_3$, $H_2O$, and saturated NaCl (three times 5 mL each). The solvent was removed under reduced pressure and the residue was dissolved in AcOH and lyophilized. The product was purified by counter current distribution with BuOH/AcOH/$H_2O$ 4:1:5 v/v/v as the solvent system. The pure product fractions were collected, evaporated in vacuo and lyophilized from AcOH. Yield: 102.2 mg (82%), $R_f$(BuOH/AcOH/$H_2O$ 4:1:1 v/v/v): 0.60 (K=5.91), $[α]_D$=−26.3° C.=0.24 MeOH, $^1H$ NMR ($CD_3OD$): δ=0.99/1.01 (dd, 6H, γ-$CH_3$/γ'-$CH_3$-Val); 1.45 (s, 18H, Boc(9H)/O$^t$Bu(9H)); 1.71 (m, 2H, γ-$CH_2$-Arg); 1.86 (m, 2H, β-$CH_2$-Arg); 2.04 (m, 2H, β-CH-Val/β-$CH_2$-Glu(1H)); 2.16 (m, 1H, β-$CH_2$-Glu(1H)); 2.34 (m, 2H, γ-$CH_2$-Glu); 3.24 (m, 2H, δ-$CH_2$-Arg); 3.84/3.87–3.88/3.92//3.87//3.97/3.99–4.03/4.04 (dd/s/dd, 6H, $CH_2$-Gly(3×2H)); 4.06 (m, 1H, α-CH-Glu); 4.12 (d, 1H, α-CH-Val); 4.54 (m, 1H, α-CH-Arg); 7.88/7.90–8.21/8.23 (dd, 4H, arom pNA).

b) x=y=z=1

Obtained as described for a)

Quantities used: Boc-Glu(O$^t$Bu)-ONSu: 57.6 mg (0.145 mmol, 1.01 eq.), 2HCl.H-Gly-Pro-Gly-Val-Arg-pNA: 100.0 mg (0.144 mmol), DIPEA: 50 μL (0.294 mmol, 2.04 eq.) in 10 mL DMF. Yield: 123.3 mg (91%), $R_f$(BuOH/AcOH/$H_2O$ 4:1:1 v/v/v): 0.55, $[α]_D$=−53.2° C.=0.24 MeOH, $^1H$ NMR ($CD_3OD$): δ=0.99/1.01 (dd, 6H, γ-$CH_3$/γ'-$CH_3$-Val); 1.45 (s, 18H, Boc(9H)/O$^t$Bu(9H)); 1.75 (bm, 4H, β-$CH_2$-Arg/γ-$CH_2$-Arg); 2.03 (bm, 5H, β-CH-Val/$CH_2$-Pro (2×2H)); 2.20 (m, 2H, β-$CH_2$-Glu); 2.32 (m, 2H, γ-$CH_2$-Glu); 3.23 (m, 2H, δ-$CH_2$-Arg); 3.60 (dm, 2H, N—$CH_2$-Pro); 3.85/3.90–4.00/

4.04 (dd, 2H, $CH_2$-Gly(Glu$^-$)); 4.07 (s, 2H, $CH_2$-Gly($^-$Val)); 4.12 (m, 2H, α-CH-Val/α-CH-Glu); 4.42 (m, 1H, α-CH-Pro); 4.49 (m, 1H, α-CH-Arg); 7.93/7.96–8.18/8.21 (dd, 4H, arom pNA).

c) x=0, y=1, z=2

Obtained as described for a)

Quantities used: Boc-Glu(O$^t$Bu)-ONSu: 50.7 mg (0.132 mmol, 1.04 eq.), 2HCl.H-Pro-Gly-Gly-Val-Arg-pNA: 88 mg (0.127 mmol), DIPEA: 50 μL (0.294 mmol, 2.31 eq.) in 10 mL DMP. Yield: 94.6 mg (79%), $R_f$(BuOH/AcOH/$H_2O$ 4:1:1 v/v/v): 0.67 (K=5.91), $[\alpha]_D$=−40.0° C.=0.14 MeOH, $^1$H NMR ($CD_3OD$): δ=0.99/1.00–1.01/1.02 (dd, 6H, γ-$CH_3$/γ'-$CH_3$- Val); 1.46 (s, 18H, Boc(9H)/O$^t$Bu(9H)); 1.73 (m, 2H, γ-$CH_2$-Arg); 1.87 (m, 1H, β-$CH_2$-Arg(1H)); 2.00 (m, 5H, β-$CH_2$-Arg(1H)/$CH_2$-Pro (2×2H)); 2.13 (m, 2H, β-CH-Val/β-$CH_2$-Glu(1H)); 2.25 (m, 1H, β-$CH_2$-Glu(1H)); 2.34 (m, 2H, γ-$CH_2$-Glu); 3.23 (m, 2H, δ-$CH_2$-Arg); 3.76 (m, 2H, N—$CH_2$-Pro); 3.89/3.93–3.97/4.01 (dd, 4H, $CH_2$-Gly(2×2H)); 4.12 (d, 1H, α-CH-Val); 4.37 (m, 1H, α-CH-Glu); 4.43 (m, 1H, α-CH-Pro); 4.55 (m, 1H, α-CH-Arg); 7.88/7.90–8.21–8.23 (dd, 4H, arom pNA).

Deprotection of the N-terminal Boc-Glu(O$^t$Bu)$^-$ Residue

The Boc- and tert.-Bu function were removed by the method of Sieber et al.[21] In general: the protected peptide was dissolved in pre-cooled (−5° C.) concentrated HCl (37%). After stirring for 5 min at 0° C., the reaction mixture was diluted with AcOH (10 volumes) and lyophilized, dissolved in $H_2O$ and lyophilized again. The crude deprotected product was purified by counter current distribution with BuOH/AcOH/$H_2O$ 4:1:5 v/v/v as the solvent system. The pure product fractions were collected, evaporated in vacuo and lyophilized from $H_2O$. The fluffy, off-white products were further dried in a vacuum desiccator on NaOH-pellets to reduce the slightly hygroscopic character of the fresh lyophilisates.

2HCl.H-Glu-Val-Arg-pNA (3d)

Yield: 69.1 mg (81%), $R_f$(BuOH/AcOH/$H_2O$ 4:1:1 v/v/v): 0.36 (K=0.37), $[\alpha]_D$=−43.0° C.=0.10 MeOH, $^1$H NMR ($D_2O$): δ=0.78 (dd, 6H, γ-$CH_3$/γ'-$CH_3$-Val); 1.52 (m, 2H, γ-$CH_2$-Arg); 1.72 (m, 2H, β-$CH_2$-Arg(1H)/β-CH-Val); 1.94 (m, 3H, β-$CH_2$-Arg(1H)/β-$CH_2$-Glu); 2.25 (m, 2H, γ-$CH_2$-Glu); 3.04 (m, 2H, δ-$CH_2$-Arg); 3.93 (m, 1H, α-CH-Glu); 4.00 (d, 1H, α-CH-Val); 4.28 (m, 1H, α-CH-Arg); 7.51/8.07 (dd, 4H, arom pNA).

2HCl.H-Glu-Gly-Val-Arg-pNA (3e)

Yield: 71 mg (84%), $R_f$(BuOH/AcOH/$H_2O$ 4:1:1 v/v/v): 0.34 (K=0.36), $[\alpha]_D$=−40.8° C.=0.26 MeOH, $^1$H NMR ($CD_3OD$): δ=0.98/1.01 (dd, 6H, γ-$CH_3$/γ'-$CH_3$-Val); 1.70 (m, 2H, γ-$CH_2$-Arg); 1.84 (m, 1H, β-CH-Val); 1.97/2.13 (dm, 2H, β-$CH_2$-Arg); 2.13 (m, 2H, β-$CH_2$-Glu); 2.56 (m, 2H, γ-$CH_2$-Glu); 3.24 (m, 2H, δ-$CH_2$-Arg); 3.97/4.00–4.05/4.09 (dd, 2H, $CH_2$-Gly); 4.02 (m, 1H, α-CH-Glu); 4.23 (d, 1H, α-CH-Val); 4.53 (m, 1H, α-CH-Arg); 7.86/7.89–8.21/8.23 (dd, 4H, arom pNA).

2HCl.H-Glu-Gly-Gly-Val-Arg-pNA (3f)

Yield: 81.3 mg (94%), $R_f$(BuOH/AcOH/$H_2O$ 4:1:1 v/v/v): 0.28 (K=0.34), $[\alpha]_D$=−26.9° C.=0.13 MeOH, AAA: Glu (1.00) 1.11; Gly(2.00) 1.97; Val(1.00) 0.99; Arg(1.00) 0.93, $^1$H NMR ($D_2O$): δ=0.74 (dd, 6H, γ-$CH_3$/γ'-$CH_3$-Val); 1.52 (m, 2H, γ-$CH_2$-Arg); 1.68 (m, 1H, β-CH-Val); 1.77/1.89 (dm, 2H, β-$CH_2$-Arg); 1.99 (m, 2H, β-$CH_2$-Glu); 2.37 (m, 2H, γ-$CH_2$-Glu); 3.05 (m, 2H, δ-$CH_2$-Arg); 3.84 (m, 4H, $CH_2$-Gly(2×2H)); 3.94 (m, 2H, α-CH-Val/α-CH-Glu); 4.29 (m, 1H, α-CH-Arg); 7.52/8.06 (dd, 4H, arom pNA).

2HCl.H-Glu-Gly-Gly-Gly-Val-Arg-pNA (3g)

Yield: 71.3 mg (91%), $R_f$(BuOH/AcOH/$H_2O$ 4:1:1 v/v/v): 0.20 (K=0.28), $[\alpha]_D$ =−16.4° C.=0.14 MeOH, AAA: Glu (1.00) 1.18; Gly(3.00) 2.92; Val(1.00) 0.99; Arg(1.00) 0.91, $^1$H NMR ($D_2O$): δ=0.78 (dd, 6H, γ-$CH_3$/γ'-$CH_3$-Val); 1.54 (m, 2H, γ-$CH_2$-Arg); 1.73/1.82 (dm, 2H, β-$CH_2$-Arg); 1.93 (m, 1H, β-CH-Val); 2.04 (m, 2H, β-$CH_2$-Glu); 2.42 (dd, 2H, γ-$CH_2$-Glu); 3.08 (dd, 2H, δ-$CH_2$-Arg); 3.81/3.89 (m, 6H, $CH_2$-Gly(3×2H)); 3.98 (m, 2H, α-CH-Val/α-CH-Glu); 4.23 (m, 1H, α-CH-Arg); 7.55/8.09 (dd, 4H, arom pNA).

2HCl.H-Glu-Gly-Pro-Gly-Val-Arg-pNA (3h)

Yield: 79.6 mg (90%), $R_f$(BuOH/AcOH/$H_2O$ 4:1:1 v/v/v): 0.17 (K=0.33), $[\alpha]_D$=−50.8° C.=0.12 MeOH, AAA: Glu (1.00) 1.18; Gly(2.00) 1.97; Pro(1.00) 1.04; Val(1.00) 0.94; Arg(1.00) 0.87, $^1$H NMR ($D_2O$): δ=0.78 (dd, 6H, γ-$CH_3$/γ'-$CH_3$-Val); 1.55 (m, 2H, γ-$CH_2$-Arg); 1.64–2.14 (bm, 9H, β-CH-Val/β-$CH_2$-Glu/β-$CH_2$-Arg/$CH_2$-Pro(2×2H)); 2.43 (m, 2H, γ-$CH_2$-Glu); 3.08 (m, 2H, δ-$CH_2$-Arg); 3.46 (m, 2H, N—$CH_2$-Pro); 3.80 (s, 2H, $CH_2$-Gly); 3.98 (m, 4H, α-CH-Val/α-CH-Glu/$CH_2$-Gly); 4.31 (m, 2H, α-CH-Arg/α-CH-Pro); 7.55/8.11 (dd, 4H, arom pNA).

2HCl.H-Glu-Pro-Gly-Gly-Val-Arg-pNA (3i)

Yield: 40.2 mg (92%), $R_f$(BuOH/AcOH/$H_2O$ 4:1:1 v/v/v): 0.16 (K=0.29), $[\alpha]_D$=−33.3° C.=0.11 MeOH, AAA: Glu (1.00) 1.35; Gly(2.00) 1.82; Pro(1.00) 1.05; Val(1.00) 0.92; Arg(1.00) 0.85, $^1$H NMR ($D_2O$) δ=0.79 (dd, 6H, γ-$CH_3$/γ'-$CH_3$-Val); 1.57 (m, 2H, γ-$CH_2$-Arg); 1.70–2.21 (bm, 9H, β-CH-Val/β-$CH_2$-Glu/β-$CH_2$-Arg/$CH_2$-Pro(2×2H)); 2.42 (m, 2H, γ-$CH_2$-Glu); 3.08 (m, 2H, δ-$CH_2$-Arg); 3.47 (m, 2H, N—$CH_2$-Pro); 3.61 (m, 1H, α-CH-Glu); 3.82 (dd, 4H, $CH_2$-Gly(2×2H)); 3.98 (d, 1H, α-CH-Val); 4.32 (m, 2H, α-CH-Arg/α-CH-Pro); 7.57/8.12 (dd, 4H, arom pNA).

RERERENCES

18. Tesser, G. I. and Balvert-Geers, I. C. (1975) *Int. J. Peptide Protein* Res. 7, 295–305.

19. Padmanabhan, K., Padmanabhan, K. P., Tulinsky, A., Park, C. H., Bode, W., Huber, R., Blankenship, D. T., Cardin, A. D. and Kisiel, W. (1993) *J. Mol. Biol.* 232, 947–966.

20. (a) Nakanishi, H., Chrusciel, R. A., Shen, R., Bertenshaw, S., Johnson, M. E., Rydel, T. J., Tulinsky, A. and Kahn, M. (1992) *Proc. Natl. Acad. Sci. USA* 89, 1705–1709; (b) Wu, T.-P., Yee, V., Tulinsky, A., Chrusciel, R. A., Nakanishi, H., Shen, R., Priebe, C. and Kahn, M. (1993) *Protein Eng.* 6, 471–478.

21. Sieber, P., Riniker, B., Brugger, M., Kamber, B. and Rittel, W. (1970) *Helv. Chim. Acta* 53, 2135–2150.

22. Schnabel, E. (1967) *Liebigs Ann. Chem.* 702, 188–196.

23. Brenner, M. and Huber, W. (1953) *Helv. Chim Acta* 36, 1109–1115.

24. Zervas, L. and Hamaladis, C. (1965) *J. Am. Chem. Soc.* 87, 99–104.

25. Moroder, L., Hallett, A., WŸnsch, E., Keller, O. and Wersin, G. (1976) *Hoppe Seylers Z. Physiol. Chem.* 357, 1651–1653.

26. Schröder, E. and Klieger, E. (1964) *Liebigs Ann. Chem.* 673, 196–207.

27. Anderson, G. W., Zimmerman, J. E. and Callahan, F. M. (1964) *J. Am. Chem. Soc.* 86, 1839–1842.

EXAMPLE 4

Continuous Registration of Thrombin Generation Curves Using Chromogenic Substrates In this example a set of 18 chromogenic substrates was tested on its application in the continuous registration of thrombin formation in plasma. The screening and selection procedure was the same as described in example 2.

Another obstacle encountered in the determination of the thrombin generation curve is the hydrolytic activity of the $\alpha_2$-macroglobulin-thrombin complex on small chromogenic substrates. This complex has no clotting activity but it disturbs the thrombin generation curve by its action on substrates which are small enough to be bound by this complex. To reduce the contribution of the $\alpha_2$-macroglobulin-thrombin complex to the optical density curve, we synthesized chromogenic substrates up to six amino acid residues in length in the assumption that these substrates have a decreased access to the active-site of thrombin due to steric hindrance caused by its complexation with $\alpha_2$-macroglobulin.

Materials and Methods

Materials

Chromogenic substrates: The syntheses of the substrates are described in example 3. The substrates were dissolved in distilled water to obtain 10 mM stock solutions. The concentration was determined at 316 nm using a molar extinction coefficient of 12,500. Stock solutions were stored in the dark at 4° C. Thrombin substrate SQ68 (malonyl-α-aminoisobutyryl-arginine p-nitroanilide methyl ester monohydrochloride, $CH_3O—CO—CH_2—CO$-Aib-Arg-pNA.HCl) was obtained from Serbio Laboratories, France. Heparin ($4^{th}$ international standard heparin) was obtained from the National Bureau of Standards and Control (London). Methylamine (40 wt.-% solution in $H_2O$), N,N-diisopropylethylamine and hydroxylamine hydrochloride were purchased from Merck (Darmstadt, Germany).

Phospholipids: Phospholipids required were 80 mol-% dioleoyl phosphatidyl choline and 20 mol-% dioleoyl phosphatidyl serine solutions in chloroform; they were obtained from Avanti Polar Lipids. They were used to prepare vesicles as described by Rosing et al.[4]

Buffers: Buffer A: 0.05 M Tris-HCl, 0.1 M NaCl pH=7.35 containing 0.5 g/L bovine serum albumin (Sigma). Buffer B: buffer A containing additional EDTA (20 mM) pH=7.90.

Enzyme preparations: Pure human α-thrombin and human factor Xa samples were generous gifts of Dr. T. Lindhout (University of Limburg, Maastricht, The Netherlands). The euglobulin thrombin fraction was prepared from defibrinated plasma by acid precipitation at low ionic-strength as described by Josso and Prou-Wartelle[5]. The precipitate was dissolved in half the original volume of buffer A, containing 0.02 M trisodium citrate.

Plasma: Plasma was prepared by collecting 9 parts of blood (from 10 healthy donors) on 1 part of 0.13 M trisodium citrate. Following centrifugation at 900 g (15° C., 15 min) and 10,000 g (15° C., 15 min) the obtained plasma was pooled and centrifuged at 4° C. for 1 hour at 23,000 g; this plasma was stored at −80° C. Plasma was defibrinated by mixing an aliquot of plasma with 1/50 volume of reptilase (Laboratories Stago, Asnieres, France; the solution was made as instructed by the manufacturer), letting a clot form for 10 min at 37° C. followed by 10 min on ice. The fibrin clot was removed by winding it on a plastic spatula. $Al(OH)_3$ treated plasma: 1 mL defibrinated plasma was incubated with 200 μL $Al(OH)_3$ suspension (0.25 g/mL in 0.15 M NaCl) at 37° C. for 5 min. After centrifugation (3 min) the supernatant was used in the experiments. $AL(OH)_3$ treatment removes all vitamin K dependent clotting factors (FII, VII, IX, X, protein C and protein S). Coagulation factor XI and XII deficient plasmas were generous gifts of Dr. G. Tans (University of Limburg, Maastricht, The Netherlands).

Tissue factor: Recombinant tissue factor (RECOMPLASTIN S, Dade, Baxter Diagnostics Inc., Deerfield Ill., U.S.A.) was used as a trigger for coagulation. The solution was prepared according to the instructions of the manufacturer. The intrinsic pathway was triggered by Actin FS, activated PTT reagent from soy phosphatides, containing $1.10^{-4}$ M ellagic acid and was obtained from Baxter. Contact activation was started by the addition of kaolin (0.5 mg/mL in 0.15 M NaCl); kaolin (kaolin lèger) was provided by B.L.B. Laboratoires du Bois de Boulogne (Puteaux, France).

Methods

Kinetic parameters: The hydrolysis experiments were run in buffer A at 37° C. The liberation of p-nitroaniline was monitored at 405 nm in a dual wavelength (405–546 nm) spectrophotometer made in our workshop, using a personal computer for data recording. In a polystyrene microcuvette (total volume 500 μL), buffer A and substrate solution were added to obtain a final substrate concentration between 200 to 2000 μM. After 5 min of incubation at 37° C., enzyme solution was added to achieve a final concentration between 0.5 to 50 nM. The measurement was carried out at 37° C. in a thermostated cuvette-holder. The Michaelis constant ($K_m$) and the catalytic constant ($k_{cat}$) were obtained by measuring the initial reaction velocities at different substrate concentrations. The data obtained were fitted by linear regression on the Michaelis-Menten equation.

Continuous registration of the thrombin generation curve: Extrinsic pathway: In a polystyrene microcuvette were added: 400 μL defibrinated plasma, 20 μL of a 45 μM phospholipid solution (final concentration: 1.5 μM) and 140 μL of buffer A which contains the substrate at the desired final concentration (500 μM). After 4 min of incubation at 37° C., 20 μL tissue factor (undiluted) was added. Thrombin generation was started by adding 20 μL of a 0.5 M $CaCl_2$ solution (final concentration: 16.67 mM); during the measurement the temperature was kept at 37° C. The optical density was monitored at 405 nm. From the obtained optical density curve, the first derivative was calculated giving the enzyme concentration during the measurement. Intrinsic pathway: 400 μL defibrinated plasma, 110 μL buffer A (eventually containing the substances to be tested) and 40 μL Actin FS (undiluted) were added in a plastic microcuvette, intensively mixed and incubated at 37° C. during 4 min. Then 30 μL of a 10 mM substrate solution (final concentration: 500 μM), followed by 20 μL of a 0.5 M $CaCl_2$ solution (final concentration: 16.7 mM) were added (both solutions were prewarmed at 37° C. for 4 min). The optical density was measured at 37° C. at 405 nm during 20 min. Contact activation: 400 μL defibrinated plasma, 100 μL buffer A (eventually containing the substances to be tested), 9 μL of a 100 μM phospholipid solution (final concentration: 1.5 μM) and 40 μL kaolin (0.5 mg/mL) were added in a plastic microcuvette, intensively mixed and incubated at 37° C. during 4 min. (It was not necessary to remove kaolin by centrifugation.) Then 30 μL of a 10 mM substrate solution (final concentration: 500 μM), followed by 20 μL of a 0.5 M $CaCl_2$ solution (final concentration: 16.7 mM) were added (both solutions were prewarmed at 37° C. for 4 min). The optical density was measured at 37° C. at 405 nm during 25 min.

Decay constants of thrombin in plasma: To 120 μL defibrinated plasma was added: 50 μL of buffer A which contained the substances to be tested. To this mixture was added 10 μL of a thrombin preparation to achieve a final concentration of 100 nM. At regular time intervals (5–10 s) 10 μL samples were subsampled into 490 μL buffer B which contained 200 μM of S2238 to determine thrombin activity. After 2 min the reaction was stopped by adding 300 μL 1M citric acid. The moment of sampling and stopping were recorded on a personal computer with pushbutton-equipped pipettes. The optical density was read at 405 nm and the obtained amidolytic activities were used to calculate the decay constants. The obtained decay constant is the sum of the decay constants of the reaction of thrombin with antithrombin III ($k_1$) and $\alpha_2$-macroglobulin ($k_2$).

Manual determination of thrombin generation in plasma: Extrinsic pathway: To 480 μL defibrinated plasma were added: 172 μL buffer A which contained the substrate at concentrations between 0 to 2000 μM and 20 μL of a 54 μM phospholipid solution (final concentration: 1.5 μM). After incubation for 4 min at 37° C., 24 μL tissue factor (undiluted) was added. Thrombin formation started at zero time by adding 24 μL of a 0.5 M $CaCl_2$ solution (final concentration: 16.67 mM). At regular time intervals of 12 s samples of 10 μL were subsampled as described above. From the amidolytic activities thus obtained, the thrombin generation curve can be drawn. The decay constant $k_2$ can be calculated from these data in an alternative way, see reference 6 for further details.

Influence of the substrate on the prothrombinase-compzex: With the obtained decay constants and from the curves obtained by the subsampling method we calculated the course of prothrombin conversion and the course of prothrombinase concentration.

Results

Kinetic parameters: The $K_m$ and $k_{cat}$ values for each substrate were determined at an enzyme concentration of 0.5–50 nM (thrombin) and 50 nM factor Xa. From the initial reaction velocities, measured for at least six substrate concentrations between 200 and 2000 μM, the $K_m$ and $k_{cat}$ values were calculated by linear regression on the Michaelis-Menten curve. Table 3 gives an overview of the kinetic parameters of the different substrates hydrolyzed by thrombin and by factor Xa in buffer A.

Continuous registration of the thrombin generation curve: The continuous thrombin generation curves of substrates, entries 4 (SQ68), 5, and 16 are given in FIG. 17 (extrinsic pathway) respectively FIG. 18 (intrinsic pathway).

Decay constants: The decay constants of thrombin in the presence of Msc-Val-Arg-pNA.HCl and 2HCl.H-Glu-Gly-Gly-Val-Arg-pNA are given in tables 8 and 9. In both cases, inhibition of thrombin by AT-III is more efficient than when SQ68 is present.

Manual determination of thrombin formation and the influence of substrate on the prothrombinase-complex: The thrombin generation curves obtained by the subsampling method were determined. From these curves and the decay constants, the course of the concentration of the prothrombinase complex was calculated. Both substrates neither influenced the manual thrombin generation curve nor showed inhibitory activity on the prothrombinase complex.

Thrombin generation curves in the presence of high heparin concentrations: Some examples of thrombin generation curves measured in the presence of different heparin concentrations are given in FIGS. 2, 19 and 20. The substrates where chosen to cover a continuous range of heparin concentrations up to 5 U ISH/mL.

Thrombin generation curves in the presence of hydroxylamine: Hydroxylamine was added to the plasma sample as a selective denaturating agent of $\alpha_2$-macroglobulin. The influence of added hydroxylamine on the thrombin generation curve as measured in the continuous assay is given in FIG. 3. Correct thrombin generation curves are obtained at all concentrations of hydroxylamine used. Already at 25 mM hydroxylamine the residual amidolytic activity of the $\alpha_2$M-thrombin complex is substantially reduced.

Decay constants and the influence of hydroxylamine on the prothrombinase complex: To check if hydroxylamine has any inhibitory activity on the coagulation cascade, a thrombin generation curve was determined via the subsampling method. The decay constants of thrombin in the presence of hydroxylamine (table 4) were determined and were used to calculate the course of the prothrombinase concentration. From these experiments it was concluded that hydroxylamine did not influence the coagulation cascade.

Continuous registration of thrombin generation curves in non-defibrinated plasma: In FIG. 5 an example of a thrombin generation curve in non-defibrinated plasma is given. Hydroxylamine was used to denaturate $\alpha_2$-macroglobulin but it also makes the defibrinating step redundant because a clear gel is formed, so the measurement is not disturbed by formation of an incipient turbidity.

In a preliminary experiment, serum was used as enzyme source (thrombin-$\alpha_2$-macroglobulin-complex) and the substrates did not show a significant reduction of the hydrolysis rate. From this it was clear that a substrate of six amino acids is still too small to be excluded from the active-site of thrombin complexed with $\alpha_2$-macroglobulin. The most promising compound was entry 16, which is predominantly attacked by thrombin; having the lowest susceptibility for factor Xa.

From these thrombin generation curves, substrates Msc-Val-Arg-pNA.HCl (5) and 2HCl.H-Glu-Gly-Gly-Val-Arg-pNA (16) were selected as most promising compounds. The manual thrombin generation curves showed a higher amidolytic activity at higher substrate concentration. But more important, each curve showed that the maximum was reached at the same time-point: indicating no feedback-loop inhibition! From the decay constants and the manual thrombin generation curves the prothrombinase activity could be calculated. Again no inhibition of the prothrombinase activity or feedback-loop activation was observed. From these data it was concluded that Msc-Val-Arg-pNA.HCl and 2HCl.H-Glu-Gly-Gly-Val-Arg-pNA are most promising compounds to be used as substrates in the continuous registration of thrombin formation in plasma.

Thrombin generation curves were recorded using compounds 5, 9 and 20 and heparinized plasma; they are represented in FIG. 6. It must be realized that Boc-Gly-Val-Arg-pNA.HCl (9) and 2HCl.H-D-Phe-Pro-Lys-pNA (20) cannot be used in the continuous assay method without additional heparin. The substrate Msc-Val-Arg-pNA.HCl (5) can be used in the continuous assay at a heparin (ISH) concentration of 0.25 U/mL. Boc-Gly-Val-Arg-pNA.HCl gives a correct thrombin generation curve up to 2 U ISH/mL. Finally, 2HCl.H-D-Phe-Pro-Lys-pNA was used at a concentration of 5 U ISH/mL. Incipient turbidities hampered the determination of the thrombin generation curve at higher heparin concentrations. Generally, when heparin is present in plasma, the substrate used should become a better thrombin substrate (lower $K_m$, higher $k_{cat}$) if the heparin concentration increases.

From hydrolysis experiments with serum as enzyme source (thrombin-$\alpha_2$-macroglobulin-complex) and from the thrombin generation curves derived from them (FIGS. 1–3) it was concluded that substrates up to six amino acids showed no slower rates of hydrolysis.

We included hydroxylamine in the continuous assay to denaturate $\alpha_2$-macroglobulin and found the end level of thrombin-$\alpha_2$-macroglobulin significantly reduced, without affecting thrombin generation, already at a concentration of 25 mM of hydroxylamine, see FIG. 3. From these experiments it was concluded that hydroxylamine is ideally suited to denaturate $\alpha_2$-macroglobulin without affecting the coagulation cascade. This encouraging result prompted us to determine a thrombin generation curve in non-defibrinated plasma in the presence of hydroxylamine (FIG. 5). It was expected that thrombin-cleaved fibrinogen does not polymerize to form insoluble fibrin by the action of factor XIIIa in the presence of a large excess hydroxylamine. Factor XIIIa (a transglutaminase). evidently incorporates hydroxylamine in fibrin monomers instead of the standard $\epsilon$-amino group of a lysyl residue occurring in fibrin monomers. Incorporation of hydroxylamine results in the formation of a clear gel, permitting the passage of light. It is thus possible to measure a thrombin generation curve in non-defibrinated plasma with a zero endlevel of thrombin-$\alpha_2$-macroglobulin.

It was determined that in this system even the effect of heparin (0.05 U ISH/mL) is measurable.

REFERENCES

4. Rosing, J., Tans, G., Covers-Riemslag, J. W. P., Zwaal, R. F. A. and Hemker, H. C. (1980) *J. Biol. Chem.* 255, 274–283.

5. Josso, F. and Prou-Wartelle, O. (1972) In: *Techniques en hematologie*, Alagille, D. et al. (Eds.), 101–108, Paris, France.

6. Hemker, H. C., Willems, G. M. and B_guin, S. (1986) *Thromb. Haemostas.* 56, 9–17.

TABLE 1

Kinetics of hydrolysis of a number of defined substrates by human $\alpha$-thrombin in buffer A at 37° C.

| No | Substrate | [S] $\mu$M | [E] nM | $K_m$ $\mu$M | $k_{cat}$ $s^{-1}$ | $k_{cat}/K_m$ $(Ms)^{-1}$ |
|---|---|---|---|---|---|---|
| 1 | 2HCl.H-D-Phe-Pip-Arg-pNA | 2–200 | 0.5 | 5.62 | 236.5 | 4.21E7 |
| 2 | 2HCl.H-D-Phe-Pro-Arg-pNA | 1–200 | 0.5 | 3.16 | 28.4 | 8.99E6 |
| 3 | 2HCl.H-D-Phe-Pip-Lys-pNA | 1–500 | 0.5 | 65.11 | 118.3 | 1.82E6 |
| 4 | 2HCl.H-D-Phe-Pro-Lys-pNA | 1–200 | 0.5 | 35.04 | 90.4 | 2.58E6 |
| 5 | 2HCl.H-D-Phe-Pip-Orn-pNA | 10–1000 | 25 | 419.9 | 4.64 | 1.11E4 |
| 6 | HCl.H-D-Phe-Pip-Nle-pNA | 10–200 | 50 | 943.3 | 11.4 | 1.21E4 |
| 7 | HCl.H-D-Phe-Pro-Nle-pNA | 20–500 | 25 | 87.9 | 6.66 | 7.54E4 |
| 8 | HCl.H-D-Phe-Pip-Glu-pNA | 25–2000 | 50 | 473.8 | 0.35 | 7.39E2 |
| 9 | 2HCl.H-Gly-Arg-pNA | 250–2000 | 50 | 2282 | 0.107 | 4.69E1 |
| 10 | 2HCl.H-Ala-Arg-pNA | 250–2000 | 50 | 1140 | 0.074 | 6.49E1 |
| 11 | 2HCl.H-D-Ala-Arg-pNA | 250–2000 | 100 | 4083 | 0.096 | 2.35E1 |
| 12 | 2HCl.H-Val-Arg-pNA | 250–2000 | 50 | 1239 | 0.23 | 1.86E2 |
| 13 | 2HCl.H-D-Val-Arg-pNA | 250–2000 | 50 | 4247 | 0.28 | 6.59E1 |
| 14 | MZ-Gly-Arg-pNA.HCl | 250–4000 | 100 | 2537 | 12.3 | 4.85E3 |
| 15 | MZ-Ala-Arg-pNA.HCl | 125–2000 | 100 | 1539 | 107.5 | 6.99E4 |
| 16 | MZ-D-Ala-Arg-pNA.HCl | 250–2000 | 100 | 1330 | 0.059 | 4.44E1 |
| 17 | MZ-Aib-Arg-pNA.HCl[a] | 250–2000 | 100 | 830 | 0.46 | 5.54E2 |
| 18 | MZ-Val-Arg-pNA.HCl | 125–2000 | 100 | 1007 | 14.4 | 1.43E4 |
| 19 | MZ-D-Val-Arg-pNA.HCl | 250–2000 | 100 | 1312 | 0.146 | 1.11E2 |
| 20 | MMZ-Gly-Arg-pNA.HCl | 250–2000 | 100 | 1737 | 6.60 | 3.80E3 |
| 21 | MMZ-Ala-Arg-pNA.HCl | 250–2000 | 100 | 666 | 16.5 | 2.48E4 |
| 22 | DMMZ-Gly-Arg-pNA.HCl | 250–2000 | 100 | 902 | 6.44 | 7.14E3 |
| 23 | DMMZ-Ala-Arg-pNA.HCl | 250–2000 | 100 | 565 | 4.08 | 7.22E3 |
| 24 | DEMZ-Gly-Arg-pNA.HCl | 250–2000 | 50 | 866.5 | 1.73 | 1.99E3 |
| 25 | βNS-Gly-Arg-pNA.HCl | 250–750 | 50 | — | NH | — |
| 26 | pTS-Gly-Arg-pNA.HCl | 250–2000 | 50 | — | NH | — |
| 27 | 2HCl.H-Gly-Val-Arg-pNA | 50–1000 | 1 | 1638 | 16.54 | 1.01E4 |
| 28 | Boc-Gly-Val-Arg-pNA.HCl | 5–1000 | 1 | 244 | 11.2 | 4.59E4 |

NH: not hydrolyzed by thrombin;
[a]from Hemker H.C. et al. (1993) Thromb. Haemostas 70, 617–624.

TABLE 2

Kinetics of hydrolysis of a defined number of substrates by human factor Xa in buffer A at 37° C.

| No | Substrate | [S] $\mu$M | [E] nM | $K_m$ $\mu$M | $k_{cat}$ $s^{-1}$ | $k_{cat}/K_m$ $(Ms)^{-1}$ |
|---|---|---|---|---|---|---|
| 1 | 2HCl.H-D-Phe-Pip-Arg-pNA | 50–1500 | 10 | 174.4 | 7.49 | 4.29E4 |
| 2 | 2HCl.H-D-Phe-Pro-Arg-pNA | 50–2000 | 10 | 693 | 18.7 | 2.69E4 |
| 3 | 2HCl.H-D-Phe-Pip-Lys-pNA | 250–1500 | 25 | 963 | 0.61 | 6.31E2 |
| 4 | 2HCl.H-D-Phe-Pro-Lys-pNA | ND | — | — | — | — |
| 5 | 2HCl.H-D-Phe-Pip-Orn-pNA | ND | — | — | — | — |
| 6 | HCl.H-D-Phe-Pip-Nle-pNA | 5–500 | 25 | — | NH | — |
| 7 | HCl.H-D-Phe-Pro-Nle-pNA | ND | — | — | — | — |
| 8 | HCl.H-D-Phe-Pip-Glu-pNA | 250–1500 | 50 | — | NH | — |
| 9 | 2HCl.H-Gly-Arg-pNA | ND | — | — | — | — |
| 10 | 2HCl.H-Ala-Arg-pNA | ND | — | — | — | — |
| 11 | 2HCl.H-D-Ala-Arg-pNA | ND | — | — | — | — |
| 12 | 2HCl.H-Val-Arg-pNA | 250–2000 | 50 | — | NH | — |
| 13 | 2HCl.H-D-Val-Arg-pNA | ND | — | — | — | — |
| 14 | MZ-Gly-Arg-pNA.HCl | 250–3000 | 50 | 4700 | 55.0 | 1.17E4 |
| 15 | MZ-Ala-Arg-pNA.HCl | 250–3000 | 50 | 5593 | 51.7 | 9.25E3 |
| 16 | MZ-D-Ala-Arg-pNA.HCl | 250–2000 | 50 | 3084 | 0.088 | 2.85E1 |

TABLE 2-continued

Kinetics of hydrolysis of a defined number of substrates by human factor Xa in buffer A at 37° C.

| No | Substrate | [S] μM | [E] nM | $K_m$ μM | $k_{cat}$ $s^{-1}$ | $k_{cat}/K_m$ $(Ms)^{-1}$ |
|---|---|---|---|---|---|---|
| 17 | MZ-Aib-Arg-pNA.HCl[a] | 250–2000 | 50 | 3940 | 2.9 | 7.38E2 |
| 18 | MZ-Val-Arg-pNA.HCl | 250–2000 | 50 | 2569 | 6.42 | 2.50E3 |
| 19 | MZ-D-Val-Arg-pNA.HCl | 250–2000 | 50 | 1821 | 0.13 | 6.95E1 |
| 20 | MMZ-Gly-Arg-pNA.HCl | 250–3000 | 50 | 6402 | 43.9 | 6.86E3 |
| 21 | MMZ-Ala-Arg-pNA.HCl | 250–3000 | 50 | 7054 | 40.6 | 5.75E3 |
| 22 | DMMZ-Gly-Arg-pNA.HCl | 250–3000 | 50 | 2838 | 13.6 | 4.79E3 |
| 23 | DMMZ-Ala-Arg-pNA.HCl | 250–3000 | 50 | 22422 | 11.04 | 4.93E3 |
| 24 | DEMZ-Gly-Arg-pNA.HCl | 250–2000 | 50 | 2321 | 4.54 | 1.96E3 |
| 25 | βNS-Gly-Arg-pNA.HCl | 50–1500 | 10 | 116 | 2.00 | 1.73E4 |
| 26 | pTS-Gly-Arg-pNA.HCl | 25–1500 | 10 | 233 | 9.26 | 3.98E4 |
| 27 | 2HCl.H-Gly-Val-Arg-pNA | 250–1500 | 25 | 2679 | 3.51 | 1.31E3 |
| 28 | Boc-Gly-Val-Arg-pNA.HCl | 250–1500 | 25 | 959 | 1.90 | 1.98E3 |

NH: not hydrolyzed by factor Xa, ND: not determined

TABLE 3

Kinetic parameters of hydrolysis of the substrates by thrombin and factor Xa in buffer A at 37° C.

| | | Thrombin | | | Factor Xa | | |
|---|---|---|---|---|---|---|---|
| No | Substrate | $K_m$ | $k_{cat}$ | $k_{cat}/K_m$ | $K_m$ | $k_{cat}$ | $k_{cat}/K_m$ |
| 1 | 2HCl.H-Val-Arg-pNA | 1239 | 0.23 | 1.86E2 | — | NH | — |
| 2 | 2HCl.H-Val-Lys-pNA | — | NH | — | — | NH | — |
| 3 | MZ-Val-Arg-pNA.HCl | 1007 | 14.4 | 1.43E4 | 4082 | 10.1 | 2.47E3 |
| 4 | MZ-Aib-Arg-pNA.HCl | 830 | 0.46 | 5.54E2 | 3940 | 2.9 | 7.38E2 |
| 5 | Msc-Val-Arg-pNA.HCl | 882 | 0.79 | 8.94E2 | 9552 | 4.69 | 4.91E2 |
| 6 | Msc-Val-Lys-pNA.HCl | — | NH | — | — | NH | — |
| 7 | Msc-Val-Orn-pNA.HCl | — | NH | — | — | NH | — |
| 8 | Msc-Val-Nle-pNA | — | NH | — | — | NH | — |
| 9 | Boc-Gly-Val-Arg-pNA.HCl | 244 | 11.2 | 4.59E4 | 2679 | 3.51 | 1.31E3 |
| 10 | 2HCl.H-Gly-Val-Arg-pNA | 3234 | 25.4 | 7.88E3 | 4379 | 2.84 | 6.49E2 |
| 11 | 2HCl.H-Gly-Val-Lys pNA | 986 | 0.20 | 1.98E2 | — | NH | — |
| 12 | 2HCl.H-Gly-Val-Orn-pNA | — | NH | — | — | NH | — |
| 13 | HCl.H-Gly-Val-Nle-pNA | — | NH | — | — | NH | — |
| 14 | 2HCl.H-Glu-Val-Arg-pNA | 932 | 1.44 | 1.54E3 | 1510 | 1.07 | 7.09E2 |
| 15 | 2HCl.H-Glu-Gly-Val-Arg-pNA (SEQ ID NO:6) | 3274 | 3.51 | 1.07E3 | 1433 | 0.93 | 6.38E2 |
| 16 | 2HCl.H-EGGVR-pNA* | 1006 | 0.55 | 5.42E2 | 2186 | 0.42 | 1.92E2 |
| 17 | 2HCl.H-EGGGVR-pNA* | 379 | 0.27 | 7.04E2 | 1491 | 0.30 | 2.01E2 |
| 18 | 2HCl.H-EGPGVR-pNA* | 1074 | 9.07 | 8.44E3 | 2192 | 3.41 | 1.56E3 |
| 19 | 2HCl.H-EPGGVR-pNA* | — | NH | — | 961 | 0.45 | 4.68E2 |
| 20 | 2HCl.H-D-Phe-Pro-Lys-pNA[a] | 35 | 90 | 2.58E6 | — | NH | — |

*Amino acyl residues are denoted by their one-letter code; $K_m$ in μM; $k_{cat}$ in $s^{-1}$; $k_{cat}/K_m$ in $(Ms)^{-1}$;
NH: no hydrolysis

TABLE 4

Decay constants of euglothrombin in plasma in the presence of hydroxylamine.

| [S] mM | $k_{overall}$ $min^{-1}$ | $k_1$ $min^{-1}$ | $k_2$ $min^{-1}$ | $t_{1/2}$ s | $k_{2,M}$ $min^{-1}$ | $k_{1,corr}$ $min^{-1}$ | $(k_{1,corr})$ $min^{-1}$ |
|---|---|---|---|---|---|---|---|
| 0 | 3.240 | 2.908 | 0.332 | 12.84 | 0.271 | 2.799 | 1.508 |
| 25 | 1.312 | 1.253 | 0.059 | 31.70 | 0.057 | 1.085 | 0.585 |

$k_{overall} = k_1 + k_2 + 0.170$;
$k_1$: AT-III dependent decay of thrombin;
$k_2$: $\alpha_2$M dependent decay of thrombin;

TABLE 4-continued

Decay constants of euglothrombin in plasma in the presence of hydroxylamine.

| [S] mM | $k_{overall}$ $min^{-1}$ | $k_1$ $min^{-1}$ | $k_2$ $min^{-1}$ | $t_{1/2}$ s | $k_{2,M}$ $min^{-1}$ | $k_{1,corr}$ $min^{-1}$ | $(k_{1,corr})$ $min^{-1}$ |
|---|---|---|---|---|---|---|---|

$k_{overall}$, $k_1$ and $k_2$ are determined in a decay experiment;
$k_{2,M}$: $k_2$ determined by the subsampling method;
$k_{1,corr}$: $k_1$ after correcting for $k_{2,M}$ and 0.170;
$k_{1,corr,control}/1.508 = 2.799/1.508 = 1.856$ μM AT-III;
$(k_{1,corr}) = k_{1,corr}/1.856$.

TABLE 5

Time-point at which the maximum of the amidolytic activity, prothrombinase activity and thrombin concentration occur at different substrate concentrations.

| [S] | AA | t | PT | t | T | t |
|---|---|---|---|---|---|---|
| | | | Msc-Val-Arg-pNA.HCl: | | | |
| 0 | 342.44 | 60 | 1211 | 26 | 327.04 | 60 |
| 200 | 388.15 | 60 | 1119 | 24 | 371.24 | 60 |
| 500 | 387.15 | 60 | 1090 | 24 | 374.80 | 60 |
| 1000 | 456.42 | 60 | 1346 | 24 | 443.82 | 60 |
| | | | 2HCl.H-Glu-Gly-Gly-Val Arg-pNA: | | | |
| 0 | 346.79 | 60 | 1046 | 24 | 332.89 | 48 |
| 200 | 350.62 | 60 | 1086 | 24 | 335.47 | 60 |
| 500 | 376.42 | 60 | 1122 | 24 | 359.48 | 60 |
| 1000 | 409.85 | 60 | 1149 | 24 | 396.23 | 60 |
| | | | Hydroxylamine: | | | |
| 0 | 335.15 | 48 | 1242 | 24 | 322.17 | 48 |
| 25 | 383.88 | 72 | 1227 | 36 | 378.03 | 72 |

AA: amidolytic activity (mOD/min);
PT: prothrombinase concentration (mOD/min);
T: thrombin concentration (mOD/min);
t: time point at which maximum of concentration (amidolytic activity) is achieved (s);
[S]: substrate concentration in μM, hydroxylamine in mM.

TABLE 6

Decay constants of euglobulin thrombin in plasma in the presence of different substrate concentrations (2HCl.H-Val-Arg-pNA).

| [S] μM | $k_{overall}$ $min^{-1}$ | $k_1$ $min^{-1}$ | $k_2$ $min^{-1}$ | t½ s | $k_{2,M}$ $min^{-1}$ | $k_{1,corr}$ $min^{-1}$ | $(k_{1,corr})$ $min^{-1}$ |
|---|---|---|---|---|---|---|---|
| 0 | 2.520 | 2.137 | 0.383 | 16.51 | 0.298 | 2.052 | 1.508 |
| 100 | 2.317 | 2.064 | 0.253 | 17.95 | ND | ND | ND |
| 200 | 2.154 | 1.751 | 0.402 | 19.31 | 0.234 | 1.750 | 1.286 |
| 500 | 1.898 | 1.509 | 0.389 | 21.91 | 0.207 | 1.521 | 1.118 |
| 1000 | 1.879 | 1.676 | 0.204 | 27.12 | 0.199 | 1.510 | 1.110 |
| 1500 | 1.217 | 1.087 | 0.130 | 34.17 | ND | ND | ND |
| 2000 | 1.005 | 0.877 | 0.128 | 41.37 | ND | ND | ND |

$k_{overall} = k_1 + k_2 + 0.170$;
$k_1$: AT-III dependent decay of thrombin;
$k_2$: _$\alpha_2$M dependent decay of thrombin;
$k_{overall}$, $k_1$ and $k_2$ are determined in a decay experiment;
$k_{2,M}$: $k_2$ determined by the subsampling method;
$k_{1,corr}$: $k_1$ after correcting for $k_{2,M}$ and 0.170;
$k_{1,corr,control}/1.508 = 2.052/1.508 = 1.361$ μM AT-III;
$(k_{1,corr}) = k_{1,corr}/1.361$;
ND: not determined.

TABLE 7

Substrates of the type Y-Val-X-pNA fitting the active-site of thrombin like fibrinogen.

| Y | X | Code | Derived from | Code |
|---|---|---|---|---|
| H | Lys | 1a | H-Val-Arg-pNA (Ex 1) | 1 |
| Msc | Arg | 2a | MZ-Val-Arg-pNA (Ex.1) | 2 |
| Msc | Lys | 2b | | |
| Msc | Orn | 2c | | |
| Msc | Nle | 2d | | |
| | | | Compound I | |
| | | | Boc-Gly-Val-Arg-pNA (Ex 2) | 3' |
| | | | H-Gly-Val-Arg-pNA (Ex 2) | 3 |
| H-Gly | Lys | 3a | | |
| H-Gly | Orn | 3b | | |
| H-Gly | Nle | 3c | | |
| H-Glu | Arg | 3d | | |
| H-Glu-Gly | Arg | 3e | | |

TABLE 7-continued

Substrates of the type Y-Val-X-pNA fitting the active-site of thrombin like fibrinogen.

| Y | X | Code | Derived from | Code |
|---|---|---|---|---|
| H-Glu-Gly-Gly | Arg | 3f | | |
| H-Glu-Gly-Gly-Gly | Arg | 3g | | |
| H-Glu-Gly-Pro-Gly | Arg | 3h | | |
| H-Glu-Pro-Gly-Gly | Arg | 3i | | |

Unprotected amino functions are suitably protonated (HCl) to give neutral solutions in plain water.

TABLE 8

Decay constants of euglothrombin in plasma in the presence of Msc-Val-Arg-pNA.HCl at different concentrations.

| [S] μM | $k_{overall}$ $min^{-1}$ | $k_1$ $min^{-1}$ | $k_2$ $min^{-1}$ | t½ s | $k_{2,M}$ $min^{-1}$ | $k_{1,corr}$ $min^{-1}$ | $(k_{1,corr})$ $min^{-1}$ |
|---|---|---|---|---|---|---|---|
| 0 | 2.578 | 2.262 | 0.316 | 16.13 | 0.225 | 2.183 | 1.508 |
| 200 | 1.958 | 1.729 | 0.229 | 21.24 | 0.198 | 1.590 | 1.098 |
| 500 | 1.792 | 1.614 | 0.178 | 23.22 | 0.178 | 1.444 | 0.998 |
| 1000 | 1.104 | 0.980 | 0.124 | 37.70 | 0.144 | 0.790 | 0.546 |

TABLE 9

Decay constants of euglothrombin in plasma in the presence of 2HCl.H-Glu-Gly-Gly-Val-Arg-PNA at different concentrations.

| [S] μM | $k_{overall}$ $min^{-1}$ | $k_1$ $min^{-1}$ | $k_2$ $min^{-1}$ | t½ s | $k_{2,M}$ $min^{-1}$ | $k_{1,corr}$ $min^{-1}$ | $(k_{1,corr})$ $min^{-1}$ |
|---|---|---|---|---|---|---|---|
| 0 | 2.578 | 2.262 | 0.316 | 16.13 | 0.225 | 2.183 | 1.508 |
| 200 | 2.159 | 1.946 | 0.213 | 19.26 | 0.220 | 1.769 | 1.223 |
| 500 | 2.024 | 1.733 | 0.291 | 21.04 | 0.192 | 1.662 | 1.149 |
| 1000 | 1.766 | 1.594 | 0.172 | 23.56 | 0.169 | 1.427 | 0.987 |

$k_{overall} = k_1 + k_2 + 0.170$;
$k_1$: AT-III dependent decay of thrombin;
$k_2$: _$\alpha_2$M dependent decay of thrombin;
$k_{overall}$, $k_1$ and $k_2$ are determined in a decay experiment;
$k_{2,M}$: $k_2$ determined by the subsampling method;
$k_{1,corr}$: $k_1$ after correcting for $k_{2,M}$ and 0.170;
$k_{1,corr,control}/1.508 = 2.183/1.508 = 1.448$ μM AT-III,
$(k_{1,corr}) = k_{1,corr}/1.397$.

Sequence Listing

Figure 1:
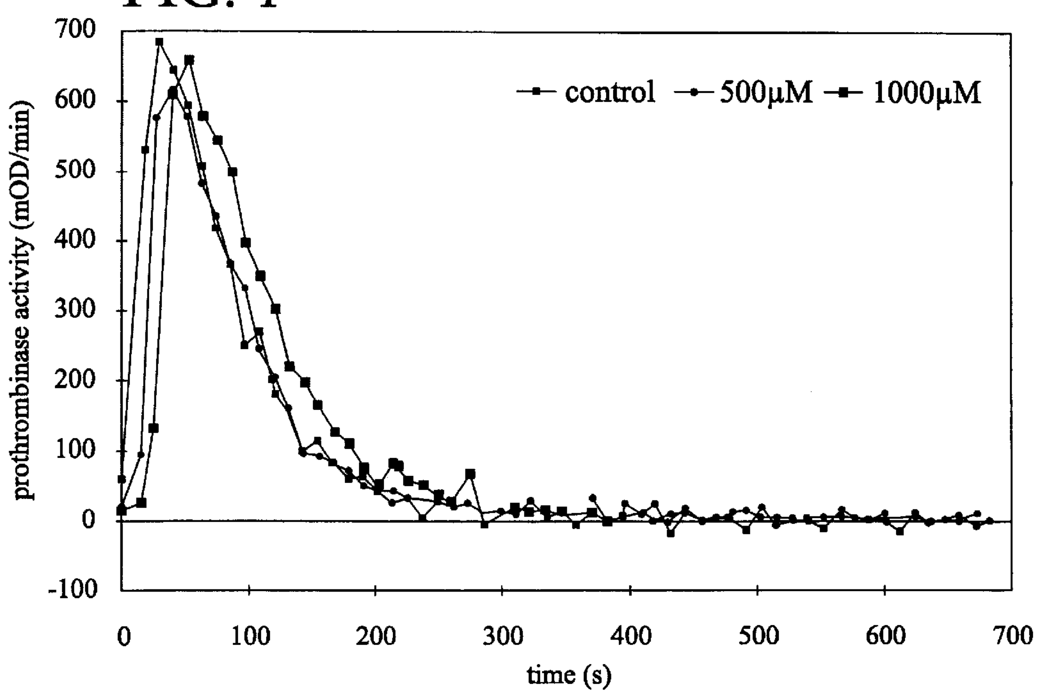
FIG. 1: The influence of 2HCl.H-Val-Arg-pNA on the prothrombinase activity in tissue factor triggered plasma: control (left curve), 500 (middle curve) and 1000 (right curve) μM 2HCl.H-Val-Arg-pNA
Figure 2:
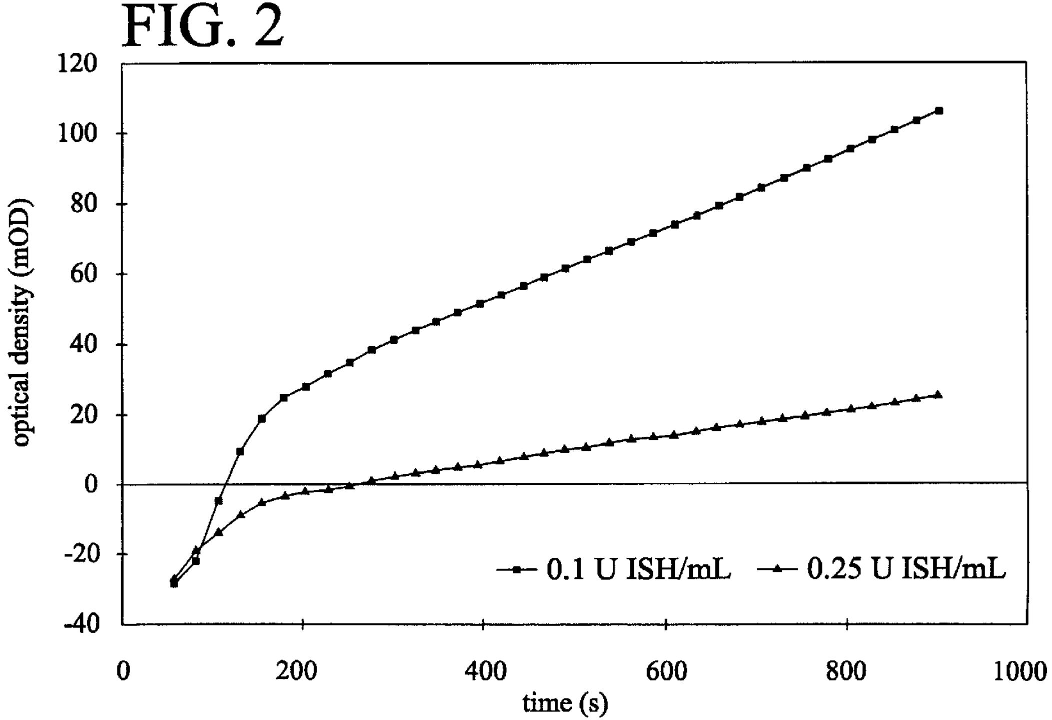
FIG. 2: Continuous optical density curves from extrinsic triggered plasma in the presence of international standard heparin using Msc-Val-Arg-pNA.HCl as substrate at 500 μM (top curve at 0.1 U ISH/ml, bottom curve at 0.25 U ISH/ml).
Figure 3:
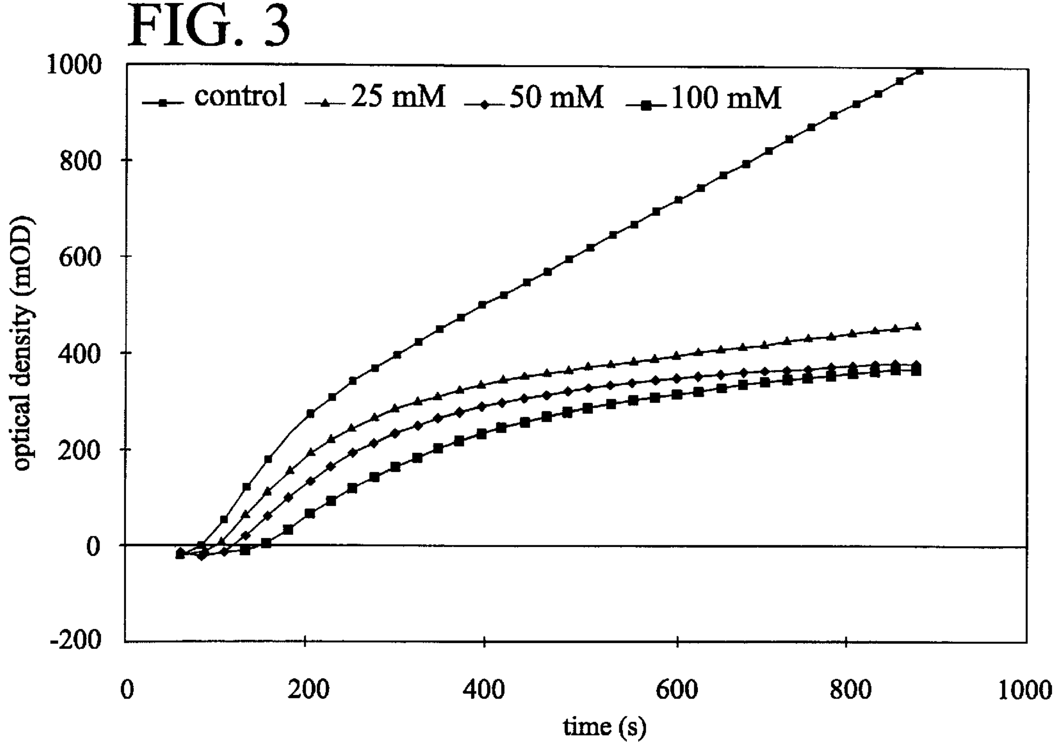
FIG. 3: Top curve is control, below said curve is the curve obtained at ( 25 mM, below the 25 mM curve is the curve at 50 mM. The lowest curve is obtained at 100 mM.
Figure 4:
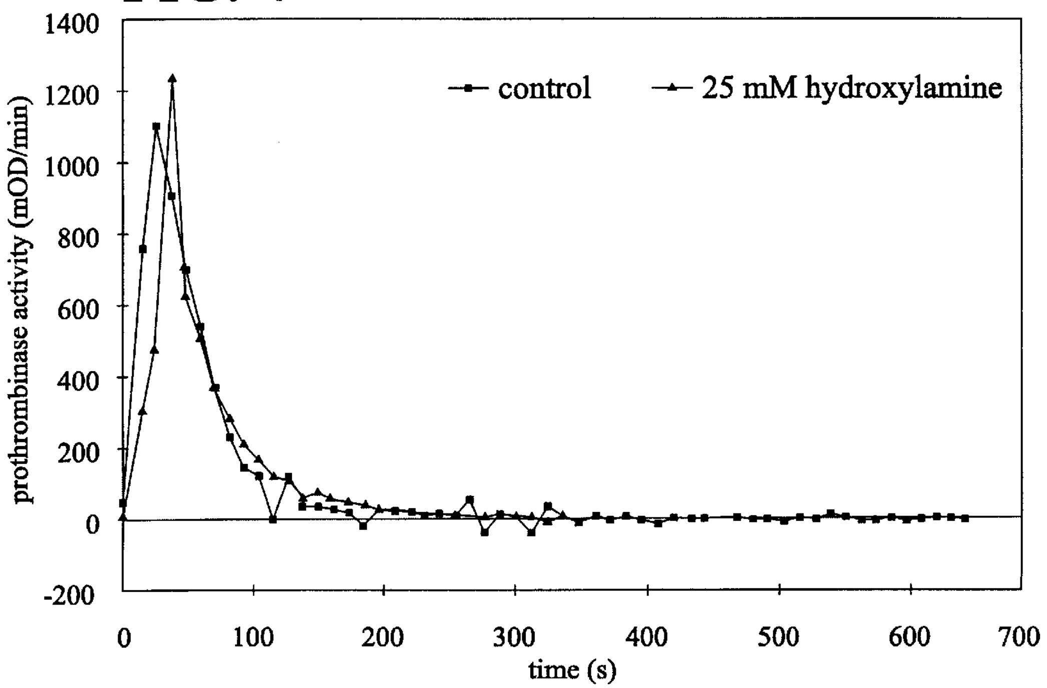
FIG. 4: The influence of hydroxylamine on the prothrombinase activity in extrinsically triggered plasma (left curve is control, right curve is at 25 mM hydroxylamine).
Figure 5:
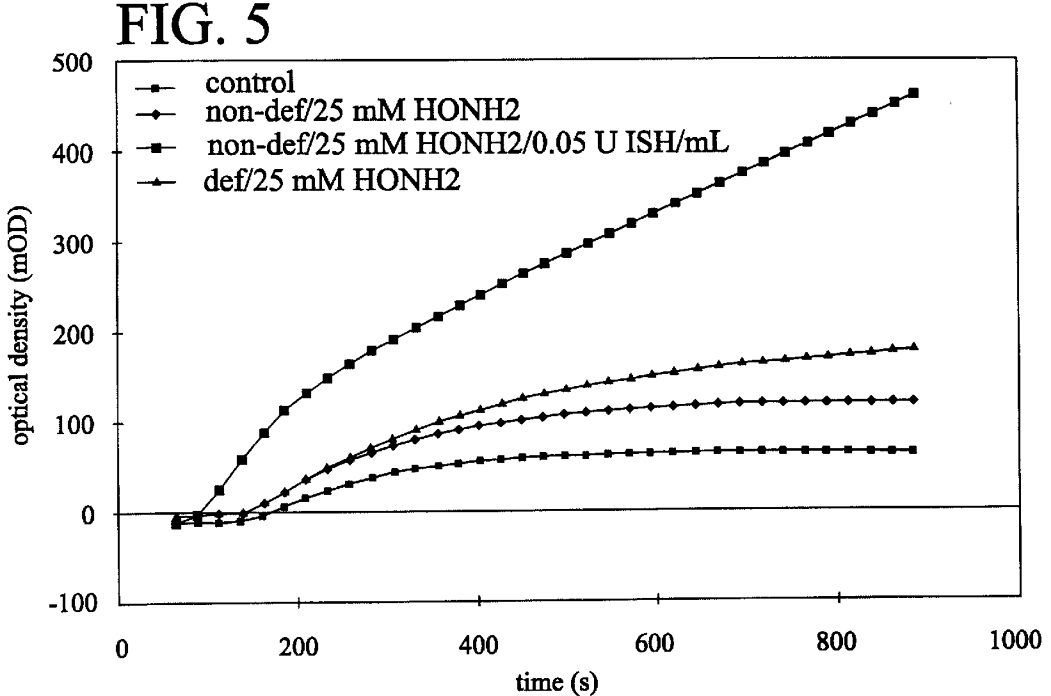
FIG. 5: Continuous thrombin generation curves triggered by tissue factor with Msc-Val-Arg-pNA.HCl as substrate at 500 μM in defibrinated (def) and non-defibrinated (non-def) plasma (top curve is the control curve, bottom curve is non def/25 mM $HONH_2$/0.05 U ISH/ml, second curve from the top is def/25 mM $HONH_2$, second curve from the bottom is non def/25 mM $HONH_2$).
Figure 6:
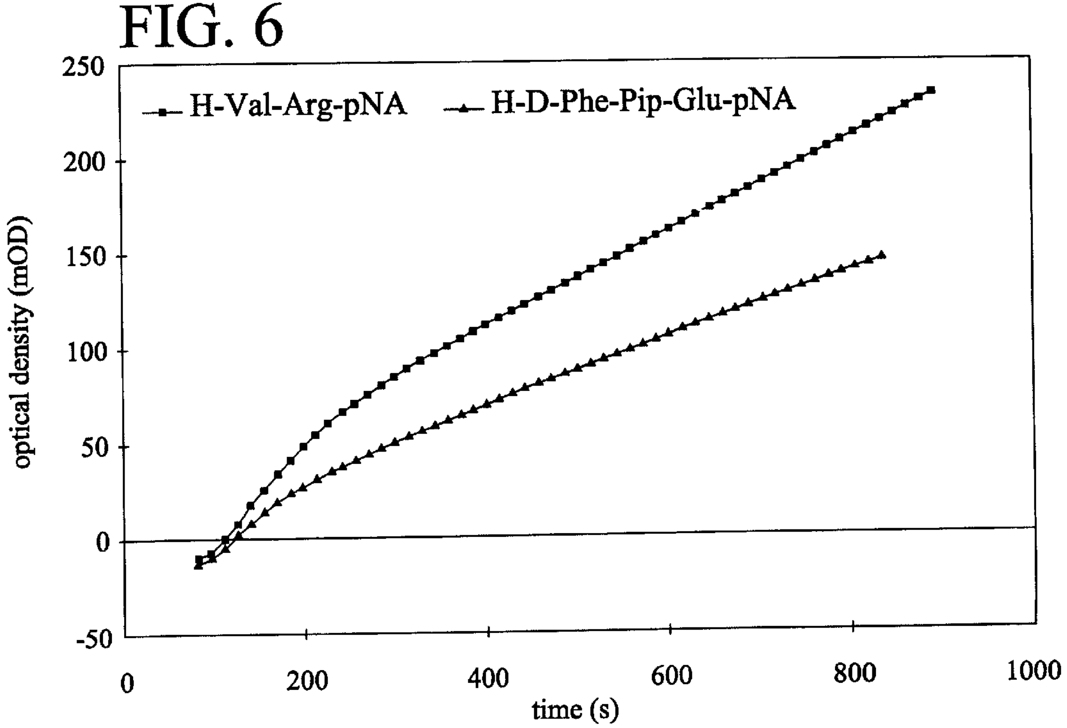
FIG. 6: Continuous optical density curves obtained from tissue factor triggered plasma using the substrates: 2HCl.H-Val-Arg-pNA and HCl.H-D-Phe-Pip-Glu-pNA at 500 μM.
Figure 7:
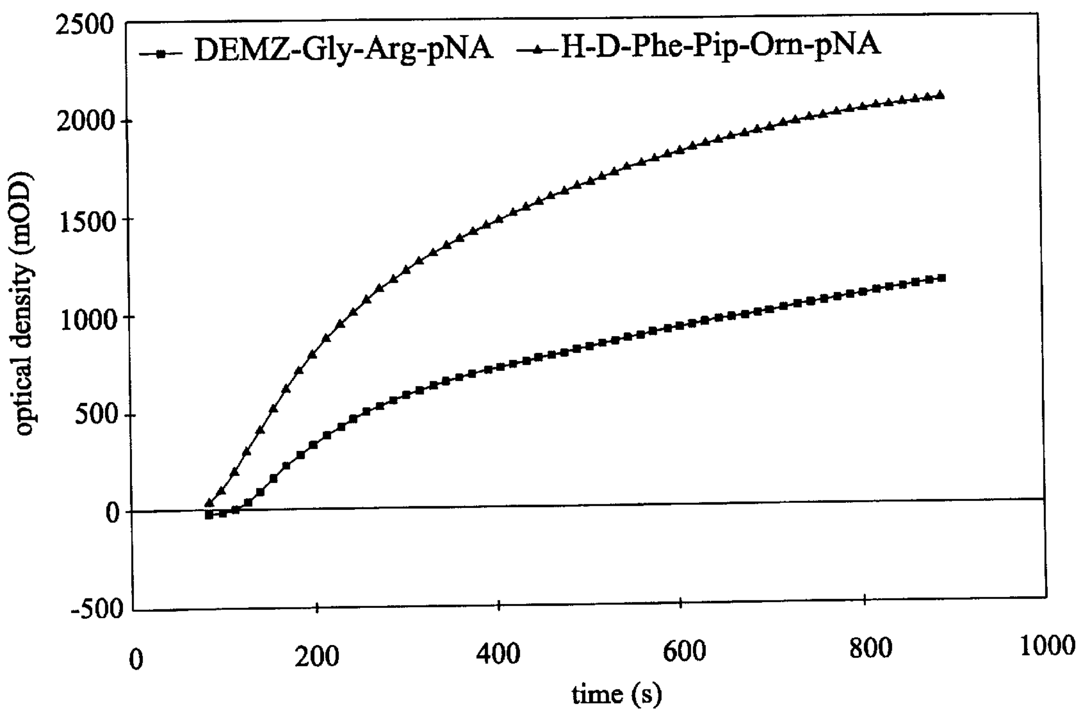
FIG. 7: Continuous optical density curves from tissue factor triggered plasma using as substrate DEMZ-Gly-Arg-pNA.HCl and 2HCl.H-D-Phe-Pip-Orn-pNA at 500 μM.
Figure 8:
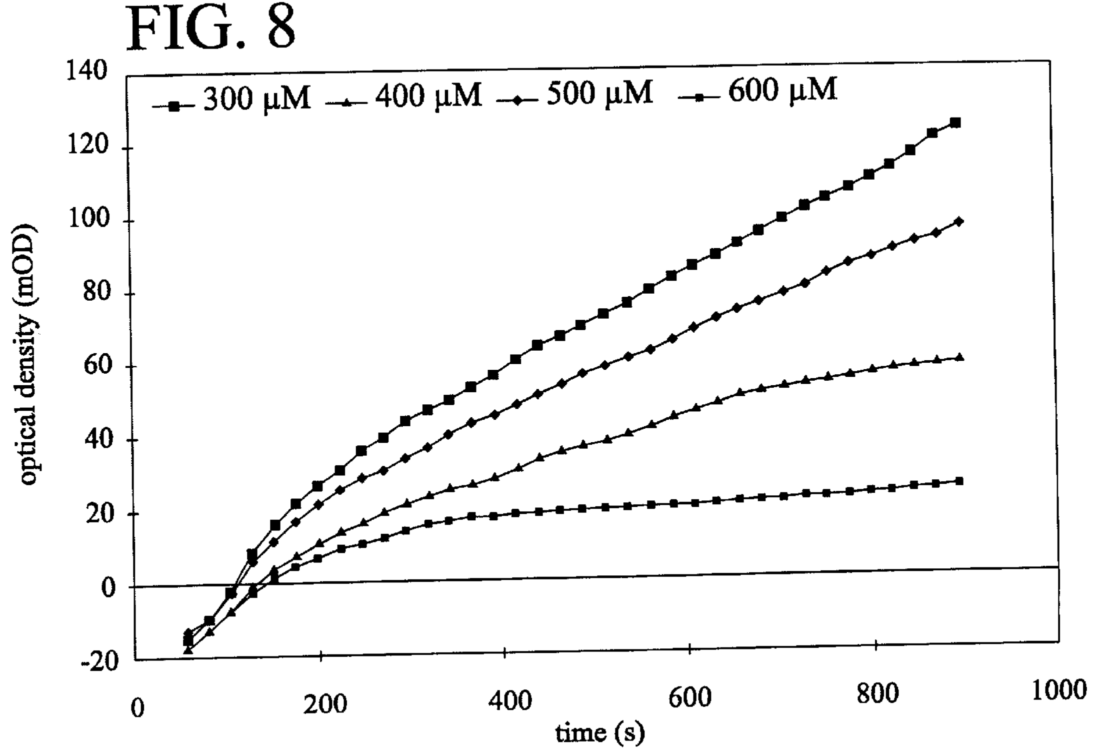
FIG. 8: Continuous optical density curves obtained from tissue factor triggered plasma using HCl.H-D-Phe-Pip-Glu-pNA as substrate (curves from top to bottom: top at 600 μM, then 500 μm, bottom 300 μM).
Figure 9:
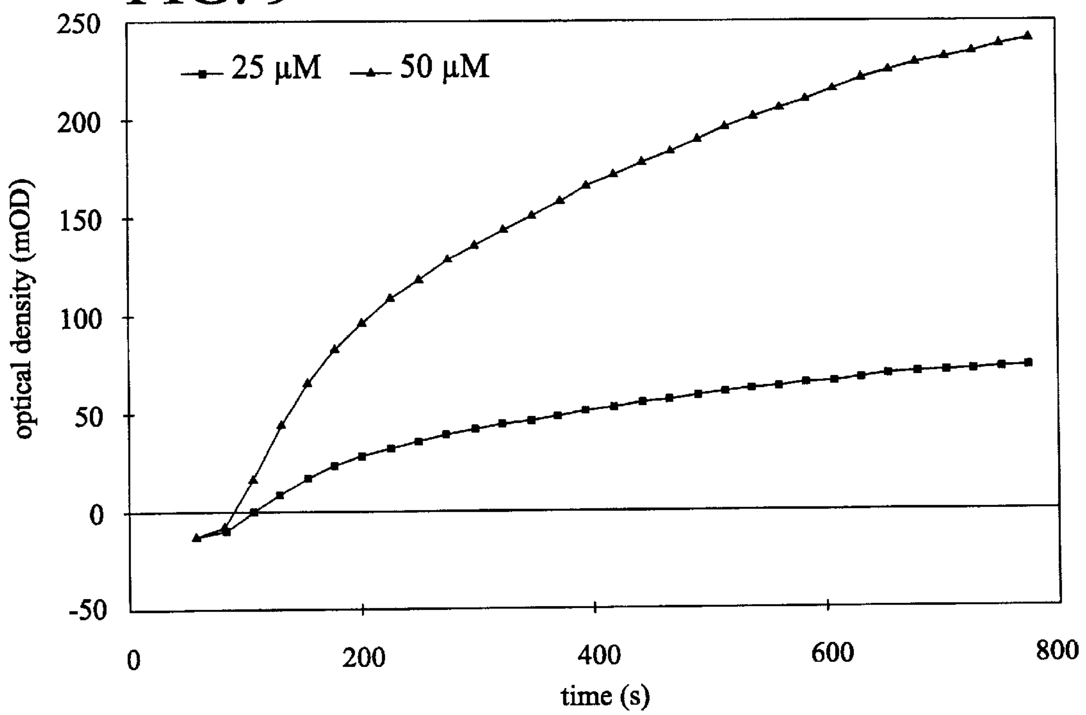
FIG. 9: Continuous optical density curves obtained from tissue factor triggered plasma using 2HCl.H-D-Phe-Pip-Orn-pNA as substrate at 25 μM (bottom curve) and 50 μM (top curve).
Figure 10:
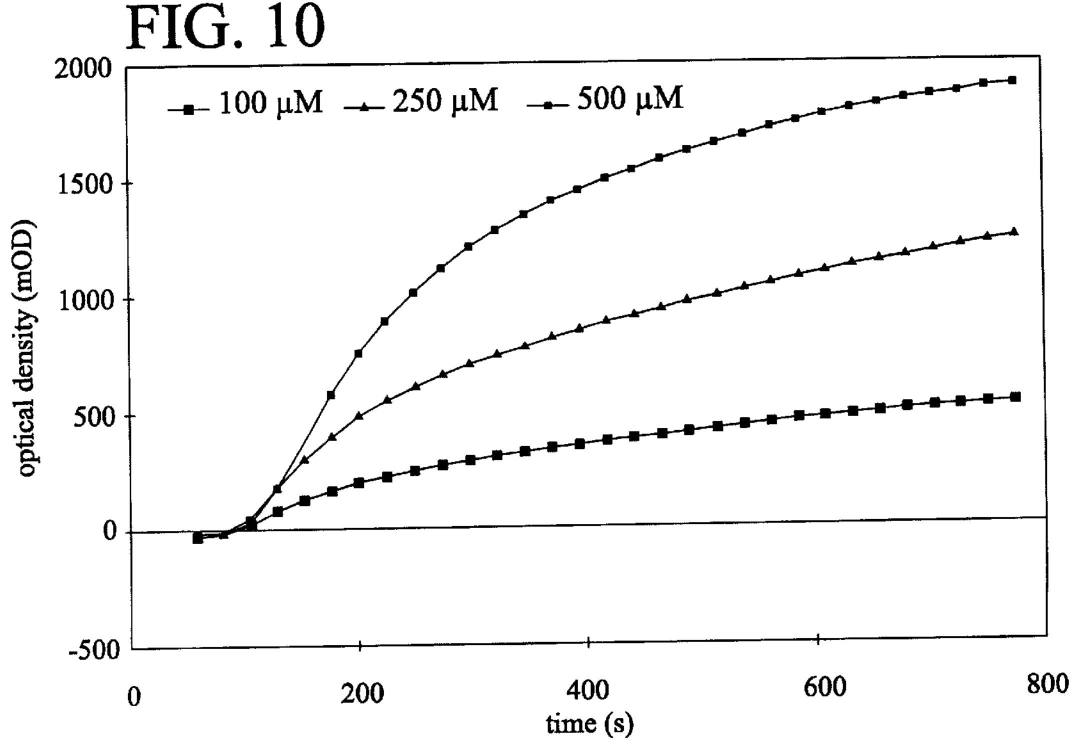
FIG. 10: Continuous optical density curves obtained from tissue factor triggered plasma using 2HCl.H-D-Phe-Pip-Orn-pNA as substrate at 100 μM (bottom curve), 250 μM (middle curve) and 500 μM (top curve).
Figure 11:
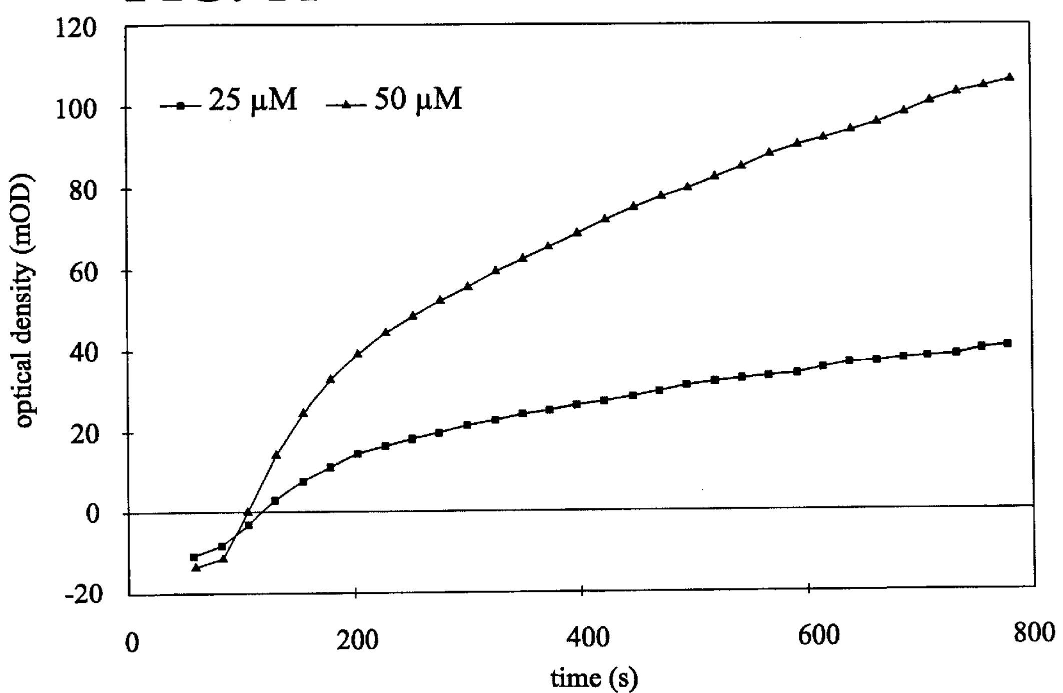
FIG. 11: Continuous optical density curves obtained from tissue factor triggered plasma using DEMZ-Gly-Arg-pNA.HCl as substrate at 25 μM (bottom curve) and 50 μM (top curve).
Figure 12:
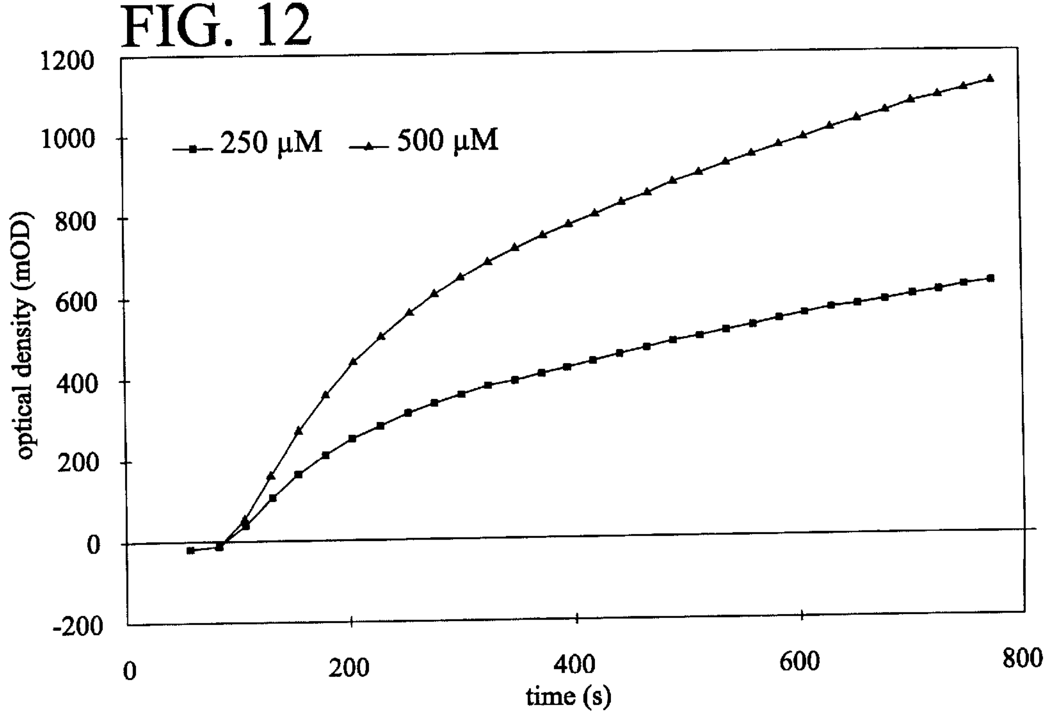
FIG. 12: Continuous optical density curves obtained from tissue factor triggered plasma using DEMZ-Gly-Arg-pNA.HCl as substrate at 250 μM (bottom curve) and 500 μM (bottom curve).
Figure 13:
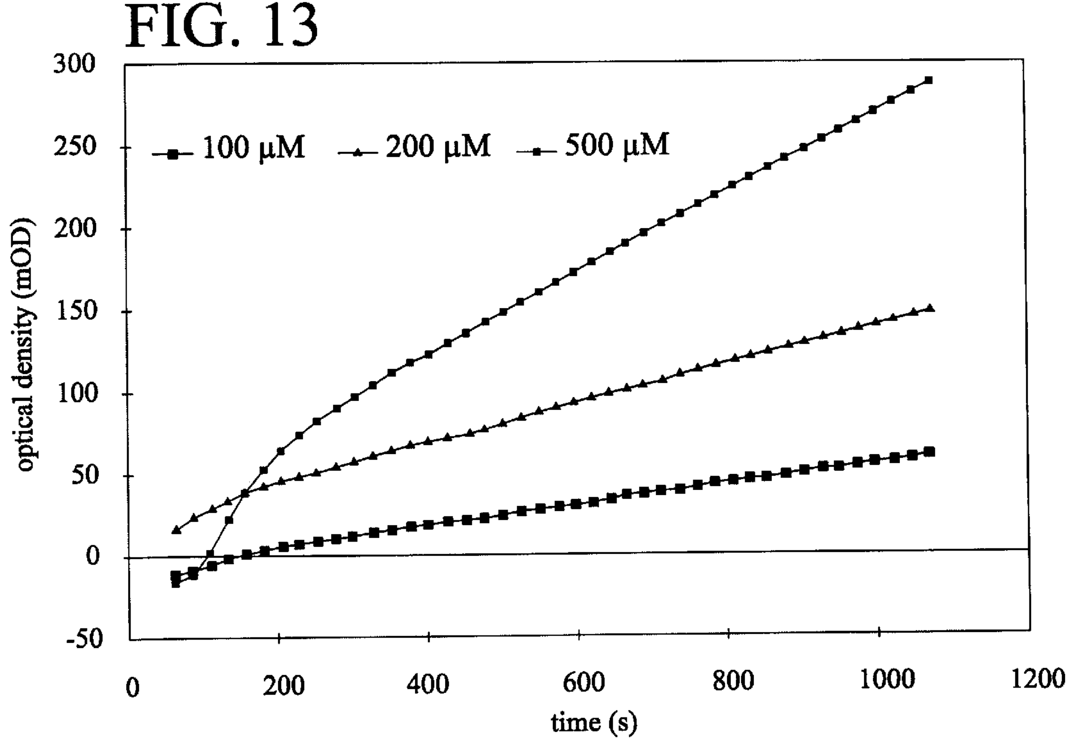
FIG. 13: Continuous optical density curves obtained from tissue factor triggered plasma using 2HCl.H-Val-Arg-pNA as substrate at 100 μM (bottom curve), 200 μM (middle curve) and 500 μM (top curve).
Figure 14:
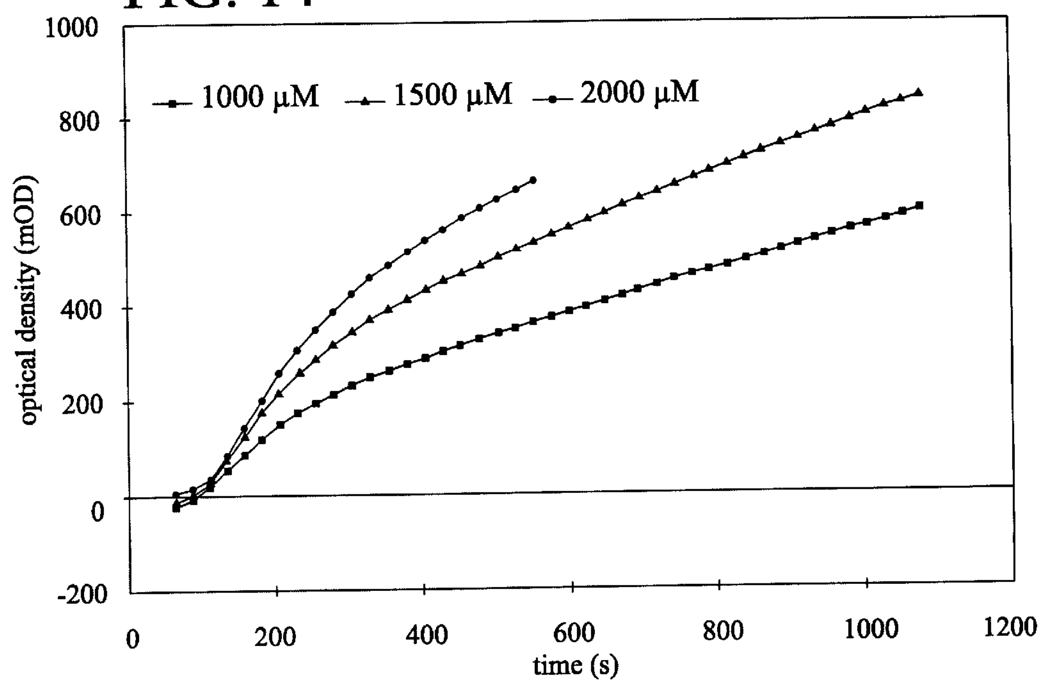
FIG. 14: Continuous optical density curves obtained from tissue factor triggered plasma using 2HCl.H-Val-Arg-pNA as substrate at 1000 μM (bottom curve), 1500 μM (middle curve) and 2000 μM (top curve).
Figure 15:
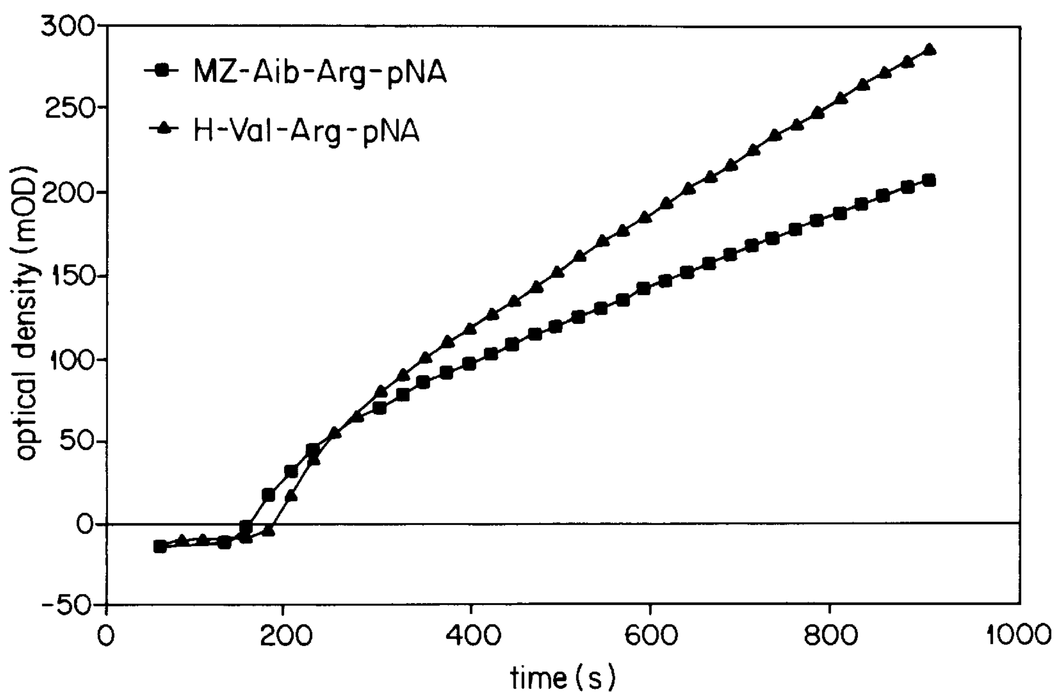
FIG. 15: Continuous optical density curves from intrinsic triggered plasma (Actin FS) using SQ68 (bottom curve) and 2HCl.H-Val-Arg-pNA (top curve) as substrates at a concentration of 500 μM.
Figure 16:
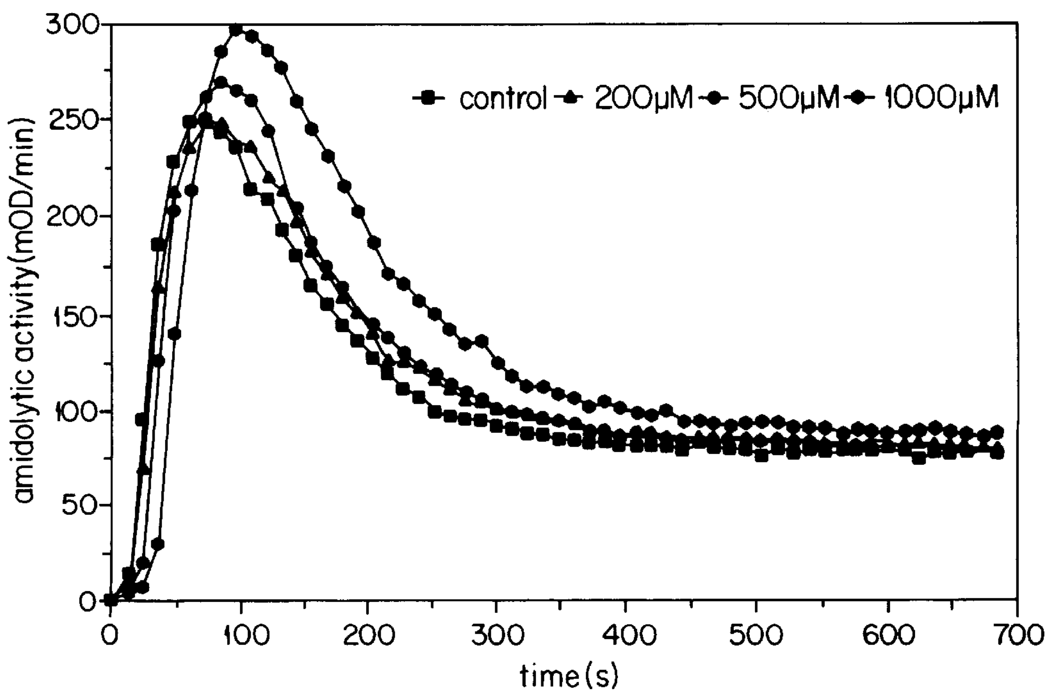
FIG. 16: Thrombin generation curves from tissue factor triggered plasma obtained by the subsampling method. The influence of additional 2HCl.H-Val-Arg-pNA at different concentrations (200 μM, 500 μM and 1000 μM curves 2–4 from left to right) on thrombin generation. The amidolytic activity in OD/min (Y axis) against time (s) on the X axis. (The left curve, closest to Y axis is the control curve no. 1.)
Figure 17:
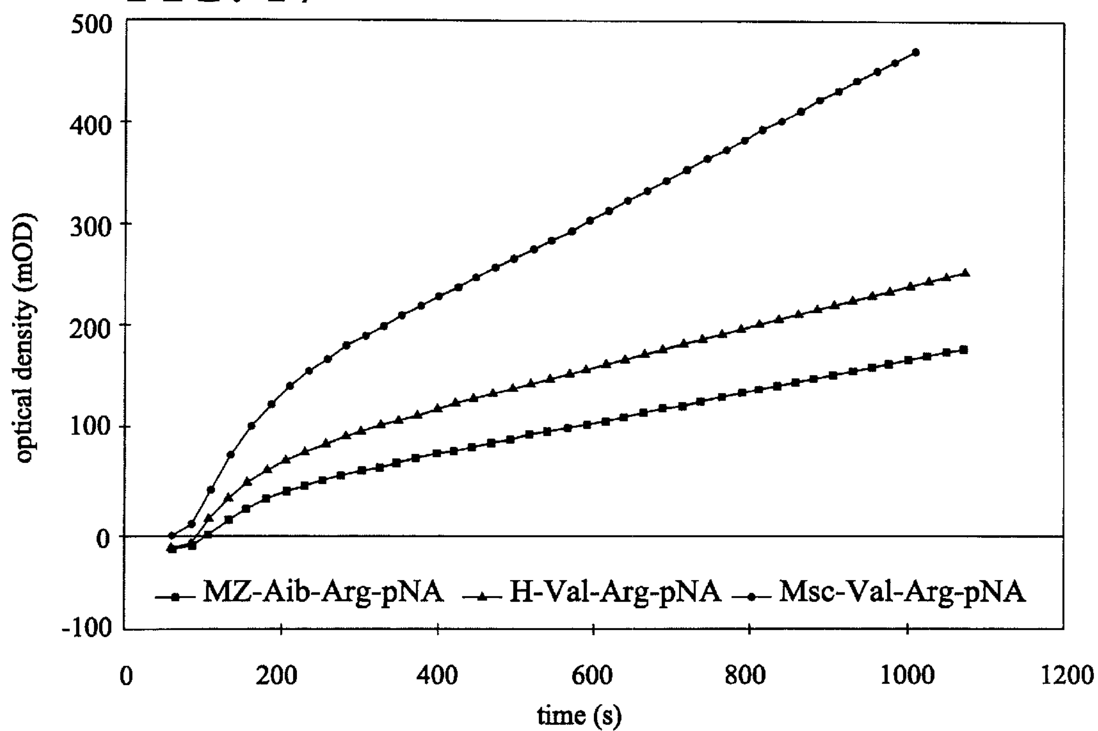
FIG. 17: Continuous optical density curves from extrinsic triggered plasma using the substrates MZ-Aib-Arg-pNA.HCl (SQ68)(bottom curve), 2HCl.H-Val-Arg-pNA (middle curve) and Msc-Val-Arg-pNA.HCl (top curve) at 500 μM.
Figure 18:
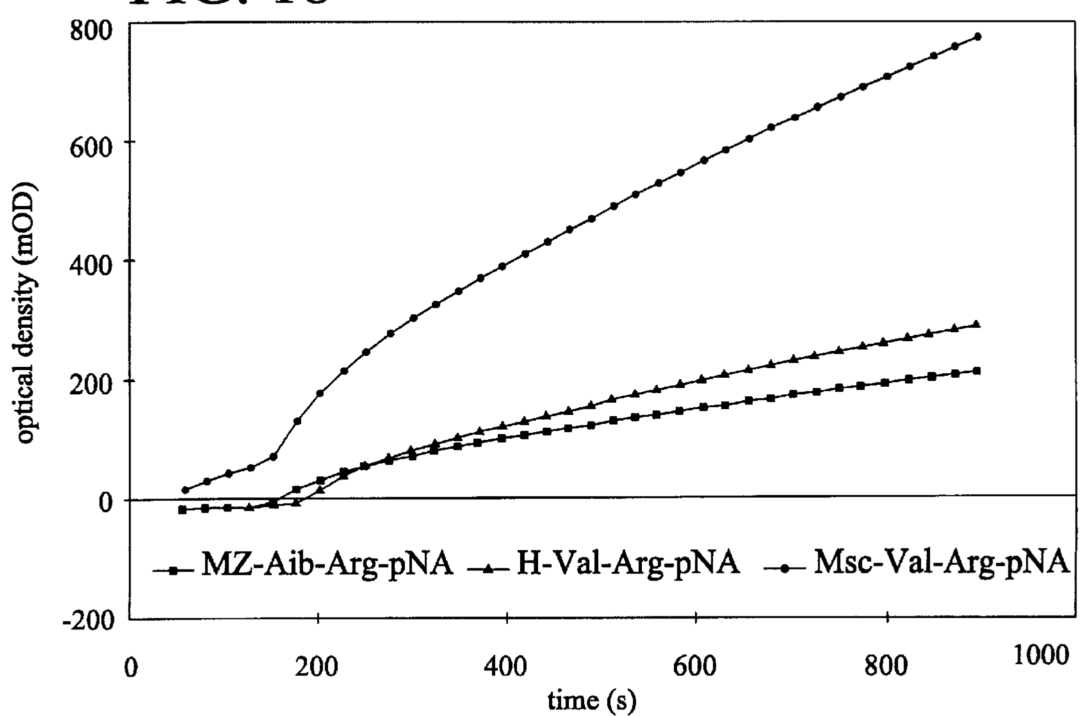
FIG. 18: Continuous optical density curves from intrinsic triggered plasma using the substrates MZ-Aib-Arg-pNA.HCl (SQ68)(bottom curve), 2HCl.H-Val-Arg-pNA (middle curve) and Msc-Val-Arg-pNA.HCl (top curve) at 500 μM.
Figure 19:
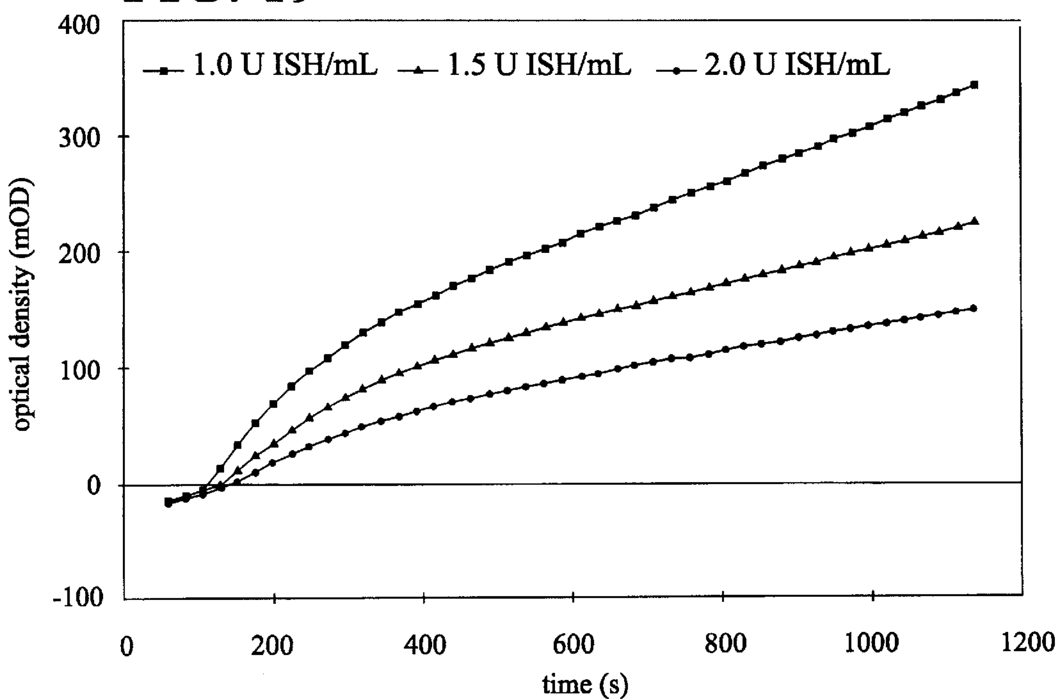
FIG. 19: Continuous optical density curves from extrinsic triggered plasma in the presence of international standard heparin using Boc-Gly-Val-Arg-pNA.HCl as substrate at 500 μM. The top curve is obtained at 1.0 U ISH/ml. The middle curve is obtained at 1.5 U ISH/ml. The bottom curve is obtained at 2.0 U ISH/ml.
Figure 20:
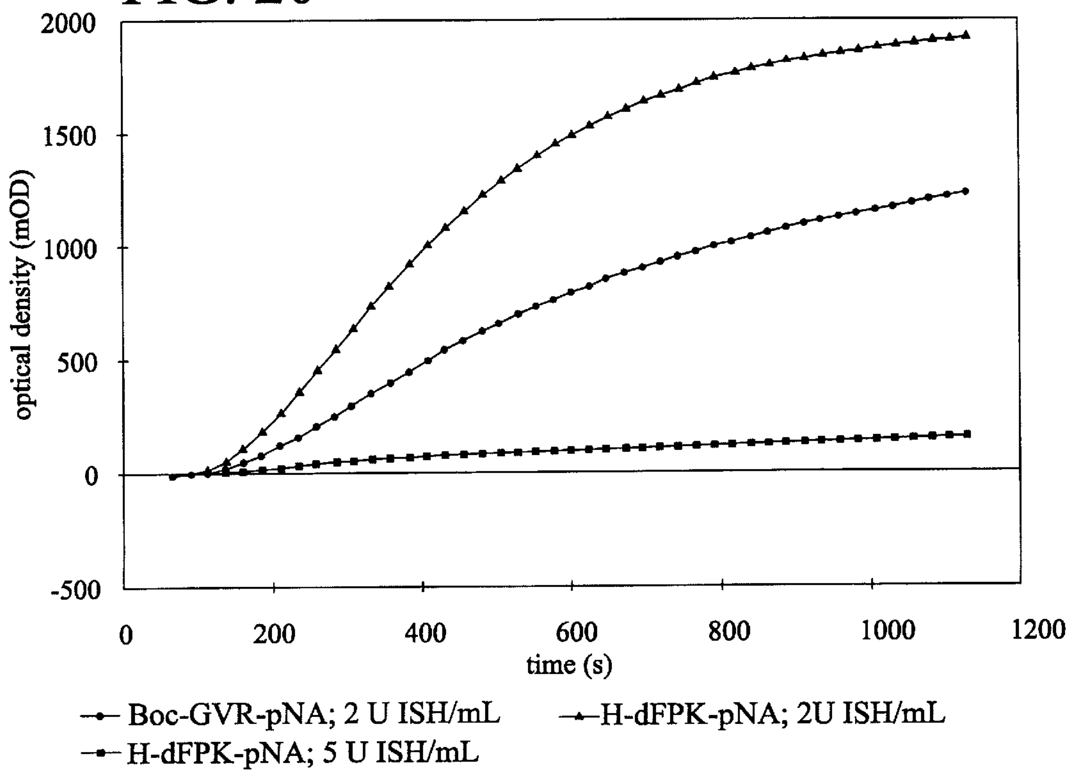
FIG. 20: Continuous optical density curves from extrinsic triggered plasma in the presence of international standard heparin using Boc-Gly-Val-Arg-pNA.HCl and 2HCl.H-D-Phe-Pro-Lys-pNA as substrates at 500 μM. The bottom curve is obtained at 2 U ISH/ml with Boc-Gly-Val-Arg-pNA. The middle curve is obtained at 24 ISH/ml. The bottom curve is obtained at 5 U ISH/ml. The latter two curves are obtained for 2 HCl-N-D-Phe-Pro-Lys-pNA.

Sequence of human fibrinogen Aα(25-23) tricosapeptide (I) Seq. id no. 1

H-Ala-Asp-Ser-Gly-Glu$^{5}$-Gly-Asp-Phe-Leu-Ala$^{10}$-Glu-Gly-Gly-Gly-Val$^{15}$-Arg-Gly-Pro-Arg-Val$^{20}$-Val-Glu-Arg-OH

What is claimed is:

1. A method for determining the ETP (endogenous thrombin potential) of a sample, said sample comprising at least 0.07 U ISH/ml due to at least one member selected from the group consisting of heparin and one or more other anticoagulants, resulting in a total anticoagulant activity or equivalent to at least 0.07 U ISH/ml, comprising using a thrombin substrate or a salt thereof that is soluble in the sample in the determination of the ETP of said sample, wherein said thrombin substrate is selected from the group consisting of:

1) a dipeptide thrombin substrate comprising the formula P-Val-Xaa-S, wherein P is an amino protective group, said amino protective group is non-aromatic, polar, and fits in the aryl binding pocket of thrombin, Val is a valine residue attached via a peptide bond to Xaa, Xaa is an amino acid residue comprising a terminal guanidino group or ureido group separated by at least 2 carbon atoms from the peptide backbone, said amino acid residue being attached to S, S is a signal group that can be enzymatically hydrolyzed with the proviso that the substrate is not $CH_3O$—CO—$CH_2$—CO-L-Val-Arg-pNa or H-Val-Arg-p-nitroanilide (pNa), 2) a thrombin substrate comprising the structure Zaa-Pipecolyl-Yaa-S or Zaa-Pro-Yaa-S, wherein Zaa represents D-Phenylalanine, D-Tryptophan or D-Tyrosine, Pro represents proline, Yaa is an amino acid residue other than arginine and S is a signal marker, 3) a thrombin substrate of the formula Boc-Gly-Val-Arg-p-nitroanilide or a salt thereof, 4) a thrombin substrate of the formula H-Glu-Gly-Gly-Val-Arg-p-nitroanilide (SEQ ID NO:3) or a salt thereof and 5) H-Val-Arg-pNa.

2. A method according to claim 1, wherein the sample comprises anticoagulant resulting in a total anticoagulant activity of or equal to at the most 0.25 U ISH/ml activity and the substrate is selected from the group consisting of:

1) a dipeptide thrombin substrate comprising the formula P-Val-Xaa-S, wherein

P is an amino protective group, said amino protective group is non-aromatic, polar, and fits in the aryl binding pocket of thrombin, Val is a valine residue attached via a peptide bond to Xaa, Xaa is an amino acid residue comprising a terminal guanidino group or ureido group separated by at least 2 carbon atoms from the peptide backbone, said amino acid residue being attached to S, and S is a signal group that can be enzymatically hydrolysed with the proviso that the substrate is not $CH_3O$—CO—$CH_2$—CO-L-Val-Arg-p-nitroanilide or H-Val-Arg-p-nitroanilide and 2) a thrombin substrate of the formula H-Glu-Gly-Gly-Val-Arg-p-nitroanilide or a salt thereof and 5) H-Val-Arg-pNa.

3. A method for determining the ETP of a sample said sample comprising anticoagulant resulting in a total anticoagulant activity of or equivalent to 0.0–0.25 U ISH/ml said method comprising using a thrombin substrate or a salt of the substrate that is soluble in the sample in the determination of the ETP of said sample, wherein said thrombin substrate is selected from the group consisting of dipeptide thrombin substrates including the formula P-Val-Xaa-S, wherein P is an amino protective group, said amino protective group is non-aromatic, polar, and fits in the aryl binding pocket of thrombin, Val is a valine residue attached via a peptide bond to Xaa, Xaa is an amino acid residue comprising a terminal guanidino group or ureido group separated by at least 2 carbon atoms from the peptide backbone, said amino acid residue being attached to S, S is a signal group such as a that can be enzymatically hydrolyzed with the proviso that the substrate is not $CH_3O$—CO—$CH_2$—CO-L-Val-Arg-p-nitroanilide or H-Val-Arg-p-nitroanilide and a thrombin substrate of the formula H-Glu-Gly-Gly-Val-Arg-p-nitroanilide (SEQ ID NO: 3) or a salt thereof.

4. A dipeptide thrombin substrate comprising the formula P-Val-Xaa-S, wherein P is an amino protective group, said amino protective group is non aromatic, polar, and fits in the aryl binding pocket of thrombin, Val is a valine residue attached via a peptide bond to Xaa, Xaa is an amino acid residue comprising a terminal guanidino group or ureido group separated by at least 2 carbon atoms from the peptide backbone, said amino acid residue being attached to S, and S is a signal group that can be enzymatically hydrolyzed with the proviso that the substrate is not $CH_3O$—CO—$CH_2$—CO-L-Val-Arg-p-nitroanilide or H-Val-Arg-p-nitroanilide.

5. A substrate according to claim 4, wherein P is an organic moiety.

6. A substrate according to claim 4, wherein P is methylsulphonylethyloxycarbonyl (Msc).

7. A substrate according to claim 4, wherein S is paranitroanilide (pNa).

8. A substrate according to claim 4, wherein Xaa is an amino acid residue comprising a terminal guanidino group with at least two carbon atoms separating the guanidino group from the peptide backbone.

9. A substrate according to claim 4, wherein Xaa is an amino acid residue comprising a side chain longer than that of ornithine.

10. A substrate according to claim 4, wherein Xaa is an amino acid residue comprising a terminal guanidino group separated from the peptide backbone by a bivalent group of at least two carbon atoms, Xaa being respectively norarginine or homoarginine.

11. A substrate according to claim 4, wherein Xaa is an amino acid residue comprising a terminal guanidino group wherein said guanidino group is separated from the peptide backbone by an ether or thioether linkage.

12. A substrate according to claim 4, wherein Xaa is an amino acid residue comprising a terminal guanidino group wherein said guanidino group is separated from the peptide backbone by a phenyl or cyclohexyl group, with said phenyl or cyclohexyl optionally being substituted.

13. A substrate according to claim 4, wherein Xaa is arginine.

14. A substrate according to claim 4, being Msc-Val-Arg-pNa.

15. A substrate according to claim 4, wherein Xaa is an amino acid residue comprising a terminal ureido group with at least two carbon atoms separating the ureido group from the peptide backbone.

16. A substrate according to claim 4, wherein Xaa is an amino acid residue comprising a side chain longer than that of ornithine.

17. A substrate according to claim 4, wherein Xaa is an amino acid residue comprising a terminal ureido group with at least two carbon atoms separating the ureido group from the peptide backbone and Xaa is an amino acid residue comprising a side chain longer than that of ornithine.

18. A substrate according to claim 4, wherein Xaa is an amino acid residue comprising a terminal ureido group separated from the peptide backbone by a bivalent group of at least two carbon atoms.

19. A substrate according to claim 4, wherein Xaa is an amino acid residue comprising a terminal ureido group wherein said ureido group is separated from the peptide backbone by an ether or thioether linkage.

20. A substrate according to claim 4, wherein Xaa is an amino acid residue comprising a terminal ureido group wherein said ureido group is separated from the peptide backbone by a phenyl or cyclohexyl group, with said phenyl or cyclohexyl optionally being substituted.

21. A substrate according to claim 4, wherein Xaa is citrullin.

22. A substrate according to claim 4, wherein the Km for thrombin is 800–1250 mM.

23. A substrate according to claim 4, wherein the $k_{cal}$ for thrombin is 0.4–0.9 $s^{-1}$.

24. A substrate according to claim 4, wherein the $K_m/K_{cal}$ for thrombin is 200–300 $Ms^{-1}$.

25. A substrate according to claim 4, wherein the $K_m$ for Factor Xa is 500 microM or more.

26. A substrate according to claim 4, wherein the $K_{cal}$ for Factor Xa is O $s^{-1}$.

27. A thrombin substrate of the formula H-Glu-Gly-Gly-Val-Arg-pNa (SEQ ID NO:3) or a salt thereof.

28. A method according to claim 1, wherein said method is performed in a continuous assay.

29. A substrate according to claim 4, wherein Xaa is an amino acid residue comprising a side chain longer than that of lysine.

30. A substrate according to claim 4, wherein Xaa is an amino acid residue comprising a side chain equal to that of arginine.

31. A substrate according to claim 4, wherein Xaa is an amino acid residue comprising a terminal ureido group with at least two carbon atoms separating the ureido group from the peptide backbone and Xaa is an amino acid residue comprising a side chain longer than that of lysine.

32. A substrate according to claim 4, wherein Xaa is an amino acid residue comprising a terminal ureido group with at least two carbon atoms separating the ureido group from the peptide backbone and Xaa is an amino acid residue comprising a side chain equal to that of arginine.

33. A substrate according to claim 4, wherein the Km for thrombin is 840–1000 mM.

34. A substrate according to claim 4, wherein the $k_{cal}$ for thrombin is 0.50–0.85 $s^{-1}$.

35. A substrate according to claim 4, wherein the $K_m/K_{cal}$ for thrombin is 225–275 $Ms^{-1}$.

36. A substrate according to claim 4, wherein the $K_m/K_{cal}$ for thrombin is 240–260 $Ms^{-1}$.

* * * * *